US012391740B2

(12) United States Patent
Schneider et al.

(10) Patent No.: US 12,391,740 B2
(45) **Date of Patent: *Aug. 19, 2025**

(54) COMPOSITIONS AND METHODS FOR TREATING CANCER WITH ANTI-BCMA IMMUNOTHERAPY

(71) Applicant: LENTIGEN TECHNOLOGY, INC., Gaithersburg, MD (US)

(72) Inventors: Dina Schneider, Potomac, MD (US); Zhongyu Zhu, Frederick, MD (US); Boro Dropulic, Ellicott City, MD (US); Bang Khoa Vu, Frederick, MD (US); Leah Marie Alabanza, Montgomery Village, MD (US)

(73) Assignee: LENTIGEN TECHNOLOGY, INC., Gaithersburg, MD (US)

( * ) Notice: Subject to any disclaimer, the term of this patent is extended or adjusted under 35 U.S.C. 154(b) by 1056 days.

This patent is subject to a terminal disclaimer.

(21) Appl. No.: 17/337,018

(22) Filed: Jun. 2, 2021

(65) Prior Publication Data

US 2021/0361709 A1 Nov. 25, 2021

Related U.S. Application Data

(63) Continuation of application No. 16/888,020, filed on May 29, 2020, now Pat. No. 11,052,112.

(60) Provisional application No. 62/854,574, filed on May 30, 2019.

(51) Int. Cl.

| | |
|---|---|
| ***C12N 15/85*** | (2006.01) |
| ***A61K 35/17*** | (2025.01) |
| ***A61K 39/00*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***A61P 35/02*** | (2006.01) |
| ***C07K 14/705*** | (2006.01) |
| ***C07K 14/725*** | (2006.01) |
| ***C07K 16/28*** | (2006.01) |
| ***C12N 5/0783*** | (2010.01) |
| *C12N 15/63* | (2006.01) |

(52) U.S. Cl.

CPC .......... *C07K 14/7051* (2013.01); *A61K 40/11* (2025.01); *A61K 40/31* (2025.01); *A61K 40/4202* (2025.01); *A61K 40/4215* (2025.01); *A61P 35/00* (2018.01); *C07K 14/70517* (2013.01); *C07K 14/70521* (2013.01); *C07K 14/70578* (2013.01); *C07K 16/2878* (2013.01); *C12N 5/0636* (2013.01); *A61K 2239/31* (2023.05); *A61K 2239/48* (2023.05); *C12N 15/63* (2013.01)

(58) Field of Classification Search

None

See application file for complete search history.

(56) References Cited

U.S. PATENT DOCUMENTS

| | | | |
|---|---|---|---|
| 3,060,165 | A | 10/1962 | Craig et al. |
| 3,896,111 | A | 7/1975 | Kupchan et al. |
| 4,137,230 | A | 1/1979 | Hashimoto et al. |
| 4,151,042 | A | 4/1979 | Higashide et al. |
| 4,235,871 | A | 11/1980 | Papahadjopoulos et al. |
| 4,248,870 | A | 2/1981 | Miyashita et al. |
| 4,256,746 | A | 3/1981 | Miyashita et al. |
| 4,260,608 | A | 4/1981 | Miyashita et al. |
| 4,265,814 | A | 5/1981 | Hashimoto et al. |
| 4,294,757 | A | 10/1981 | Asai |
| 4,307,016 | A | 12/1981 | Asai |
| 4,308,268 | A | 12/1981 | Miyashita et al. |
| 4,308,269 | A | 12/1981 | Miyashita et al. |
| 4,309,428 | A | 1/1982 | Miyashita et al. |
| 4,313,946 | A | 2/1982 | Powell et al. |
| 4,315,929 | A | 2/1982 | Freedman et al. |
| 4,317,821 | A | 3/1982 | Miyashita et al. |
| 4,322,348 | A | 3/1982 | Asai et al. |
| 4,331,598 | A | 5/1982 | Hasegawa et al. |
| 4,361,650 | A | 11/1982 | Asai et al. |
| 4,362,663 | A | 12/1982 | Kida et al. |
| 4,364,866 | A | 12/1982 | Asai et al. |
| 4,371,533 | A | 2/1983 | Akimoto et al. |
| 4,424,219 | A | 1/1984 | Hashimoto et al. |
| 4,450,254 | A | 5/1984 | Isley et al. |
| 4,501,728 | A | 2/1985 | Geho et al. |

(Continued)

FOREIGN PATENT DOCUMENTS

| | | |
|---|---|---|
| EP | 0425235 | 9/1996 |
| WO | WO 2004/010957 | 2/2004 |
| WO | WO 2020/092848 | 5/2020 |

OTHER PUBLICATIONS

Attal et al., "A prospective, randomized trial of autologous bone marrow transplantation and chemotherapy in multiple myeloma," New England Journal of Medicine, Jul. 11, 1996, 335:91-99.

(Continued)

*Primary Examiner* — Maria Marvich

(74) *Attorney, Agent, or Firm* — Serge Sira; Gregory J. Hwa, Esq.; Fish & Richardson P.C.

(57) ABSTRACT

Chimeric antigen receptors containing BCMA antigen binding domains are disclosed. Nucleic acids, recombinant expression vectors, host cells, antigen binding fragments, and pharmaceutical compositions, relating to the chimeric antigen receptors are also disclosed. Methods of treating or preventing cancer in a subject, and methods of making chimeric antigen receptor T cells are also disclosed.

23 Claims, 10 Drawing Sheets

Specification includes a Sequence Listing.

(56) References Cited

U.S. PATENT DOCUMENTS

| | | | |
|---|---|---|---|
| 4,689,401 | A | 8/1987 | Ferris |
| 4,837,028 | A | 6/1989 | Allen |
| 4,880,935 | A | 11/1989 | Thorpe |
| 4,902,505 | A | 2/1990 | Pardridge et al. |
| 4,957,735 | A | 9/1990 | Huang et al. |
| 5,004,697 | A | 4/1991 | Pardridge et al. |
| 5,019,369 | A | 5/1991 | Presant et al. |
| 5,055,303 | A | 10/1991 | Riley, Jr. et al. |
| 5,079,163 | A | 1/1992 | Piatak, Jr. et al. |
| 5,188,837 | A | 2/1993 | Domb |
| 5,208,020 | A | 5/1993 | Chari et al. |
| 5,208,021 | A | 5/1993 | Johnson et al. |
| 5,254,342 | A | 10/1993 | Shen et al. |
| 5,268,164 | A | 12/1993 | Kozarich et al. |
| 5,271,961 | A | 12/1993 | Mathiowitz et al. |
| 5,413,797 | A | 5/1995 | Khan et al. |
| 5,416,064 | A | 5/1995 | Chari et al. |
| 5,506,206 | A | 4/1996 | Kozarich et al. |
| 5,514,670 | A | 5/1996 | Friedman et al. |
| 5,534,496 | A | 7/1996 | Lee et al. |
| 5,792,458 | A | 8/1998 | Johnson et al. |
| 6,441,163 | B1 | 8/2002 | Chari et al. |
| 10,294,304 | B2 | 5/2019 | Kuo et al. |
| 11,052,112 | B2 | 7/2021 | Schneider et al. |
| 2005/0238649 | A1 | 10/2005 | Doronina et al. |
| 2006/0024317 | A1 | 2/2006 | Boyd et al. |
| 2006/0074008 | A1 | 4/2006 | Senter et al. |
| 2017/0183418 | A1 | 6/2017 | Galletto |
| 2020/0023010 | A1 | 1/2020 | DiLillo et al. |
| 2020/0289572 | A1 | 9/2020 | Schneider et al. |

OTHER PUBLICATIONS

Avery et al., "BAFF selectively enhances the survival of plasmablasts generated from human memory B cells," The Journal of clinical investigation, Jul. 15, 2003, 112(2):286-297.

Brown et al., "Stem-like tumor-initiating cells isolated from IL13Rα2 expressing gliomas are targeted and killed by IL13-zetakine-redirected T cells," Clinical Cancer Research, Apr. 15, 2012, 18(8):2199-2209.

Child et al., "High-dose chemotherapy with hematopoietic stem-cell rescue for multiple myeloma," New England Journal of Medicine, May 8, 2003, 348(19):1875-1883.

Clay et al., "Efficient transfer of a tumor antigen-reactive TCR to human peripheral blood lymphocytes confers anti-tumor reactivity," The Journal of Immunology, Jul. 1, 1999, 163(1):507-513.

D'Aloia, "CAR-T cells: the long and winding road to solid tumors," Cell Death and Disease, 2018, pp. 1-12.

Deckert et al., "SAR650984, a novel humanized CD38-targeting antibody, demonstrates potent antitumor activity in models of multiple myeloma and other CD38+ hematologic malignancies," Clinical Cancer Research, Sep. 1, 2014, 20(17):4574-4583.

De-Xiu et al., "Pre-clinical validation of B cell maturation antigen (BCMA) as a target for T cell immunotherapy of multiple myeloma, " Oncotarget, May 25, 2018, 9(40):25764.

Di Stasi et al., "Inducible apoptosis as a safety switch for adoptive cell therapy," New England Journal of Medicine, Nov. 3, 2011, 365:1673-1683.

Fermand et al., "Single versus tandem high dose therapy (HDT) supported with autologous stem cell transplantation using unselected or CD-34-enriched ABSC: results of a two by two designed randomized trial in 230 young patients with multiple myeloma," The Hematol Journal, Jan. 2003, 4(suppl 1):559-560.

Foster et al., "Antitumor activity of EBV-specific T lymphocytes transduced with a dominant negative TGF-β receptor," Journal of Immunotherapy (Hagerstown, Md.: 1997), Jun. 2008, 31(5):500-505.

Fults et al., "Sustained-release of urease from a poloxamer gel matrix," PDA Journal of Pharmaceutical Science and Technology, Mar. 1, 1990, 44(2):58-65.

Funatsu et al., "The complete amino acid sequence of the A-chain of abrin-a, a toxic protein from the seeds of Abrus precatorius," Agricultural and Biological Chemistry, Apr. 1, 1988, 52(4):1095-1097.

Gillespie et al., "Phase I open study of the effects of ascending doses of the cytotoxic immunoconjugate CMB-401 (hCTMO1-calicheamicin) in patients with epithelial ovarian cancer," Annals of Oncology, Jun. 1, 2000, 11(6):735-741.

Goyal et al., "Inclusion of a furin-sensitive spacer enhances the cytotoxicity of ribotoxin restrictocin containing recombinant single-chain immunotoxins," Biochemical Journal, Jan. 15, 2000, 345(2):247-254.

Haso et al., "Anti-CD22-chimeric antigen receptors targeting B cell precursor acute lymphoblastic leukemia," Blood, Feb. 14, 2013 121 (7):1165-1174.

Hegde et al., "Combinational targeting offsets antigen escape and enhances effector functions of adoptively transferred T cells in glioblastoma," Molecular Therapy, Nov. 1, 2013, 21(11):2087-2101.

Ijntema et al., "Hydroxyapatite microcarriers for biocontrolled release of protein drugs," International Journal of Pharmaceutics, Dec. 5, 1994, 112(3):215-224.

Johnson et al., "Anti-tumor activity of CC49-doxorubicin immunoconjugates," Anticancer Research, Aug. 1995, 15(4):1387-1393.

Johnston et al., "Sustained delivery of interleukin-2 from a poloxamer 407 gel matrix following intraperitoneal injection in mice," Pharmaceutical Research, Mar. 1, 1992, 9(3):425-434.

Kloss et al., "Combinatorial antigen recognition with balanced signaling promotes selective tumor eradication by engineered T cells," Nature Biotechnology, Jan. 2013, 31(1):71-75.

Kochenderfer et al., "B-cell depletion and remissions of malignancy along with cytokine-associated toxicity in a clinical trial of anti-CD19 chimeric-antigen-receptor-transduced T cells," Blood, The Journal of the American Society of Hematology, Mar. 22, 2012, 119(12):2709-20.

Krishnan et al., "Autologous haemopoietic stem-cell transplantation followed by allogeneic or autologous haemopoietic stem-cell transplantation in patients with multiple myeloma (BMT CTN 0102): a phase 3 biological assignment trial," The Lancet Oncology, Dec. 1, 2011, 12(13):1195-203.

Kyle et al., "A long-term study of prognosis in monoclonal gammopathy of undetermined significance," New England Journal of Medicine, Feb. 21, 2002, 346(8):564-9.

Kyle et al., "Clinical course and prognosis of smoldering (asymptomatic) multiple myeloma," New England Journal of Medicine, Jun. 21, 2007, 356(25):2582-90.

Kyle et al., "Review of 1027 patients with newly diagnosed multiple myeloma," Clinic Proceedings, Jan. 1, 2003, 78(1):21-33.

Laird et al., "Isolation and characterization of tox mutants of corynebacteriophage beta," Journal of Virology, Jul. 1, 1976, 19(1):220-7.

Landgren et al., "Monoclonal gammopathy of undetermined significance (MGUS) consistently precedes multiple myeloma: a prospective study," Blood, May 28, 2009, 113(22):5412-7.

Landgren et al., "Racial disparities in the prevalence of monoclonal gammopathies: a population-based study of 12 482 persons from the national health and nutritional examination survey," Leukemia, Jul. 2014. 28(7):1537-42.

Langer, "Polymer-controlled drug delivery systems," Accounts of Chemical Research, Oct. 1, 1993, 26(10):537-42.

Lanitis et al., "Chimeric antigen receptor T Cells with dissociated signaling domains exhibit focused antitumor activity with reduced potential for toxicity in vivo," Cancer Immunology Research, Jul. 1, 2013, 1(1):43-53.

Lau et al., "Conjugation of doxorubicin to monoclonal anti-carcinoembryonic antigen antibody via novel thiol-directed cross-linking reagents," Bioorganic & Medicinal Chemistry, Oct. 1, 1995, 3(10):1299-304.

Lau et al., "Novel doxorubicin-monoclonal anti-carcinoembryonic antigen antibody immunoconjugate activity in vitro," Bioorganic & Medicinal Chemistry, Oct. 1, 1995, 3(10):1305-12.

Lee et al., "Calicheamicins, a novel family of antitumor antibiotics. 3. Isolation, purification and characterization of calicheamicins beta

(56) References Cited

OTHER PUBLICATIONS

1Br, gamma 1Br, alpha 21, alpha 31, beta II, gamma II and delta II," The Journal of Antibiotics, Jul. 1989, 42(7):1070-87.

Lehner et al., "Redirecting T cells to Ewing's sarcoma family of tumors by a chimeric NKG2D receptor expressed by lentiviral transduction or mRNA transfection," PloS one, Feb. 15, 2012, 7(2):e31210, 12 pages.

Long et al., "Lessons learned from a highly-active CD22-specific chimeric antigen receptor," Oncoimmunology, Apr. 1, 2013, 2(4):e23621, 3 pages.

Lonial et al., "Elotuzumab therapy for relapsed or refractory multiple myeloma," New England Journal of Medicine, Aug. 13, 2015, 373(7):621-31.

Lonial et al., "Phase II study of daratumumab (DARA) monotherapy in patients with ≥ 3 lines of prior therapy or double refractory multiple myeloma (MM): 54767414MMY2002 (Sirius)," Journal of Clinical Oncology, Jun. 2015, 33(18), abstract only, 2 pages.

Ma et al., "Chimeric antigen receptor T cell targeting B cell maturation antigen immunotherapy is promising for multiple myeloma," Annals of Hematology, Apr. 5, 2019, 98(4):813-22.

McNamara et al., American Society of Hematology 55th Annual Meeting and Exposition, New Orleans, Louisiana, USA, Drugs of Today, Dec. 2013, 49(12), abstract only, 1 page.

"Morgan and Schambach, Engineering CAR-T Cells for Improved Function Against Solid Tumors, Frontiers in Immunology, 2018, pp. 1-11".

Nicolson et al., "The interaction of Ricinus communis agglutinin with normal and tumor cell surfaces," Biochimica et Biophysica Acta (BBA)-Biomembranes, May 9, 1972, 266(2):543-547.

Olsnes et al., "Mechanism of action of the toxic lectins abrin and ricin," Nature, Jun. 1974, 249(5458):627-631.

Olsnes et al., "Ricin and ricinus agglutinin, toxic lectins from castor bean," Methods in Enzymology, Jan. 1, 1978, 50:330-335.

Phillips et al., "Targeting HER2-positive breast cancer with trastuzumab-DM1, an antibody-cytotoxic drug conjugate," Cancer Research, Nov. 15, 2008, 68(22):9280-9290.

Plesner et al., "Daratumumab for the treatment of multiple myeloma," Frontiers in Immunology, Jun. 4, 2019, 9:1228, 7 pages.

Porter et al., "Chimeric antigen receptor-modified T cells in chronic lymphoid leukemia," New England Journal of Medicine, Aug. 25, 2011, 365:725-733.

Rajkumar et al., "Combination therapy with lenalidomide plus dexamethasone (Rev/Dex) for newly diagnosed myeloma," Blood, Dec. 15, 2005, 106(13):4050-3.

Rathoreet al., "Overproduction of fungal ribotoxin α-sarcin in *Escherichia coli*: generation of an active immunotoxin," Gene, Jan. 1, 1997, 190(1): 31-35.

Rennert et al., "A soluble form of B cell maturation antigen, a receptor for the tumor necrosis factor family member APRIL, inhibits tumor cell growth," Journal of Experimental Medicine, Apr. 4, 2000, 192(11):1677-1684.

Sbah et al., "B-cell maturation antigen (BCMA) in multiple myeloma: rationale for targeting and current therapeutic approaches," Leukemia, Apr. 2020, 34(4):985-1005.

Smith et al., "Development and evaluation of an optimal human single-chain variable fragment-derived BCMA-targeted CAR T cell vector," Molecular Therapy, Jun. 6, 2018, 26(6):1447-56, 38 pages.

Sommer et al., "ALLO-715, an allogeneic BCMA CAR T therapy possessing an off-switch for the treatment of multiple myeloma," Blood, Nov. 29, 2018, 132(Supplement 1): 591, 3 pages.

Sridhar and Petrocca, "Regional Delivery of Chimeric Antigen Receptor (CAR) T-Cells for Cancer Therapy," Cancers, 2017, pp. 1-10.

Stirpe et al., "Ribosome-inactivating proteins from plants: present status and future prospects," Bio/Technology, Apr. 1992, 10(4):405-12.

Suzuki et al., "Engineering receptor-mediated cytotoxicity into human ribonucleases by steric blockade of inhibitor interaction," Nature Biotechnology, Mar. 1999, 17(3):265-270.

Thompson et al., "BAFF binds to the tumor necrosis factor receptor-like molecule B cell maturation antigen and is important for maintaining the peripheral B cell population," The Journal of Experimental Medicine, Jul. 3, 2000, 192(1):129-136.

Thorpe et al., "New coupling agents for the synthesis of immunotoxins containing a hindered disulfide bond with improved stability in vivo," Cancer Research, Nov. 15, 1987, 47(22):5924-5931.

Wawrzynczak et al., "Methods for preparing immunotoxins: effect of the linkage on activity and stability," Immunoconjugates: Antibody Conjugates in Radioimaging and Therapy of Cancer, 1987, 28-55.

Yu et al., "The biosynthetic gene cluster of the maytansinoid antitumor agent ansamitocin from Actinosynnema pretiosum," Proceedings of the National Academy of Sciences, Jun. 11, 2002, 99(12):7968-7973.

Yvon et al., "Immunotherapy of metastatic melanoma using genetically engineered GD2-specific T cells," Clinical Cancer Research, Sep. 15, 2009, 15(18):5852-5860.

Zhao et al., "A herceptin-based chimeric antigen receptor with modified signaling domains leads to enhanced survival of transduced T lymphocytes and antitumor activity," The Journal of Immunology, Nov. 1, 2009, 183(9):5563-5574.

Zhao et al., "Primary human lymphocytes transduced with NY-ESO-1 antigen-specific TCR genes recognize and kill diverse human tumor cell lines," The Journal of Immunology, Apr. 1, 2005, 174(7):4415-4423.

A
B
C
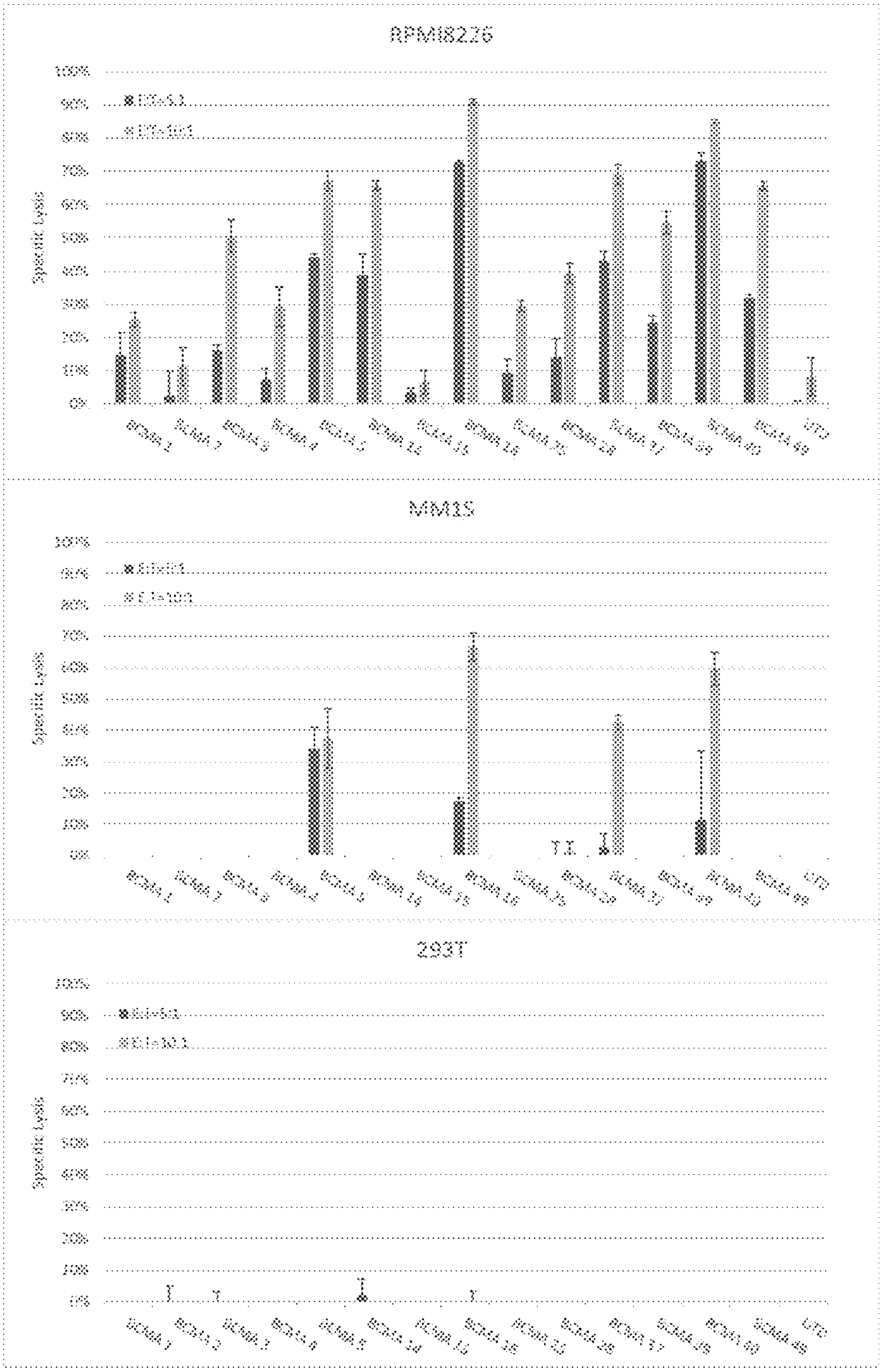
FIGS. 3A-C

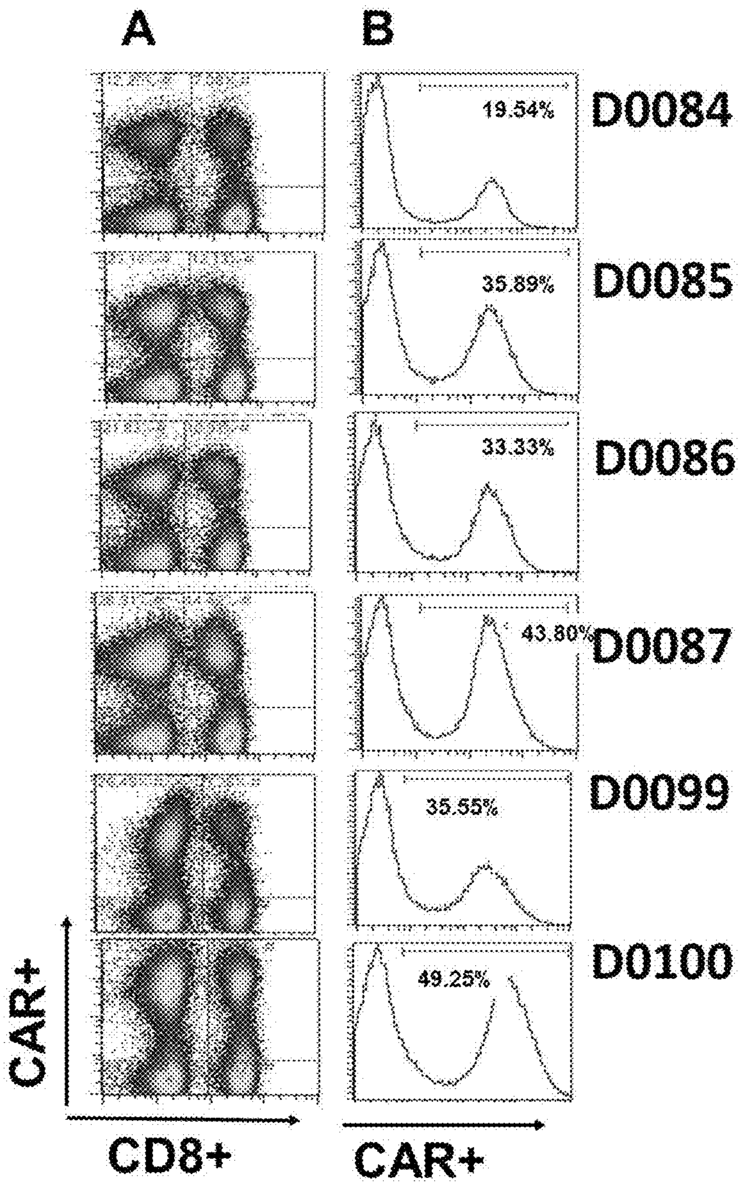
FIGS. 4A-B

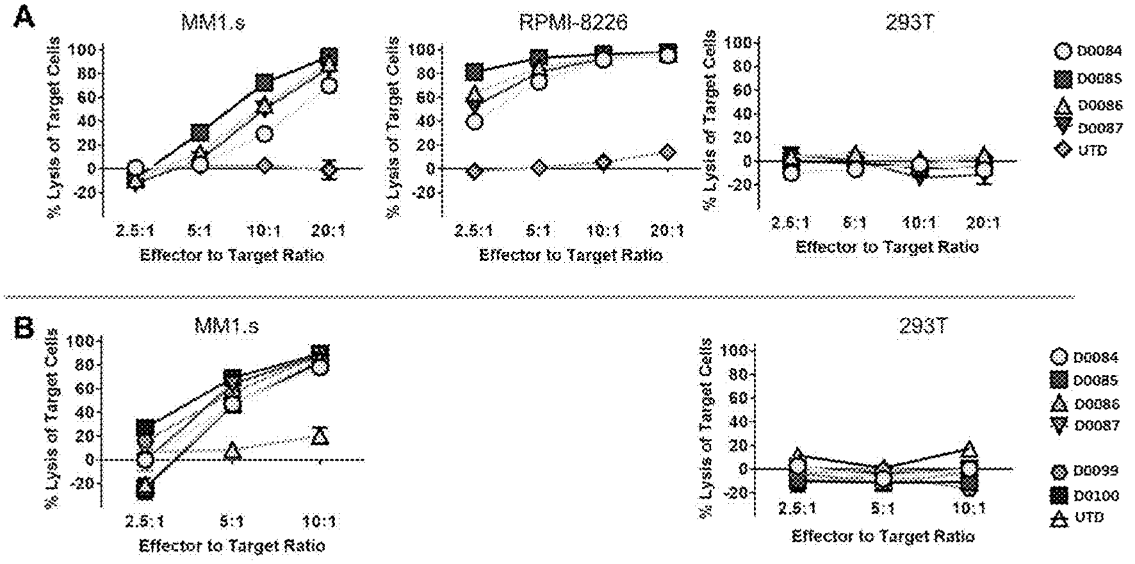
FIGS. 5A-B

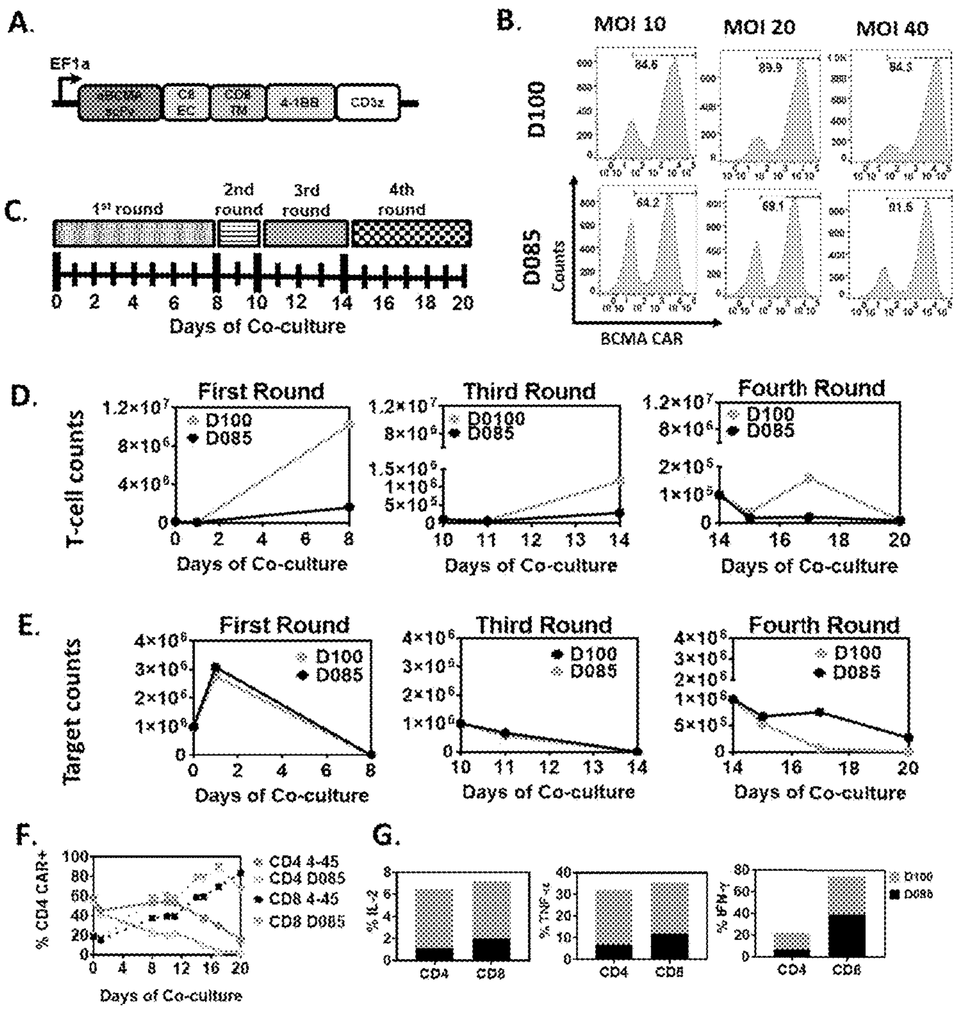
FIGS. 6A-G

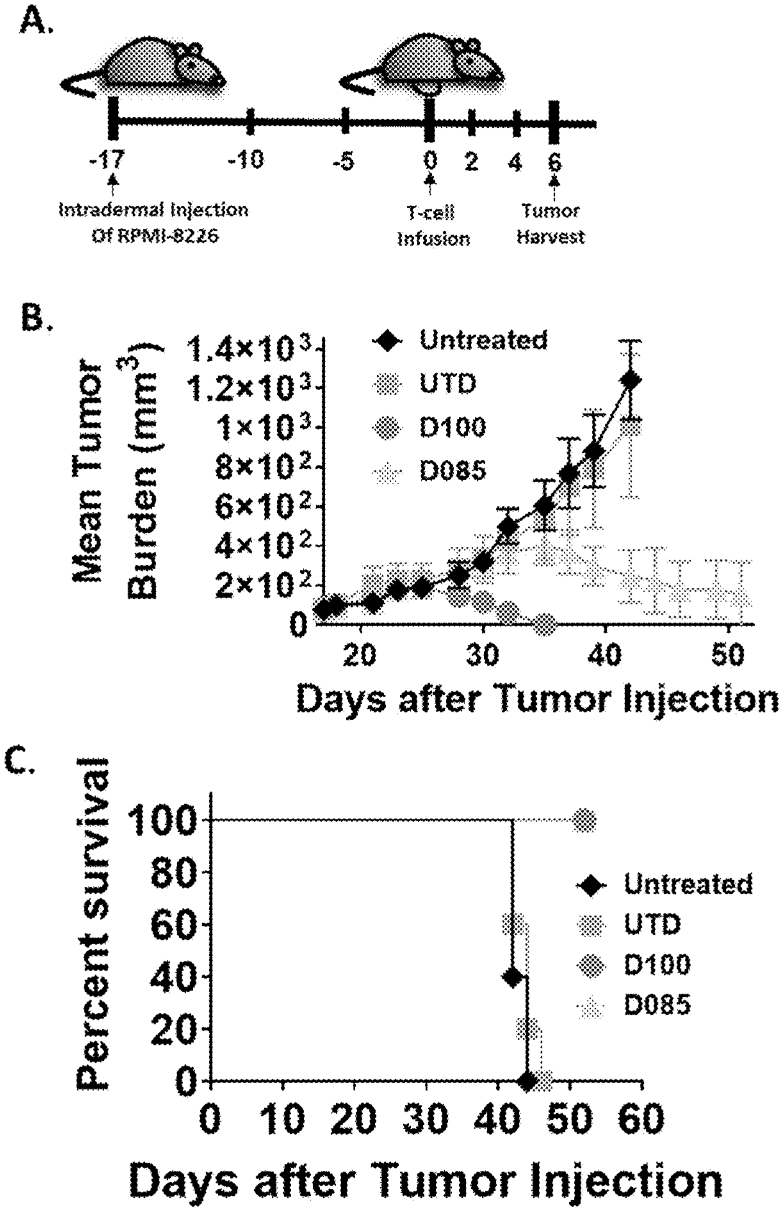
FIGS. 7A-C

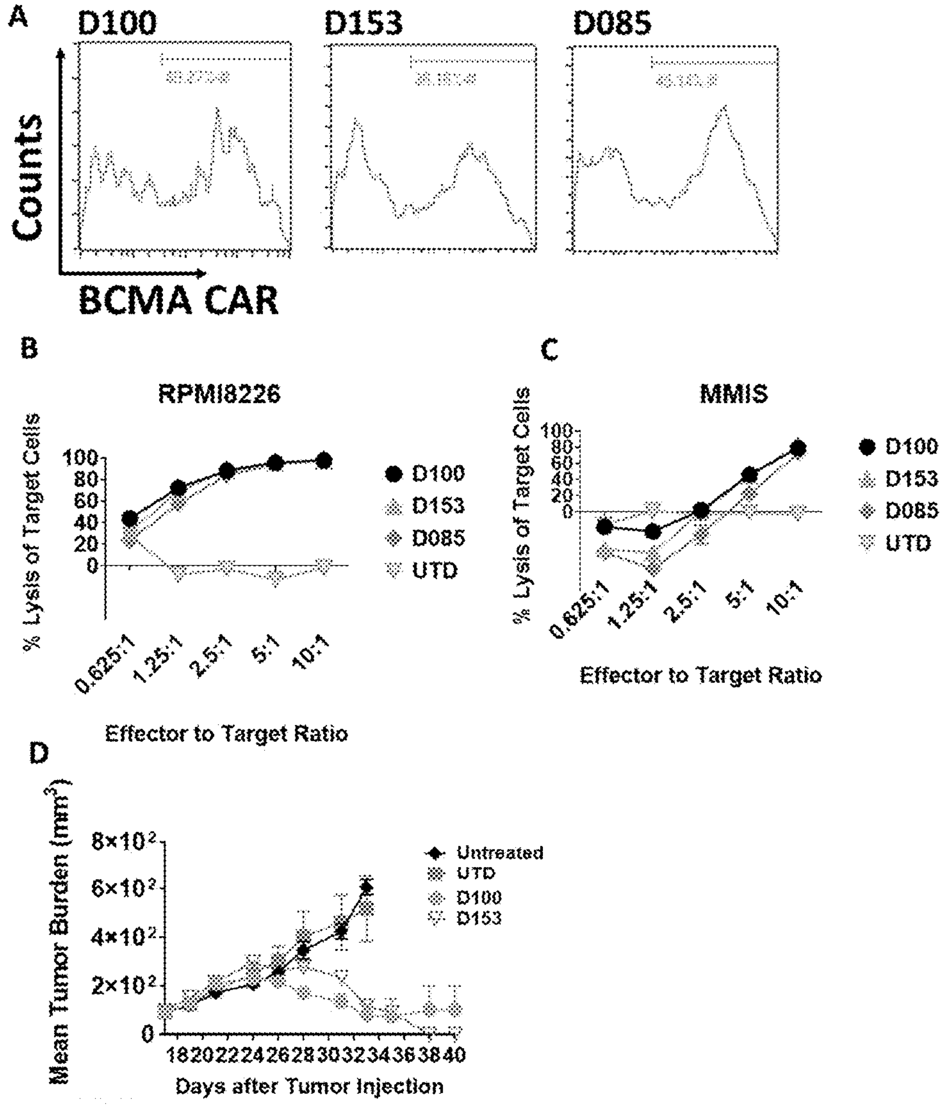
FIGS. 8A-D

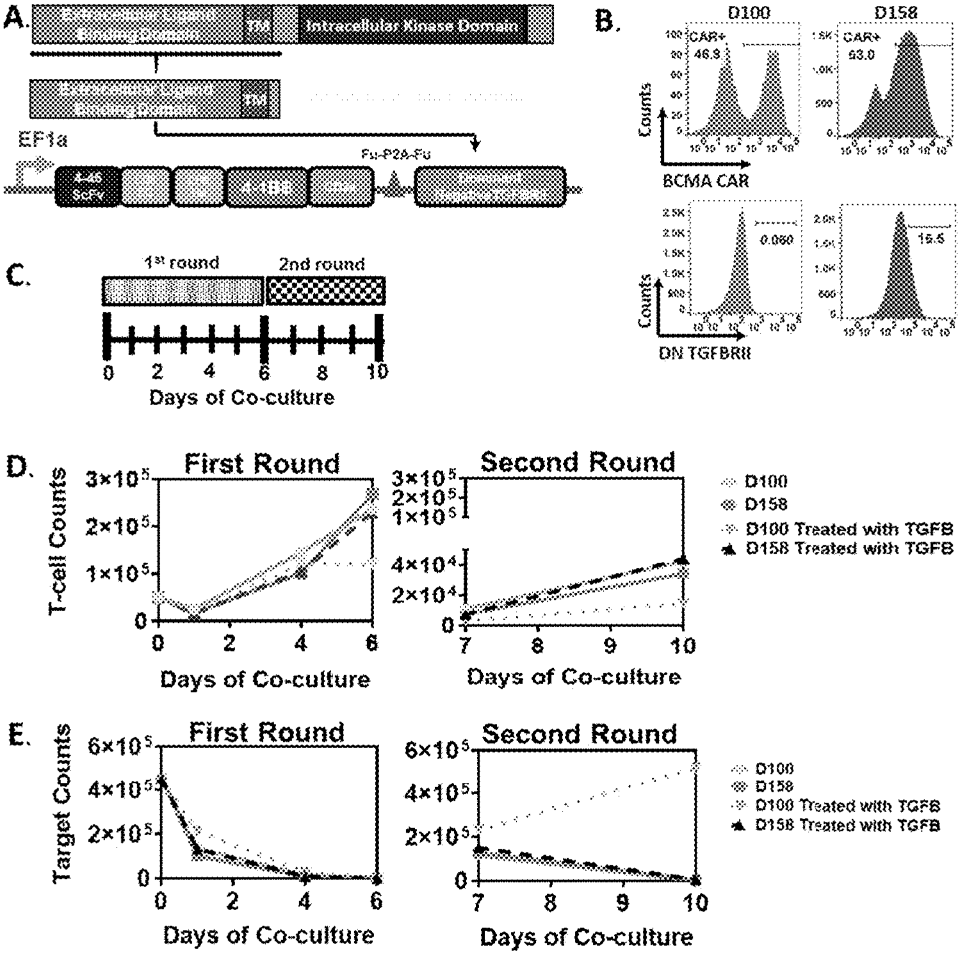
FIGS. 9A-E

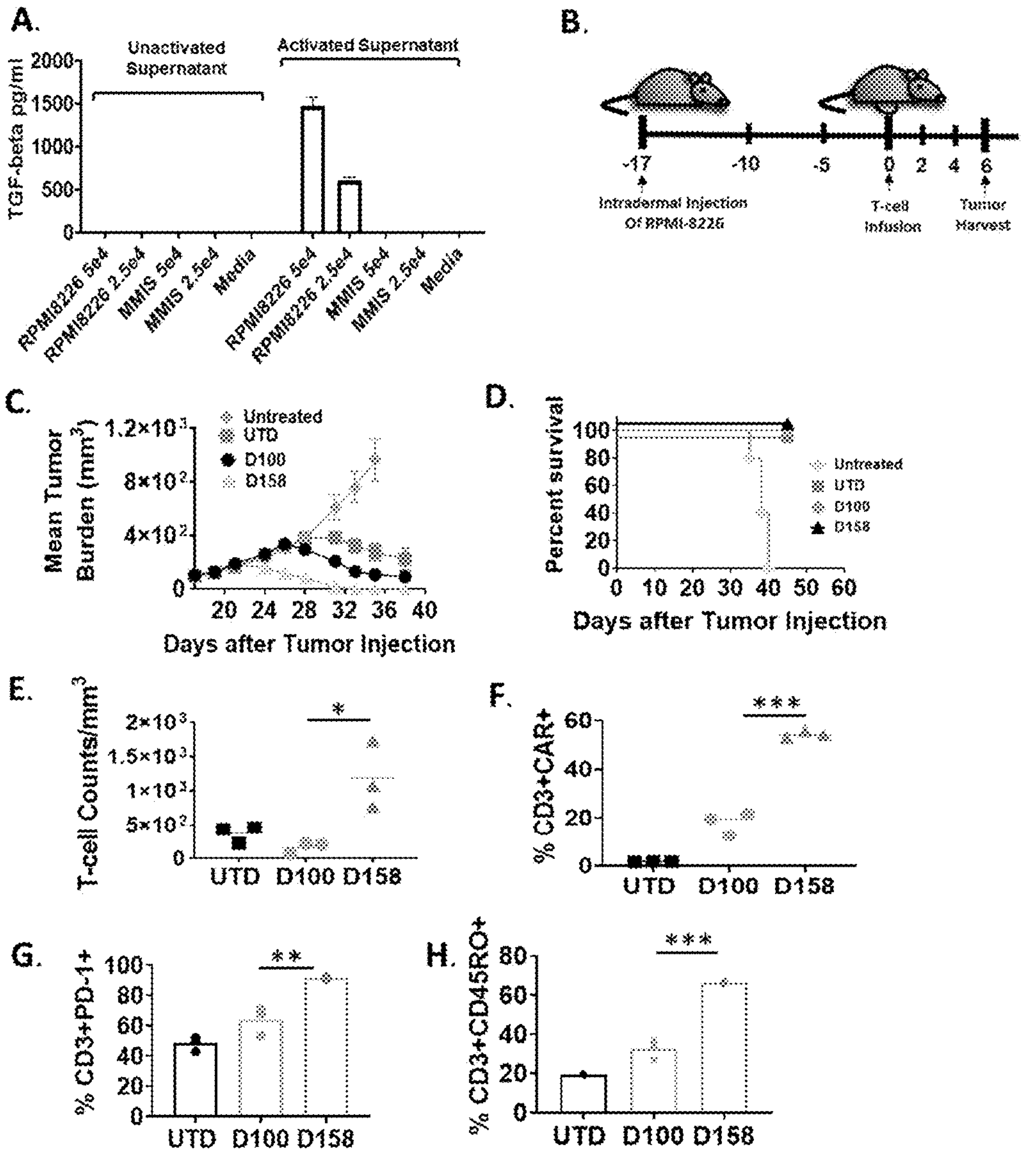
FIGS. 10A-H

SEQUENCE LISTING

```
<160> NUMBER OF SEQ ID NOS: 110

<210> SEQ ID NO 1
<211> LENGTH: 727
<212> TYPE: DNA
<213> ORGANISM: Artificial
<220> FEATURE:
<223> OTHER INFORMATION: BCMA ScFv binder MTB-1

<400> SEQUENCE: 1

gaggtgcagc tggtggagac tgggggaggc gtggtccagc ctgggggtc cctgagactc      60

tcctgtgcag cgtctggatt caccttcagt agctatggca tgcactgggt ccgccaggct    120
```

```
ccaggcaagg ggctggagtg ggtggcattt atacggtatg atggaagtaa taaatactat    180

gcagactccg tgaagggccg attcaccatc tccagagaca attccaagaa cacgctgtat    240

ctgcaaatga acagcctgag agctgatgac acggctgtgt attactgtgc gagagattgg    300

gagggctatg agggaggggt gaaatggggc cagggcaccc tggtcaccgt ctcctcagga    360

ggtggcggat ctggtggagg cggtagcggt ggtggcggat cccgaaattg tgctgactca    420

gtctccatcc tccctgtctg catctgtagg agacagagtc accatcactt gccaggcgag    480

tcaggacatt agcaactatt taaattggta tcagcagaaa ccagggaaag cccctaagct    540

cctgatctac gatgcatcca atttggaaac aggggtccca tcaaggttca gtggaagtgg    600

atctgggaca gattttactt tcaccatcag cagcctgcag cctgaagata ttgcaacata    660

ttactgtcaa cagtatgata atctctcgta cacttttggc caggggacca agctggagat    720

caaacgt                                                              727


<210> SEQ ID NO 2
<211> LENGTH: 242
<212> TYPE: PRT
<213> ORGANISM: Artificial
<220> FEATURE:
<223> OTHER INFORMATION: BCMA ScFv binder MTB-1

<400> SEQUENCE: 2

Glu Val Gln Leu Val Glu Thr Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Asp Trp Glu Gly Tyr Glu Gly Gly Val Lys Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Glu Ile Val Leu Thr Gln Ser Pro Ser Ser
    130                 135                 140

Leu Ser Ala Ser Val Gly Asp Arg Val Thr Ile Thr Cys Gln Ala Ser
145                 150                 155                 160

Gln Asp Ile Ser Asn Tyr Leu Asn Trp Tyr Gln Gln Lys Pro Gly Lys
                165                 170                 175

Ala Pro Lys Leu Leu Ile Tyr Asp Ala Ser Asn Leu Glu Thr Gly Val
            180                 185                 190

Pro Ser Arg Phe Ser Gly Ser Gly Ser Gly Thr Asp Phe Thr Phe Thr
        195                 200                 205

Ile Ser Ser Leu Gln Pro Glu Asp Ile Ala Thr Tyr Tyr Cys Gln Gln
    210                 215                 220

Tyr Asp Asn Leu Ser Tyr Thr Phe Gly Gln Gly Thr Lys Leu Glu Ile
225                 230                 235                 240

Lys Arg
```

-continued

<210> SEQ ID NO 3
<211> LENGTH: 729
<212> TYPE: DNA
<213> ORGANISM: Artificial
<220> FEATURE:
<223> OTHER INFORMATION: BCMA ScFv binder MTB-2

<400> SEQUENCE: 3

```
gaggtgcagc tggtgcaatc tgggggaggc ttggtccagc ctggggggtc cctgagactc     60

tcctgtgcag cctctggatt cacctttagt agctattgga tgagctgggt ccgccaggct    120

ccagggaagg ggctggagtg ggtctcaggt attaatggga gtggcgatag aacatattac    180

gcagactccg tgaagggccg gttcaccatc tccagagaca attccaagaa cacgctctat    240

ctgcaaatga acagcctgag agccgaagac acggccgtat attactgtgc gaactataat    300

tacgatgata atagtggtta tggcctgggc cagggaaccc tggtcaccgt ctcctcagga    360

ggtggcggat ctggtggagg cggtagcggt ggtggcggat cccagtctgt gctgactcag    420

ccaccctcgg tgtcagtggc cccaggaaag acggccagga ttacctgtgg gggaaacaac    480

attggaagta aaagtgtgca ctggtaccag cagaagccag gccaggcccc tgtgctggtc    540

atctatgatg atagcgaccg gccctcaggg atccctgagc gattctctgg ctccaactct    600

gggaacacag ccaccctgac catcagcagg gtcgaagccg gggatgaagc cgactattac    660

tgtcaggtgt gggacagtag tagtgatcat tgggtgttcg gcggagggac caaggtcacc    720

gtcctaggt                                                            729
```

<210> SEQ ID NO 4
<211> LENGTH: 243
<212> TYPE: PRT
<213> ORGANISM: Artificial
<220> FEATURE:
<223> OTHER INFORMATION: BCMA ScFv binder MTB-2

<400> SEQUENCE: 4

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Gly Ile Asn Gly Ser Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Tyr Asn Tyr Asp Asp Asn Ser Gly Tyr Gly Leu Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gln Ser Val Leu Thr Gln Pro Pro Ser Val
    130                 135                 140

Ser Val Ala Pro Gly Lys Thr Ala Arg Ile Thr Cys Gly Gly Asn Asn
145                 150                 155                 160

Ile Gly Ser Lys Ser Val His Trp Tyr Gln Gln Lys Pro Gly Gln Ala
                165                 170                 175
```

-continued

```
Pro Val Leu Val Ile Tyr Asp Asp Ser Asp Arg Pro Ser Gly Ile Pro
            180                 185                 190

Glu Arg Phe Ser Gly Ser Asn Ser Gly Asn Thr Ala Thr Leu Thr Ile
        195                 200                 205

Ser Arg Val Glu Ala Gly Asp Glu Ala Asp Tyr Tyr Cys Gln Val Trp
    210                 215                 220

Asp Ser Ser Ser Asp His Trp Val Phe Gly Gly Gly Thr Lys Val Thr
225                 230                 235                 240

Val Leu Gly


<210> SEQ ID NO 5
<211> LENGTH: 729
<212> TYPE: DNA
<213> ORGANISM: Artificial
<220> FEATURE:
<223> OTHER INFORMATION: BCMA ScFv binder MTB-3

<400> SEQUENCE: 5

gaggtgcagc tggtggagtc cgggggaggc gtggtccagc ctgggggtc cctgagactc      60

tcctgtgcag catctggatt caccttcagt agctatggca tgcactgggt ccgccaggct     120

ccaggcaagg ggctggagtg ggtggcattt atacggtatg atggaagtaa taaatactac     180

gcagactccg tgaagggccg attcaccatc tccagagaca attccaagaa cacgctgtat     240

ctgcaaatga acagcctgag agctgaggac acggctgtgt attactgtgc gaaagacgac     300

tacggtggta actccgaggg tgactactgg ggccagggaa ccctggtcac cgtctcctca     360

ggaggtggcg gatctggtgg aggcggtagc ggtggtggcg gatccgaaat tgtgttgaca     420

cagtctccag ccaccctgtc tgtgtctcta ggagagagag ccaccctctc ctgcagggcc     480

agtcagagtg ttagcaacag cttagcctgg tatcagcaga aacctggcca ggctcccagg     540

ctcctcatct atgatgcatc cacgagggcc actggcatcc cagccaggtt cagtggcagt     600

gggtctggga cagagttcac tctcaccatc agcagtctgc agcctgaaga ttttgcaact     660

tatttctgtc aacagactta cagtcccccg atcaccttcg gccaagggac acgactggag     720

attaaacga                                                             729


<210> SEQ ID NO 6
<211> LENGTH: 243
<212> TYPE: PRT
<213> ORGANISM: Artificial
<220> FEATURE:
<223> OTHER INFORMATION: BCMA ScFv binder MTB-3

<400> SEQUENCE: 6

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asp Tyr Gly Gly Asn Ser Glu Gly Asp Tyr Trp Gly Gln
```

-continued

```
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Leu Thr Gln Ser Pro Ala
    130                 135                 140

Thr Leu Ser Val Ser Leu Gly Glu Arg Ala Thr Leu Ser Cys Arg Ala
145                 150                 155                 160

Ser Gln Ser Val Ser Asn Ser Leu Ala Trp Tyr Gln Gln Lys Pro Gly
                165                 170                 175

Gln Ala Pro Arg Leu Leu Ile Tyr Asp Ala Ser Thr Arg Ala Thr Gly
            180                 185                 190

Ile Pro Ala Arg Phe Ser Gly Ser Gly Ser Gly Thr Glu Phe Thr Leu
        195                 200                 205

Thr Ile Ser Ser Leu Gln Pro Glu Asp Phe Ala Thr Tyr Phe Cys Gln
    210                 215                 220

Gln Thr Tyr Ser Pro Pro Ile Thr Phe Gly Gln Gly Thr Arg Leu Glu
225                 230                 235                 240

Ile Lys Arg
```

<210> SEQ ID NO 7
<211> LENGTH: 726
<212> TYPE: DNA
<213> ORGANISM: Artificial
<220> FEATURE:
<223> OTHER INFORMATION: BCMA ScFv binder MTB-4

<400> SEQUENCE: 7

```
gaggtgcagc tggtggagac tgggggaggc gtggtccagc ctgggggggtc cctgagactc     60

tcctgtgcag cgtctggatt caccttcagt agctatggca tgcactgggt ccgccaggct    120

ccaggcaagg ggctggagtg ggtggcattt atacggtatg atggaagtaa taaatactat    180

gcagactccg tgaagggccg attcaccatc tccagagaca attccaagaa cacgctgtat    240

ctgcaaatga acagcctgag agctgatgac acggctgtgt attactgtgc gagagattgg    300

gagggctatg agggaggggt gaaatggggc cagggcaccc tggtcaccgt ctcctcagga    360

ggtggcggat ctggtggagg cggtagcggt ggtggcggat ccgaaattgt gctgactcag    420

tctccatcct ccctgtctgc atctgtagga gacagagtca ccatcacttg ccaggcgagt    480

caggacatta gcaactattt aaattggtat cagcagaaac cagggaaagc ccctaagctc    540

ctgatctacg atgcatccaa tttggaaaca ggggtcccat caaggttcag tggaagtgga    600

tctgggacag attttacttt caccatcagc agcctgcagc ctgaagatat tgcaacatat    660

tactgtcaac agtatgataa tctctcgtac acttttggcc aggggaccaa gctggagatc    720

aaacgt                                                               726
```

<210> SEQ ID NO 8
<211> LENGTH: 242
<212> TYPE: PRT
<213> ORGANISM: Artificial
<220> FEATURE:
<223> OTHER INFORMATION: BCMA ScFv binder MTB-4

<400> SEQUENCE: 8

```
Glu Val Gln Leu Val Glu Thr Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30
```

-continued

```
Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Asp Trp Glu Gly Tyr Glu Gly Gly Val Lys Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Glu Ile Val Leu Thr Gln Ser Pro Ser Ser
    130                 135                 140

Leu Ser Ala Ser Val Gly Asp Arg Val Thr Ile Thr Cys Gln Ala Ser
145                 150                 155                 160

Gln Asp Ile Ser Asn Tyr Leu Asn Trp Tyr Gln Gln Lys Pro Gly Lys
                165                 170                 175

Ala Pro Lys Leu Leu Ile Tyr Asp Ala Ser Asn Leu Glu Thr Gly Val
            180                 185                 190

Pro Ser Arg Phe Ser Gly Ser Gly Ser Gly Thr Asp Phe Thr Phe Thr
        195                 200                 205

Ile Ser Ser Leu Gln Pro Glu Asp Ile Ala Thr Tyr Tyr Cys Gln Gln
    210                 215                 220

Tyr Asp Asn Leu Ser Tyr Thr Phe Gly Gln Gly Thr Lys Leu Glu Ile
225                 230                 235                 240

Lys Arg


<210> SEQ ID NO 9
<211> LENGTH: 753
<212> TYPE: DNA
<213> ORGANISM: Artificial
<220> FEATURE:
<223> OTHER INFORMATION: BCMA ScFv binder MB-5

<400> SEQUENCE: 9

gaggtccagc tggtgcagtc tgggggaggc gtggtccagc ctgggggggtc cctgagactc      60

tcctgtgcag cgtctggatt caccttcagt agctatggca tgcactgggt ccgccaggct     120

ccaggcaagg ggctggagtg ggtggcattt atacggtatg atggaagtaa taaatactat     180

gcagactccg tgaagggccg attcaccatc tccagagaca attccaagaa cacgctgtat     240

ctgcaaatga acagcctgag agctgaggac acggctgtgt attactgtgc gagagattgg     300

gccggggatt gtactaatgg ccaatgcggc gtctactggg gccagggaac cctggtcacc     360

gtctcctcag gaggtggcgg atctggtgga ggcggtagcg gtggtggcgg atccgaaatt     420

gtgttgacgc agtctccact ctccctgccc gtcacccctg gagagccggc ctccatctcc     480

tgcaggtcta gtcagagcct cctgcatagt aatggataca actatttgga ttggtacctg     540

cagaagccag ggcagtctcc acagctcctg atctatttgg gttctaatcg ggcctccggg     600

gtccctgaca ggttcagtgg cagtggatca ggcacagatt ttacactgaa aatcagcaga     660

gtggaggctg aggatgttgg ggtttattac tgcatgcaag ctctacaaac tccgtacact     720

tttggccagg ggaccaagct ggagatcaaa cgt                                  753
```

<210> SEQ ID NO 10
<211> LENGTH: 251
<212> TYPE: PRT
<213> ORGANISM: Artificial
<220> FEATURE:
<223> OTHER INFORMATION: BCMA ScFv binder MTB-5

<400> SEQUENCE: 10

```
Glu Val Gln Leu Val Gln Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Ala Gly Asp Cys Thr Asn Gly Gln Cys Gly Val Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Glu Ile Val Leu Thr Gln
    130                 135                 140

Ser Pro Leu Ser Leu Pro Val Thr Pro Gly Glu Pro Ala Ser Ile Ser
145                 150                 155                 160

Cys Arg Ser Ser Gln Ser Leu Leu His Ser Asn Gly Tyr Asn Tyr Leu
                165                 170                 175

Asp Trp Tyr Leu Gln Lys Pro Gly Gln Ser Pro Gln Leu Leu Ile Tyr
            180                 185                 190

Leu Gly Ser Asn Arg Ala Ser Gly Val Pro Asp Arg Phe Ser Gly Ser
        195                 200                 205

Gly Ser Gly Thr Asp Phe Thr Leu Lys Ile Ser Arg Val Glu Ala Glu
    210                 215                 220

Asp Val Gly Val Tyr Tyr Cys Met Gln Ala Leu Gln Thr Pro Tyr Thr
225                 230                 235                 240

Phe Gly Gln Gly Thr Lys Leu Glu Ile Lys Arg
                245                 250
```

<210> SEQ ID NO 11
<211> LENGTH: 729
<212> TYPE: DNA
<213> ORGANISM: Artificial
<220> FEATURE:
<223> OTHER INFORMATION: BCMA ScFv binder MTB-14

<400> SEQUENCE: 11

```
gaggtgcagc tggtggagtc tgggggaggc gtggtccagc ctgggaggtc cctgagactc      60

tcctgtgcag cgtctggatt caccttcagt agctatggca tgcactgggt ccgccaggct     120

ccaggcaagg ggctggagtg ggtggcattt atacggtatg atggaagtaa taaatactat     180

gcagactccg tgaagggccg attcaccatc tccagagaca attccaagaa cacgctgtat     240

ctgcaaatga acagcctgag agctgaggac acggctgtgt attactgtgt gagcgatgac     300

tacggtggta actccgggac tagctactgg ggccagggaa ccctggtcac cgtctcctca     360
```

-continued

```
ggaggtggcg gatctggtgg aggcggtagc ggtggtggcg gatccgacat ccagatgacc    420

cagtctccat cctccctgtc tgcatctgta ggagacagag tcaccatcac ttgccaggcg    480

agtcaggaca ttagcaacta tttaaattgg tatcagcaga agccagggaa agcccctaag    540

ctcctgatct acgatgcatc caatttggaa acaggggtcc catcaaggtt cagtggcagt    600

ggatctggga cagatttcac tctcaccatc agcagtctgc aacctgaaga ttttgcaact    660

tactactgtc aacagagtta cagtaccccc gtgacgttcg gcggagggac caagctgacc    720

gtcctaggt                                                             729


<210> SEQ ID NO 12
<211> LENGTH: 243
<212> TYPE: PRT
<213> ORGANISM: Artificial
<220> FEATURE:
<223> OTHER INFORMATION: BCMA ScFv binder MTB-14

<400> SEQUENCE: 12

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Ser Asp Asp Tyr Gly Gly Asn Ser Gly Thr Ser Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Gln Ala
145                 150                 155                 160

Ser Gln Asp Ile Ser Asn Tyr Leu Asn Trp Tyr Gln Gln Lys Pro Gly
                165                 170                 175

Lys Ala Pro Lys Leu Leu Ile Tyr Asp Ala Ser Asn Leu Glu Thr Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Ser Tyr Ser Thr Pro Val Thr Phe Gly Gly Gly Thr Lys Leu Thr
225                 230                 235                 240

Val Leu Gly


<210> SEQ ID NO 13
<211> LENGTH: 66
<212> TYPE: DNA
<213> ORGANISM: Artificial
<220> FEATURE:
<223> OTHER INFORMATION: leader/signal peptide sequence
```

```
<400> SEQUENCE: 13

atgctgctgc tggtgaccag cctgctgctg tgcgaactgc cgcatccggc gtttctgctg     60

attccg                                                                66


<210> SEQ ID NO 14
<211> LENGTH: 22
<212> TYPE: PRT
<213> ORGANISM: Artificial
<220> FEATURE:
<223> OTHER INFORMATION: leader/signal peptide sequence

<400> SEQUENCE: 14

Met Leu Leu Leu Val Thr Ser Leu Leu Leu Cys Glu Leu Pro His Pro
1               5                   10                  15

Ala Phe Leu Leu Ile Pro
            20


<210> SEQ ID NO 15
<211> LENGTH: 735
<212> TYPE: DNA
<213> ORGANISM: Artificial
<220> FEATURE:
<223> OTHER INFORMATION: BCMA ScFv binder MTB-15

<400> SEQUENCE: 15

caggtgcagc tggtggagac cgggggaggc gtggtccagc ctgggggtc cctgagactc     60

tcctgtgcag cgtctggatt caccttcagt agctatggca tgcactgggt ccgccaggct    120

ccaggcaagg ggctggagtg ggtggcattt atacggtatg atggaagtaa taaatactat    180

gcagactccg tgaagggccg attcaccatc tccagagaca attccaagaa cacgctgtat    240

ctgcaaatga acagcctgag agctgaggac acggctgtgt attactgtgc gaaagattgg    300

gattgtactg gtggtgtatg cccccttggg ggctggggcc agggaaccct ggtcaccgtc    360

tcctcaggag gtggcggatc tggtggaggc ggtagcggtg gtggcggatc cgacatccag    420

ttgacccagt ctccatcctc cctgtctgca tctgtaggag acagagtcac catcacttgc    480

cgggcaagtc agagcattag tggctattta aattggtatc agcagaaacc agggaaagcc    540

cctaagctcc tgatctatgc tgcatccagt ttgcaaagtg gggtcccatc aaggttcagt    600

ggcagtggat ctgggacaga gttcactctc accatcagca gtctgcagcc tgaagatttt    660

gcaacttatt tctgtcaaca gacttacagt ccccccgatca ccttcggcca agggacacga    720

ctggagatta aacga                                                     735


<210> SEQ ID NO 16
<211> LENGTH: 245
<212> TYPE: PRT
<213> ORGANISM: Artificial
<220> FEATURE:
<223> OTHER INFORMATION: BCMA ScFv binder MTB-15

<400> SEQUENCE: 16

Gln Val Gln Leu Val Glu Thr Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60
```

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Trp Asp Cys Thr Gly Gly Val Cys Pro Leu Gly Gly Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Asp Ile Gln Leu Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Ser Ile Ser Gly Tyr Leu Asn Trp Tyr Gln Gln Lys
                165                 170                 175

Pro Gly Lys Ala Pro Lys Leu Leu Ile Tyr Ala Ala Ser Ser Leu Gln
            180                 185                 190

Ser Gly Val Pro Ser Arg Phe Ser Gly Ser Gly Ser Gly Thr Glu Phe
        195                 200                 205

Thr Leu Thr Ile Ser Ser Leu Gln Pro Glu Asp Phe Ala Thr Tyr Phe
    210                 215                 220

Cys Gln Gln Thr Tyr Ser Pro Pro Ile Thr Phe Gly Gln Gly Thr Arg
225                 230                 235                 240

Leu Glu Ile Lys Arg
                245
```

<210> SEQ ID NO 17
<211> LENGTH: 729
<212> TYPE: DNA
<213> ORGANISM: Artificial
<220> FEATURE:
<223> OTHER INFORMATION: BCMA ScFv binder MTB-16

<400> SEQUENCE: 17

```
gaggtccagc tggtgcagtc tgggggaggc gtggtccagc ctgggggtc cctgagactc      60

tcctgtgcag cgtctggatt caccttcagt agctatggca tgcactgggt ccgccaggct    120

ccaggcaagg ggctggagtg ggtggcattt atacggtatg atggaagtaa taaatactac    180

gcagactccg tgaagggccg attcaccatc tccagagaca attccaagaa cacgctgtat    240

ctgcaaatga acagcctgag agctgaggac acggctgtgt attactgtgc gagagacctt    300

aatgactacg gtgacccgcc cccttactgg ggccagggaa ccctggtcac cgtctcctca    360

ggaggtggcg gatctggtgg aggcggtagc ggtggtggcg gatccgacat ccagatgacc    420

cagtctccat cctccctgtc tgcatctgta ggagacagag tcaccatcac ttgccgggca    480

agtcagagca ttagcagcta tttaaattgg tatcagcaga aaccagggaa agcccctaag    540

ctcctgatct acgatgcatc caatttggaa acaggggtct catcaaggtt cagtggcagt    600

ggatctggga cagagttcac tctcaccatc agcagtctgc agcctgaaga ttttgcaact    660

tatttctgtc aacagactta cagtcccccg atcaccttcg gccaagggac acgactggag    720

attaaacga                                                            729
```

<210> SEQ ID NO 18
<211> LENGTH: 243
<212> TYPE: PRT
<213> ORGANISM: Artificial
<220> FEATURE:

<223> OTHER INFORMATION: BCMA ScFv binder MTB-16

<400> SEQUENCE: 18

Glu Val Gln Leu Val Gln Ser Gly Gly Gly Val Val Gln Pro Gly Gly
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Phe Ile Arg Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Leu Asn Asp Tyr Gly Asp Pro Pro Pro Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Asp Ile Gln Met Thr Gln Ser Pro Ser
130 135 140

Ser Leu Ser Ala Ser Val Gly Asp Arg Val Thr Ile Thr Cys Arg Ala
145 150 155 160

Ser Gln Ser Ile Ser Ser Tyr Leu Asn Trp Tyr Gln Gln Lys Pro Gly
165 170 175

Lys Ala Pro Lys Leu Leu Ile Tyr Asp Ala Ser Asn Leu Glu Thr Gly
180 185 190

Val Ser Ser Arg Phe Ser Gly Ser Gly Ser Gly Thr Glu Phe Thr Leu
195 200 205

Thr Ile Ser Ser Leu Gln Pro Glu Asp Phe Ala Thr Tyr Phe Cys Gln
210 215 220

Gln Thr Tyr Ser Pro Pro Ile Thr Phe Gly Gln Gly Thr Arg Leu Glu
225 230 235 240

Ile Lys Arg

<210> SEQ ID NO 19
<211> LENGTH: 732
<212> TYPE: DNA
<213> ORGANISM: Artificial
<220> FEATURE:
<223> OTHER INFORMATION: BCMA ScFv binder MTB-25

<400> SEQUENCE: 19
gaggtgcagc tggtggagtc cgggggaggc ttagttcagc ctggggggtc cctgagactc 60
tcctgtgcag cgtctggatt caccttcagt agctatggca tgcactgggt ccgccaggct 120
ccaggcaagg ggctggagtg ggtggcattt atacggtatg atggaagtaa taaatactat 180
gcagactccg tgaagggccg attcaccatc tccagagaca attccaagaa cacgctgtat 240
ctgcaaatga acagcctgag agctgaggac acggctgtgt attactgtgc gagagatctc 300
gaaatgactg actactgggg ccagggaacc ctggtcaccg tctcctcagg aggtggcgga 360
tctggtggag gcggtagcgg tggtggcgga tccgaaattg tgctgactca gtctccactc 420
tccctgcccg tcacccctgg agagccggcc tccatatttt gtaggtctag tcagagtctc 480
ctgcatgaaa atggatacaa ctatttggat tggtacctgc agaagccagg gcagtctcca 540

-continued

```
cagctcctga tctatttggg ttctaatcgg gcctccgggg tccctgacag gttcagtggc    600

agtggatcag gcacagattt tacactgaaa atcagcagag tggaggctga ggatgttggg    660

gtttattact gcatgcaagc tctacaaacc cctcgaactt ttggccaggg gaccaagctg    720

gaaaccaaac gt                                                        732


<210> SEQ ID NO 20
<211> LENGTH: 244
<212> TYPE: PRT
<213> ORGANISM: Artificial
<220> FEATURE:
<223> OTHER INFORMATION: BCMA ScFv binder MTB-25

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Glu Met Thr Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Glu Ile Val Leu Thr Gln Ser Pro Leu Ser Leu Pro Val
    130                 135                 140

Thr Pro Gly Glu Pro Ala Ser Ile Phe Cys Arg Ser Ser Gln Ser Leu
145                 150                 155                 160

Leu His Glu Asn Gly Tyr Asn Tyr Leu Asp Trp Tyr Leu Gln Lys Pro
                165                 170                 175

Gly Gln Ser Pro Gln Leu Leu Ile Tyr Leu Gly Ser Asn Arg Ala Ser
            180                 185                 190

Gly Val Pro Asp Arg Phe Ser Gly Ser Gly Ser Gly Thr Asp Phe Thr
        195                 200                 205

Leu Lys Ile Ser Arg Val Glu Ala Glu Asp Val Gly Val Tyr Tyr Cys
    210                 215                 220

Met Gln Ala Leu Gln Thr Pro Arg Thr Phe Gly Gln Gly Thr Lys Leu
225                 230                 235                 240

Glu Thr Lys Arg


<210> SEQ ID NO 21
<211> LENGTH: 750
<212> TYPE: DNA
<213> ORGANISM: Artificial
<220> FEATURE:
<223> OTHER INFORMATION: BCMA ScFv binder MTB-28

<400> SEQUENCE: 21

caggtgcagc tggtggagtc tgggggaggc gtggtccagc ctgggggtc cctgagactc      60

tcctgtgcag cgtctggatt caccttcagt agctatggca tgcactgggt ccgccaggct    120
```

-continued

```
ccaggcaagg ggctggagtg ggtggcattt atacggtatg atggaagtaa taaatactat    180

gcagactccg tgaagggccg attcaccatc tccagagaca attccaagaa cacgctgtat    240

ctgcaaatga acagcctgag agctgaggac acggctgtgt attactgtgc gagagattcg    300

tatagcagca gcggggaccc ccgggcgttc gacccctggg gccagggaac cctggtcacc    360

gtctcctcag gaggtggcgg atctggtgga ggcggtagcg gtggtggcgg atccaatttt    420

atgctgactc agccccactc tgtgtcggag tctccgggga agacggtaac catctcctgc    480

accggcagca gtggcagcat tgccagcaac tatgtgcagt ggtaccagca gcgcccgggc    540

agtgccccct ccactgtcat ctttgaggat aaccaaagac cctctggggt ccctggtcgg    600

ttctctggct ccgtcgacag gtcctccaac tctgcctccc tcaccatctc tggactgaag    660

actgaggacg aggctgacta ctattgtcag tcttatgata gcaacaatcg ggtctgttc     720

ggcggaggga ccaaggtcac cgtcctaggt                                     750
```

```
<210> SEQ ID NO 22
<211> LENGTH: 250
<212> TYPE: PRT
<213> ORGANISM: Artificial
<220> FEATURE:
<223> OTHER INFORMATION: BCMA ScFv binder MTB-28

<400> SEQUENCE: 22

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Tyr Ser Ser Ser Gly Asp Pro Arg Ala Phe Asp Pro
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Asn Phe Met Leu Thr Gln
    130                 135                 140

Pro His Ser Val Ser Glu Ser Pro Gly Lys Thr Val Thr Ile Ser Cys
145                 150                 155                 160

Thr Gly Ser Ser Gly Ser Ile Ala Ser Asn Tyr Val Gln Trp Tyr Gln
                165                 170                 175

Gln Arg Pro Gly Ser Ala Pro Ser Thr Val Ile Phe Glu Asp Asn Gln
            180                 185                 190

Arg Pro Ser Gly Val Pro Gly Arg Phe Ser Gly Ser Val Asp Arg Ser
        195                 200                 205

Ser Asn Ser Ala Ser Leu Thr Ile Ser Gly Leu Lys Thr Glu Asp Glu
    210                 215                 220

Ala Asp Tyr Tyr Cys Gln Ser Tyr Asp Ser Asn Asn Arg Gly Leu Phe
225                 230                 235                 240

Gly Gly Gly Thr Lys Val Thr Val Leu Gly
                245                 250
```

<210> SEQ ID NO 23
<211> LENGTH: 732
<212> TYPE: DNA
<213> ORGANISM: Artificial
<220> FEATURE:
<223> OTHER INFORMATION: BCMA ScFv binder MTB-37

<400> SEQUENCE: 23

```
gaggtgcagc tggtggagtc tgggggaggc ttggtcaagc ctggagggtc cctgagactc     60

tcctgtgcag cgtctggatt caccttcagt agctatggca tgcactgggt ccgccaggct    120

ccaggcaagg ggctggagtg ggtggcattt atacggtatg atggaagtaa taaatactat    180

gcagactccg tgaagggccg attcaccatc tccagagaca attccaagaa cacgctgtat    240

ctgcaaatga acagcctgag agctgaggac acggctgtgt attactgtgc gaaagattgg    300

gaatatagtg gctacgatgc ccacccgggg tggggccagg gaaccctggt caccgtctcc    360

tcaggaggtg gcggatctgg tggaggcggt agcggtggtg gcggatccga catccagttg    420

acccagtctc catcctccct gtctgcatct gtaggagaca gagtcaccat cacttgccgg    480

gcaagtcagg gcattagcag tgctttagcc tggtatcagc agaaaccagg gaaagctcct    540

aagctcctga tctatgatgc ctccagtttg gaaagtgggg tcccatcaag gttcagtggc    600

agtggatctg ggacagagtt cactctcacc atcagcagtc tgcagcctga agattttgca    660

acttatttct gtcaacagac ttacagtccc ccgatcacct tcggccaagg gacacgactg    720

gagattaaac ga                                                        732
```

<210> SEQ ID NO 24
<211> LENGTH: 244
<212> TYPE: PRT
<213> ORGANISM: Artificial
<220> FEATURE:
<223> OTHER INFORMATION: BCMA ScFv binder MTB-37

<400> SEQUENCE: 24

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Trp Glu Tyr Ser Gly Tyr Asp Ala His Pro Gly Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Asp Ile Gln Leu Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Gly Ile Ser Ser Ala Leu Ala Trp Tyr Gln Gln Lys Pro
                165                 170                 175
```

-continued

```
Gly Lys Ala Pro Lys Leu Leu Ile Tyr Asp Ala Ser Ser Leu Glu Ser
            180                 185                 190

Gly Val Pro Ser Arg Phe Ser Gly Ser Gly Ser Gly Thr Glu Phe Thr
        195                 200                 205

Leu Thr Ile Ser Ser Leu Gln Pro Glu Asp Phe Ala Thr Tyr Phe Cys
    210                 215                 220

Gln Gln Thr Tyr Ser Pro Pro Ile Thr Phe Gly Gln Gly Thr Arg Leu
225                 230                 235                 240

Glu Ile Lys Arg


<210> SEQ ID NO 25
<211> LENGTH: 729
<212> TYPE: DNA
<213> ORGANISM: Artificial
<220> FEATURE:
<223> OTHER INFORMATION: BCMA ScFv binder MTB-39

<400> SEQUENCE: 25

gaggtgcagc tggtggagtc tgggggaggc gtggtccagc ctgggggggtc cctgagactc      60

tcctgtgcag cgtctggatt caccttcagt ggctatggca tgcactgggt ccgccaggct     120

ccaggcaagg ggctggagtg ggtggcattt atacggtatg atggaagtaa taaatactat     180

gcagactccg tgaagggccg attcaccatc tccagagaca attccaagaa cacgctgtat     240

ctgcaaatga acagcctgag agctgaggac acggctgtgt attactgtgc gagagatggg     300

gctcggaatg attactgggg ccagggcacc ctggtcaccg tctcctcagg aggtggcgga     360

tctggtggag gcggtagcgg tggtggcgga tccaatttta tgctgactca gccccactct     420

gtgtcggagt ctccggggaa gacggtaacc atctcctgca cccgcagcag tggcagcatt     480

gccagcaact atgtgcagtg gtaccagcag cgcccgggca gtgcccccac cactgtgatc     540

tatgaggata accaaagacc ctctggggtc cctgatcggt tctctggctc catcgacagc     600

tcctccaact ctgcctccct caccatctct ggactgaaga ctgaggacga ggctgactac     660

tactgtcaga cttatgatga caacaatcat gtcattttcg gcggagggac ccagctcacc     720

gttttaggt                                                              729


<210> SEQ ID NO 26
<211> LENGTH: 243
<212> TYPE: PRT
<213> ORGANISM: Artificial
<220> FEATURE:
<223> OTHER INFORMATION: BCMA ScFv binder MTB-39

<400> SEQUENCE: 26

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Asp Gly Ala Arg Asn Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Asn Phe Met Leu Thr Gln Pro His Ser Val Ser Glu Ser
    130                 135                 140

Pro Gly Lys Thr Val Thr Ile Ser Cys Thr Arg Ser Ser Gly Ser Ile
145                 150                 155                 160

Ala Ser Asn Tyr Val Gln Trp Tyr Gln Gln Arg Pro Gly Ser Ala Pro
                165                 170                 175

Thr Thr Val Ile Tyr Glu Asp Asn Gln Arg Pro Ser Gly Val Pro Asp
            180                 185                 190

Arg Phe Ser Gly Ser Ile Asp Ser Ser Ser Asn Ser Ala Ser Leu Thr
        195                 200                 205

Ile Ser Gly Leu Lys Thr Glu Asp Glu Ala Asp Tyr Tyr Cys Gln Thr
    210                 215                 220

Tyr Asp Asp Asn Asn His Val Ile Phe Gly Gly Gly Thr Gln Leu Thr
225                 230                 235                 240

Val Leu Gly


<210> SEQ ID NO 27
<211> LENGTH: 72
<212> TYPE: DNA
<213> ORGANISM: Artificial
<220> FEATURE:
<223> OTHER INFORMATION: CD8 transmembrane domain

<400> SEQUENCE: 27

atctacatct gggcgccctt ggccgggact tgtggggtcc ttctcctgtc actggttatc      60

accctttact gc                                                           72


<210> SEQ ID NO 28
<211> LENGTH: 22
<212> TYPE: PRT
<213> ORGANISM: Artificial
<220> FEATURE:
<223> OTHER INFORMATION: CD8 transmembrane domain

<400> SEQUENCE: 28

Ile Trp Ala Pro Leu Ala Gly Thr Cys Gly Val Leu Leu Leu Ser Leu
1               5                   10                  15

Val Ile Thr Leu Tyr Cys
            20


<210> SEQ ID NO 29
<211> LENGTH: 135
<212> TYPE: DNA
<213> ORGANISM: Artificial
<220> FEATURE:
<223> OTHER INFORMATION: CD8 hinge domain

<400> SEQUENCE: 29

accacgacgc cagcgccgcg accaccaaca ccggcgccca ccatcgcgtc gcagcccctg      60

tccctgcgcc cagaggcgtg ccggccagcg gcggggggcg cagtgcacac gagggggctg     120

gacttcgcct gtgat                                                       135


<210> SEQ ID NO 30
<211> LENGTH: 47
<212> TYPE: PRT
```

<213> ORGANISM: Artificial
<220> FEATURE:
<223> OTHER INFORMATION: CD8 hinge domain

<400> SEQUENCE: 30

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45
```

<210> SEQ ID NO 31
<211> LENGTH: 42
<212> TYPE: PRT
<213> ORGANISM: Homo sapiens

<400> SEQUENCE: 31

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 32
<211> LENGTH: 106
<212> TYPE: PRT
<213> ORGANISM: Homo sapiens

<400> SEQUENCE: 32

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 33
<211> LENGTH: 126
<212> TYPE: DNA
<213> ORGANISM: Artificial
<220> FEATURE:
<223> OTHER INFORMATION: signaling domain of 4-1BB

<400> SEQUENCE: 33

```
aaacggggca gaaagaaact cctgtatata ttcaaacaac catttatgag accagtacaa      60

actactcaag aggaagatgg ctgtagctgc cgatttccag aagaagaaga aggaggatgt     120

gaactg                                                                126
```

<210> SEQ ID NO 34

```
<211> LENGTH: 42
<212> TYPE: PRT
<213> ORGANISM: Artificial
<220> FEATURE:
<223> OTHER INFORMATION: signaling domain of 4-1BB

<400> SEQUENCE: 34

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 35
<211> LENGTH: 336
<212> TYPE: DNA
<213> ORGANISM: Artificial
<220> FEATURE:
<223> OTHER INFORMATION: signaling domain of CD3-zeta

<400> SEQUENCE: 35

agagtgaagt tcagcaggag cgcagacgcc cccgcgtaca agcagggcca gaaccagctc      60

tataacgagc tcaatctagg acgaagagag gagtacgatg ttttggacaa gagacgtggc     120

cgggaccctg agatgggggg aaagccgaga aggaagaacc ctcaggaagg cctgtacaat     180

gaactgcaga aagataagat ggcggaggcc tacagtgaga ttgggatgaa aggcgagcgc     240

cggaggggca aggggcacga tggcctttac cagggtctca gtacagccac caaggacacc     300

tacgacgccc ttcacatgca ggccctgccc cctcgc                               336


<210> SEQ ID NO 36
<211> LENGTH: 112
<212> TYPE: PRT
<213> ORGANISM: Artificial
<220> FEATURE:
<223> OTHER INFORMATION: CD3zeta

<400> SEQUENCE: 36

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 37
<211> LENGTH: 726
<212> TYPE: DNA
<213> ORGANISM: Artificial
<220> FEATURE:
<223> OTHER INFORMATION: ScFv CD 19

<400> SEQUENCE: 37
```

```
gacatccaga tgacacagac tacatcctcc ctgtctgcct ctctgggaga cagagtcacc     60

atcagttgca gggcaagtca ggacattagt aaatatttaa attggtatca gcagaaacca    120

gatggaactg ttaaactcct gatctaccat acatcaagat tacactcagg agtcccatca    180

aggttcagtg gcagtgggtc tggaacagat tattctctca ccattagcaa cctggagcaa    240

gaagatattg ccacttactt ttgccaacag ggtaatacgc ttccgtacac gttcggaggg    300

gggaccaagc tggagatcac aggtggcggt ggctcgggcg gtggtgggtc gggtggcggc    360

ggatctgagg tgaaactgca ggagtcagga cctggcctgg tggcgccctc acagagcctg    420

tccgtcacat gcactgtctc aggggtctca ttacccgact atggtgtaag ctggattcgc    480

cagcctccac gaaagggtct ggagtggctg ggagtaatat ggggtagtga aaccacatac    540

tataattcag ctctcaaatc cagactgacc atcatcaagg acaactccaa gagccaagtt    600

ttcttaaaaa tgaacagtct gcaaactgat gacacagcca tttactactg tgccaaacat    660

tattactacg gtggtagcta tgctatggac tactggggcc aaggaacctc agtcaccgtc    720

tcctca                                                                726
```

<210> SEQ ID NO 38
<211> LENGTH: 242
<212> TYPE: PRT
<213> ORGANISM: Artificial
<220> FEATURE:
<223> OTHER INFORMATION: ScFv CD 19

<400> SEQUENCE: 38

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220
```

-continued

Gly Ser Tyr Ala Met Asp Tyr Trp Gly Gln Gly Thr Ser Val Thr Val
225 230 235 240

Ser Ser

<210> SEQ ID NO 39
<211> LENGTH: 66
<212> TYPE: DNA
<213> ORGANISM: Artificial
<220> FEATURE:
<223> OTHER INFORMATION: GMCSF leader peptide

<400> SEQUENCE: 39
atgctgctgc tggtgaccag cctgctgctg tgcgaactgc cgcatccggc gtttctgctg 60
attccg 66

<210> SEQ ID NO 40
<211> LENGTH: 22
<212> TYPE: PRT
<213> ORGANISM: Artificial
<220> FEATURE:
<223> OTHER INFORMATION: GMCSF leader peptide

<400> SEQUENCE: 40

Met Leu Leu Leu Val Thr Ser Leu Leu Leu Cys Glu Leu Pro His Pro
1 5 10 15

Ala Phe Leu Leu Ile Pro
20

<210> SEQ ID NO 41
<211> LENGTH: 85
<212> TYPE: DNA
<213> ORGANISM: Artificial
<220> FEATURE:
<223> OTHER INFORMATION: TNFRSF19 leader peptide

<400> SEQUENCE: 41
ggctctgaaa gtgctgttgg aacaagaaaa gaccttcttc accttgctcg tgttgctggg 60
gtacctgtcc tgcaaagtca cctgt 85

<210> SEQ ID NO 42
<211> LENGTH: 29
<212> TYPE: PRT
<213> ORGANISM: Artificial
<220> FEATURE:
<223> OTHER INFORMATION: TNFRSF19 leader peptide

<400> SEQUENCE: 42

Met Ala Leu Lys Val Leu Leu Glu Gln Glu Lys Thr Phe Phe Thr Leu
1 5 10 15

Leu Val Leu Leu Gly Tyr Leu Ser Cys Lys Val Thr Cys
20 25

<210> SEQ ID NO 43
<211> LENGTH: 63
<212> TYPE: DNA
<213> ORGANISM: Artificial
<220> FEATURE:
<223> OTHER INFORMATION: CD8 alpha leader peptide

<400> SEQUENCE: 43
atggcgctgc cggtgaccgc gctgctgctg ccgctggcgc tgctgctgca tgcggcgcgc 60
ccg 63

<210> SEQ ID NO 44
<211> LENGTH: 21
<212> TYPE: PRT
<213> ORGANISM: Artificial
<220> FEATURE:
<223> OTHER INFORMATION: CD8 alpha leader peptide

<400> SEQUENCE: 44

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 45
<211> LENGTH: 123
<212> TYPE: DNA
<213> ORGANISM: Artificial
<220> FEATURE:
<223> OTHER INFORMATION: CD28 co-stimulatory domain

<400> SEQUENCE: 45

```
cggtcgaaga ggtccagact cttgcactcc gactacatga acatgactcc tagaaggccc     60

ggacccacta gaaagcacta ccagccgtac gcccctcctc gggatttcgc cgcataccgg    120

tcc                                                                  123
```

<210> SEQ ID NO 46
<211> LENGTH: 41
<212> TYPE: PRT
<213> ORGANISM: Artificial
<220> FEATURE:
<223> OTHER INFORMATION: CD28 co-stimulatory domain

<400> SEQUENCE: 46

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 47
<211> LENGTH: 336
<212> TYPE: DNA
<213> ORGANISM: Artificial
<220> FEATURE:
<223> OTHER INFORMATION: CD3 zeta activation domain

<400> SEQUENCE: 47

```
agagtgaagt tcagccgctc agccgatgca ccggcctacc agcagggaca gaaccagctc     60

tacaacgagc tcaacctggg tcggcgggaa gaatatgacg tgctggacaa acggcgcggc    120

agagatccgg agatgggggg aaagccgagg aggaagaacc ctcaagaggg cctgtacaac    180

gaactgcaga aggacaagat ggcggaagcc tactccgaga tcggcatgaa gggagaacgc    240

cggagaggga agggtcatga cggactgtac cagggcctgt caactgccac taaggacact    300

tacgatgcgc tccatatgca agctttgccc ccgcgg                              336
```

<210> SEQ ID NO 48
<211> LENGTH: 112
<212> TYPE: PRT
<213> ORGANISM: Artificial
<220> FEATURE:

<223> OTHER INFORMATION: CD3 zeta activation domain

<400> SEQUENCE: 48

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 49
<211> LENGTH: 201
<212> TYPE: DNA
<213> ORGANISM: Artificial
<220> FEATURE:
<223> OTHER INFORMATION: TNFRSF19 hinge and transmembrane domain

<400> SEQUENCE: 49
gcggccgcgg tcggattcca agacatggaa tgcgtgccct gcggcgaccc gccacctcct 60
tacgagccgc actgcgcatc gaaggtcaac ctcgtgaaga tcgcgagcac cgcgtcctca 120
ccccgggata ctgctctggc cgccgtgatt tgttccgcct tggccaccgt gcttctggcc 180
ctgctgatcc tctgtgtgat c 201

<210> SEQ ID NO 50
<211> LENGTH: 67
<212> TYPE: PRT
<213> ORGANISM: Artificial
<220> FEATURE:
<223> OTHER INFORMATION: TNFRSF19 hinge and transmembrane domain

<400> SEQUENCE: 50

Ala Ala Ala Val Gly Phe Gln Asp Met Glu Cys Val Pro Cys Gly Asp
1 5 10 15

Pro Pro Pro Pro Tyr Glu Pro His Cys Ala Ser Lys Val Asn Leu Val
20 25 30

Lys Ile Ala Ser Thr Ala Ser Ser Pro Arg Asp Thr Ala Leu Ala Ala
35 40 45

Val Ile Cys Ser Ala Leu Ala Thr Val Leu Leu Ala Leu Leu Ile Leu
50 55 60

Cys Val Ile
65

<210> SEQ ID NO 51
<211> LENGTH: 63
<212> TYPE: DNA
<213> ORGANISM: Artificial
<220> FEATURE:
<223> OTHER INFORMATION: TNFRSF19 transmembrane domain

<400> SEQUENCE: 51
gccgccgtga tttgttccgc cttggccacc gtgcttctgg ccctgctgat cctctgtgtg 60
atc 63

<210> SEQ ID NO 52
<211> LENGTH: 21
<212> TYPE: PRT
<213> ORGANISM: Artificial
<220> FEATURE:
<223> OTHER INFORMATION: TNFRSF19 transmembrane domain

<400> SEQUENCE: 52

Ala Ala Val Ile Cys Ser Ala Leu Ala Thr Val Leu Leu Ala Leu Leu
1 5 10 15

Ile Leu Cys Val Ile
20

<210> SEQ ID NO 53
<211> LENGTH: 138
<212> TYPE: DNA
<213> ORGANISM: Artificial
<220> FEATURE:
<223> OTHER INFORMATION: TNFRSF19 hinge domain

<400> SEQUENCE: 53
gcggccgcgg tcggattcca agacatggaa tgcgtgccct gcggcgaccc gccacctcct 60
tacgagccgc actgcgcatc gaaggtcaac ctcgtgaaga tcgcgagcac cgcgtcctca 120
ccccgggata ctgctctg 138

<210> SEQ ID NO 54
<211> LENGTH: 46
<212> TYPE: PRT
<213> ORGANISM: Artificial
<220> FEATURE:
<223> OTHER INFORMATION: TNFRSF19 hinge domain

<400> SEQUENCE: 54

Ala Ala Ala Val Gly Phe Gln Asp Met Glu Cys Val Pro Cys Gly Asp
1 5 10 15

Pro Pro Pro Pro Tyr Glu Pro His Cys Ala Ser Lys Val Asn Leu Val
20 25 30

Lys Ile Ala Ser Thr Ala Ser Ser Pro Arg Asp Thr Ala Leu
35 40 45

<210> SEQ ID NO 55
<211> LENGTH: 80
<212> TYPE: DNA
<213> ORGANISM: Artificial
<220> FEATURE:
<223> OTHER INFORMATION: truncated TNFRSF19 hinge domain

<400> SEQUENCE: 55
tacgagcctc actgcgccag caaagtcaac ttggtgaaga tcgcgagcac tgcctcgtcc 60
cctcgggaca ctgctctggc 80

<210> SEQ ID NO 56
<211> LENGTH: 26
<212> TYPE: PRT
<213> ORGANISM: Artificial
<220> FEATURE:
<223> OTHER INFORMATION: TNFRSF19 hinge domain

<400> SEQUENCE: 56

Tyr Glu Pro His Cys Ala Ser Lys Val Asn Leu Val Lys Ile Ala Ser

```
1               5                   10                  15

Thr Ala Ser Ser Pro Arg Asp Thr Ala Leu
            20                  25


<210> SEQ ID NO 57
<211> LENGTH: 222
<212> TYPE: DNA
<213> ORGANISM: Artificial
<220> FEATURE:
<223> OTHER INFORMATION: CD8a hinge domain fused to TNFRSF19
      transmembrane

<400> SEQUENCE: 57

gcggccgcgc ccgcccctcg gcccccgact cctgccccga cgatcgcttc ccaacctctc      60

tcgctgcgcc cggaagcatg ccggcccgcc gccggtggcg ctgtccacac tcgcggactg     120

gactttgata ccgcactggc ggccgtgatc tgtagcgccc tggccaccgt gctgctggcg     180

ctgctcatcc tttgcgtgat ctactgcaag cggcagccta gg                        222


<210> SEQ ID NO 58
<211> LENGTH: 74
<212> TYPE: PRT
<213> ORGANISM: Artificial
<220> FEATURE:
<223> OTHER INFORMATION: CD8a hinge domain fused to TNFRSF19
      transmembrane

<400> SEQUENCE: 58

Ala Ala Ala Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Asp Thr Ala Leu Ala Ala
        35                  40                  45

Val Ile Cys Ser Ala Leu Ala Thr Val Leu Leu Ala Leu Leu Ile Leu
    50                  55                  60

Cys Val Ile Tyr Cys Lys Arg Gln Pro Arg
65                  70


<210> SEQ ID NO 59
<211> LENGTH: 123
<212> TYPE: DNA
<213> ORGANISM: Artificial
<220> FEATURE:
<223> OTHER INFORMATION: CD28 co-stimulatory domain

<400> SEQUENCE: 59

cggtcgaaga ggtccagact cttgcactcc gactacatga acatgactcc tagaaggccc      60

ggacccacta gaaagcacta ccagccgtac gcccctcctc gggatttcgc cgcataccgg     120

tcc                                                                   123


<210> SEQ ID NO 60
<211> LENGTH: 41
<212> TYPE: PRT
<213> ORGANISM: Artificial
<220> FEATURE:
<223> OTHER INFORMATION: CD28 co-stimulatory domain

<400> SEQUENCE: 60

Arg Ser Lys Arg Ser Arg Leu Leu His Ser Asp Tyr Met Asn Met Thr
1               5                   10                  15
```

```
Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 61
<211> LENGTH: 336
<212> TYPE: DNA
<213> ORGANISM: Artificial
<220> FEATURE:
<223> OTHER INFORMATION: CD3 zeta version 2

<400> SEQUENCE: 61

cgcgtgaaat ttagccgcag cgcggatgcg ccggcgtatc agcagggcca gaaccagctg      60

tataacgaac tgaacctggg ccgccgcgaa gaatatgatg tgctggataa acgccgcggc     120

cgcgatccgg aaatgggcgg caaaccgcgc cgcaaaaacc cgcaggaagg cctgtataac     180

gaactgcaga aagataaaat ggcggaagcg tatagcgaaa ttggcatgaa aggcgaacgc     240

cgccgcggca aaggccatga tggcctgtat cagggcctga gcaccgcgac caaagatacc     300

tatgatgcgc tgcatatgca ggcgctgccg ccgcgc                               336


<210> SEQ ID NO 62
<211> LENGTH: 112
<212> TYPE: PRT
<213> ORGANISM: Artificial
<220> FEATURE:
<223> OTHER INFORMATION: CD3 zeta version 2

<400> SEQUENCE: 62

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 63
<211> LENGTH: 93
<212> TYPE: DNA
<213> ORGANISM: Artificial
<220> FEATURE:
<223> OTHER INFORMATION: Furin P2A Furin

<400> SEQUENCE: 63

cgcgcgaaac gcagcggcag cggcgcgacc aactttagcc tgctgaaaca ggcgggcgat      60

gtggaagaaa acccgggccc gcgagcaaag agg                                   93


<210> SEQ ID NO 64
<211> LENGTH: 31
<212> TYPE: PRT
<213> ORGANISM: Artificial
<220> FEATURE:
```

<223> OTHER INFORMATION: Furin P2A Furin

<400> SEQUENCE: 64

Arg Ala Lys Arg Ser Gly Ser Gly Ala Thr Asn Phe Ser Leu Leu Lys
1 5 10 15

Gln Ala Gly Asp Val Glu Glu Asn Pro Gly Pro Arg Ala Lys Arg
20 25 30

<210> SEQ ID NO 65
<211> LENGTH: 78
<212> TYPE: DNA
<213> ORGANISM: Artificial
<220> FEATURE:
<223> OTHER INFORMATION: Furin T2A

<400> SEQUENCE: 65
agagctaaac gctctgggtc tggtgaagga cgaggtagcc ttcttacgtg cggagacgtg 60
gaggaaaacc caggaccc 78

<210> SEQ ID NO 66
<211> LENGTH: 26
<212> TYPE: PRT
<213> ORGANISM: Artificial
<220> FEATURE:
<223> OTHER INFORMATION: Furin T2A

<400> SEQUENCE: 66

Arg Ala Lys Arg Ser Gly Ser Gly Glu Gly Arg Gly Ser Leu Leu Thr
1 5 10 15

Cys Gly Asp Val Glu Glu Asn Pro Gly Pro
20 25

<210> SEQ ID NO 67
<211> LENGTH: 1005
<212> TYPE: DNA
<213> ORGANISM: Artificial
<220> FEATURE:
<223> OTHER INFORMATION: truncated EGFR (tEGFR) tag

<400> SEQUENCE: 67
aggaaggttt gcaatggaat cggtataggg gagtttaagg attcacttag cataaacgct 60
actaatatta aacacttcaa aaactgtacg agtataagtg gagatcttca cattttgccg 120
gttgcattcc gaggcgattc attcacccac acgccaccgc ttgacccaca agaattggat 180
attcttaaaa ccgttaaaga aataacgggg tttttgctca ttcaagcgtg gccagaaaat 240
cgcactgacc tccatgcttt cgagaacctg gagattataa gaggacgaac taagcagcat 300
ggtcaattct cccttgctgt ggtcagcctg aacatcacca gtcttggttt gcggtccctc 360
aaggaaattt cagatggaga tgtcatcata agcggcaaca agaatttgtg ctatgcaaat 420
accataaact ggaaaaaact gtttggcact tccggccaga aaaccaagat tatttcaaat 480
cggggtgaga acagctgcaa agccaccggc caggtttgtc atgccttgtg ctctccggaa 540
ggctgttggg ggccagaacc cagggactgc gtcagttgca gaaacgtctc aagaggccgc 600
gaatgcgttg acaagtgtaa cctccttgag ggtgagccac gagagtttgt tgagaacagc 660
gagtgtatac aatgtcaccc tgaatgtttg ccccaggcta tgaatataac ctgcacaggc 720
cgcgggcctg ataactgcat ccagtgtgct cattacatag atggacctca ctgtgtgaaa 780
acctgcccgg ccggagttat gggagaaaac aacactctgg tgtggaaata cgctgatgca 840
ggccacgtgt gccacctttg tcacccgaat tgtacatatg ggtgtaccgg tcctggactt 900
gaaggttgcc ctaccaatgg ccctaaaata cccagtatcg caactggcat ggtaggcgct 960
cttctcttgc tcttggtagt tgctctcggc ataggtcttt ttatg 1005

<210> SEQ ID NO 68
<211> LENGTH: 335
<212> TYPE: PRT
<213> ORGANISM: Artificial
<220> FEATURE:
<223> OTHER INFORMATION: truncated EGFR (tEGFR) tag

<400> SEQUENCE: 68

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn
65 70 75 80

Arg Thr Asp Leu His Ala Phe Glu Asn Leu Glu Ile Ile Arg Gly Arg
85 90 95

Thr Lys Gln His Gly Gln Phe Ser Leu Ala Val Val Ser Leu Asn Ile
100 105 110

Thr Ser Leu Gly Leu Arg Ser Leu Lys Glu Ile Ser Asp Gly Asp Val
115 120 125

Ile Ile Ser Gly Asn Lys Asn Leu Cys Tyr Ala Asn Thr Ile Asn Trp
130 135 140

Lys Lys Leu Phe Gly Thr Ser Gly Gln Lys Thr Lys Ile Ile Ser Asn
145 150 155 160

Arg Gly Glu Asn Ser Cys Lys Ala Thr Gly Gln Val Cys His Ala Leu
165 170 175

Cys Ser Pro Glu Gly Cys Trp Gly Pro Glu Pro Arg Asp Cys Val Ser
180 185 190

Cys Arg Asn Val Ser Arg Gly Arg Glu Cys Val Asp Lys Cys Asn Leu
195 200 205

Leu Glu Gly Glu Pro Arg Glu Phe Val Glu Asn Ser Glu Cys Ile Gln
210 215 220

Cys His Pro Glu Cys Leu Pro Gln Ala Met Asn Ile Thr Cys Thr Gly
225 230 235 240

Arg Gly Pro Asp Asn Cys Ile Gln Cys Ala His Tyr Ile Asp Gly Pro
245 250 255

His Cys Val Lys Thr Cys Pro Ala Gly Val Met Gly Glu Asn Asn Thr
260 265 270

Leu Val Trp Lys Tyr Ala Asp Ala Gly His Val Cys His Leu Cys His
275 280 285

Pro Asn Cys Thr Tyr Gly Cys Thr Gly Pro Gly Leu Glu Gly Cys Pro
290 295 300

Thr Asn Gly Pro Lys Ile Pro Ser Ile Ala Thr Gly Met Val Gly Ala
305 310 315 320

Leu Leu Leu Leu Leu Val Val Ala Leu Gly Ile Gly Leu Phe Met
325 330 335

<210> SEQ ID NO 69
<211> LENGTH: 744
<212> TYPE: DNA
<213> ORGANISM: Artificial
<220> FEATURE:
<223> OTHER INFORMATION: BCMA ScFv binder MTB-40

<400> SEQUENCE: 69
caggcggccg aggtgcagct ggtgcagtct gggggaggcg tggtccagcc tgggggggtcc 60 ctgagactct cctgtgcagc gtctggattc accttcagta gctatggcat gcactgggtc 120
cgccaggctc caggcaaggg gctggagtgg gtggcattta tacggtatga tggaagtaat 180
aaatactacg cagactccgt gaagggccga ttcaccatct ccagagacaa ttccaagaac 240
acgctgtatc tgcaaatgaa cagcctgaga gctgaggaca cggctgtgta ttactgtgcg 300
aaagaacccc ccgagtatta ctatgatagt agtggttatt cgtggggcca gggaaccctg 360
gtcaccgtct cctcaggagg tggcggatct ggtggaggcg gtagcggtgg tggcggatcc 420
gacatccagt tgacccagtc tccatcctcc ctgtctgcat ctgtaggaga cagagtcacc 480
atcacttgcc aggcgagtca ggacattgac acctatttaa actggtatca gcagaaacca 540
gggaaagccc ctaagctcct gatctatgct gcatccagtt tgcaaagtgg ggtctcatca 600
aggttcagtg gcagtggatc tgggacagag ttcactctca ccatcagcag tctgcagcct 660
gaagattttg caacttattt ctgtcaacag acttacagtc cccgatcac cttcggccaa 720 gggacacgac tggagattaa acga 744

<210> SEQ ID NO 70
<211> LENGTH: 248
<212> TYPE: PRT
<213> ORGANISM: Artificial
<220> FEATURE:
<223> OTHER INFORMATION: BCMA ScFv binder MTB-40

<400> SEQUENCE: 70

Gln Ala Ala Glu Val Gln Leu Val Gln Ser Gly Gly Gly Val Val Gln
1 5 10 15

Pro Gly Gly Ser Leu Arg Leu Ser Cys Ala Ala Ser Gly Phe Thr Phe
20 25 30

Ser Ser Tyr Gly Met His Trp Val Arg Gln Ala Pro Gly Lys Gly Leu
35 40 45

Glu Trp Val Ala Phe Ile Arg Tyr Asp Gly Ser Asn Lys Tyr Tyr Ala
50 55 60

Asp Ser Val Lys Gly Arg Phe Thr Ile Ser Arg Asp Asn Ser Lys Asn
65 70 75 80

Thr Leu Tyr Leu Gln Met Asn Ser Leu Arg Ala Glu Asp Thr Ala Val
85 90 95

Tyr Tyr Cys Ala Lys Glu Pro Pro Glu Tyr Tyr Tyr Asp Ser Ser Gly
100 105 110

Tyr Ser Trp Gly Gln Gly Thr Leu Val Thr Val Ser Ser Gly Gly Gly
115 120 125

Gly Ser Gly Gly Gly Gly Ser Gly Gly Gly Gly Ser Asp Ile Gln Leu
130 135 140

Thr Gln Ser Pro Ser Ser Leu Ser Ala Ser Val Gly Asp Arg Val Thr
145 150 155 160

Ile Thr Cys Gln Ala Ser Gln Asp Ile Asp Thr Tyr Leu Asn Trp Tyr
165 170 175

Gln Gln Lys Pro Gly Lys Ala Pro Lys Leu Leu Ile Tyr Ala Ala Ser

-continued

```
        180                 185                 190

Ser Leu Gln Ser Gly Val Ser Ser Arg Phe Ser Gly Ser Gly Ser Gly
        195                 200                 205

Thr Glu Phe Thr Leu Thr Ile Ser Ser Leu Gln Pro Glu Asp Phe Ala
    210                 215                 220

Thr Tyr Phe Cys Gln Gln Thr Tyr Ser Pro Pro Ile Thr Phe Gly Gln
225                 230                 235                 240

Gly Thr Arg Leu Glu Ile Lys Arg
                245


<210> SEQ ID NO 71
<211> LENGTH: 729
<212> TYPE: DNA
<213> ORGANISM: Artificial
<220> FEATURE:
<223> OTHER INFORMATION: BCMA ScFv binder MTB-49

<400> SEQUENCE: 71

gaggtgcagc tggtggagtc tgggggaggc gtggtccagc ctgggaggtc cctgagactc      60

tcctgtgcag cgtctggatt caccttcagt agctatggca tgcactgggt ccgccaggct     120

ccaggcaagg ggctggagtg ggtggcattt atacggtatg atggaagtaa taaatactat     180

gcagactccg tgaagggccg attcaccatc tccagagaca attccaagaa cacgctgtat     240

ctgcaaatga acagcctgag agctgaggac acggctgtgt attactgtgt gagcgatgac     300

tacggtggta actccgggac tagctactgg ggccagggaa ccctggtcac cgtctcctca     360

ggaggtggcg gatctggtgg aggcggtagc ggtggtggcg gatccgacat ccagatgacc     420

cagtctccat cctccctgtc tgcatctgta ggagacagag tcaccatcac ttgccaggcg     480

agtcaggaca ttagcaacta tttaaattgg tatcagcaga agccagggaa agcccctaag     540

ctcctgatct acgatgcatc caatttggaa acaggggtcc catcaaggtt cagtggcagt     600

ggatctggga cagatttcac tctcaccatc agcagtctgc aacctgaaga ttttgcaact     660

tactactgtc aacagagtta cagtaccccc gtgacgttcg gcggagggac caagctgacc     720

gtcctaggt                                                             729


<210> SEQ ID NO 72
<211> LENGTH: 243
<212> TYPE: PRT
<213> ORGANISM: Artificial
<220> FEATURE:
<223> OTHER INFORMATION: BCMA ScFv binder MTB-49

<400> SEQUENCE: 72

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Ser Asp Asp Tyr Gly Gly Asn Ser Gly Thr Ser Tyr Trp Gly Gln
```

```
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Gln Ala
145                 150                 155                 160

Ser Gln Asp Ile Ser Asn Tyr Leu Asn Trp Tyr Gln Gln Lys Pro Gly
                165                 170                 175

Lys Ala Pro Lys Leu Leu Ile Tyr Asp Ala Ser Asn Leu Glu Thr Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Ser Tyr Ser Thr Pro Val Thr Phe Gly Gly Gly Thr Lys Leu Thr
225                 230                 235                 240

Val Leu Gly


<210> SEQ ID NO 73
<211> LENGTH: 711
<212> TYPE: DNA
<213> ORGANISM: Artificial
<220> FEATURE:
<223> OTHER INFORMATION: BCMA ScFv binder MTB-50

<400> SEQUENCE: 73

gaggtgcagc tggtgcagtc tggggggaggt gtggtacggc ctggggggtc cctgagactc      60

tcctgtgcag cctctggatt caccttcagt acttatgaaa tgaactgggt ccgccaggct     120

ccagggaagg ggctggagtg gcttgcatac attggaggta gtggtagtcc catatactac     180

gcagactctg tgaggggccg attcaccatc tccagagaca acaccaagaa ttcactattt     240

ctccaaatga gcagcctgag agccgaggac accgctgttt actattgtgt ggaagggtgg     300

tttgacaagt ggggcctggg aaccctggtc accgtctcct caggaggtgg cggatctggt     360

ggaggcggta gcggtggtgg cggatccgac atccagttga cccagtctcc atccaccctg     420

tctgcatctg taggagacag agtcaccatc acttgccggg caagtcagag cattagcagc     480

tatttaaatt ggtatcagca gaaaccaggg aaagccccta agctcctgat ctacgatgca     540

tccaatttgg agacaggggt cccatcaagg ttcagtggaa gtggatctgg gacagatttc     600

actctcacca tcagcagtct gcaacctgaa gattttgcaa cttactactg tcaacagagt     660

tacagtaccc cgtacacttt tggccagggg accaagctgg aaatcaaacg t              711


<210> SEQ ID NO 74
<211> LENGTH: 237
<212> TYPE: PRT
<213> ORGANISM: Artificial
<220> FEATURE:
<223> OTHER INFORMATION: BCMA ScFv binder MTB-50

<400> SEQUENCE: 74

Glu Val Gln Leu Val Gln Ser Gly Gly Gly Val Val Arg Pro Gly Gly
1               5                   10                  15

Ser Leu Arg Leu Ser Cys Ala Ala Ser Gly Phe Thr Phe Ser Thr Tyr
            20                  25                  30

Glu Met Asn Trp Val Arg Gln Ala Pro Gly Lys Gly Leu Glu Trp Leu
```

-continued

```
        35                  40                  45

Ala Tyr Ile Gly Gly Ser Gly Ser Pro Ile Tyr Tyr Ala Asp Ser Val
    50                  55                  60

Arg Gly Arg Phe Thr Ile Ser Arg Asp Asn Thr Lys Asn Ser Leu Phe
65                  70                  75                  80

Leu Gln Met Ser Ser Leu Arg Ala Glu Asp Thr Ala Val Tyr Tyr Cys
                85                  90                  95

Val Glu Gly Trp Phe Asp Lys Trp Gly Leu Gly Thr Leu Val Thr Val
            100                 105                 110

Ser Ser Gly Gly Gly Gly Ser Gly Gly Gly Gly Ser Gly Gly Gly Gly
        115                 120                 125

Ser Asp Ile Gln Leu Thr Gln Ser Pro Ser Thr Leu Ser Ala Ser Val
    130                 135                 140

Gly Asp Arg Val Thr Ile Thr Cys Arg Ala Ser Gln Ser Ile Ser Ser
145                 150                 155                 160

Tyr Leu Asn Trp Tyr Gln Gln Lys Pro Gly Lys Ala Pro Lys Leu Leu
                165                 170                 175

Ile Tyr Asp Ala Ser Asn Leu Glu Thr Gly Val Pro Ser Arg Phe Ser
            180                 185                 190

Gly Ser Gly Ser Gly Thr Asp Phe Thr Leu Thr Ile Ser Ser Leu Gln
        195                 200                 205

Pro Glu Asp Phe Ala Thr Tyr Tyr Cys Gln Gln Ser Tyr Ser Thr Pro
    210                 215                 220

Tyr Thr Phe Gly Gln Gly Thr Lys Leu Glu Ile Lys Arg
225                 230                 235
```

<210> SEQ ID NO 75
<211> LENGTH: 732
<212> TYPE: DNA
<213> ORGANISM: Artificial
<220> FEATURE:
<223> OTHER INFORMATION: BCMA ScFv binder MTB-4-12

<400> SEQUENCE: 75

```
caggtgcagc tggtgcagtc tgggggaggc gtggtccagc ctgggggtc cctgagactc      60

tcctgtgcag cctctggatt caccttcagt agttacgtta tacattgggt ccgccaggct     120

ccaggcaagg ggctggagtg ggtggcagct atatcgcatg atggaagcaa taaatactac     180

gcagactccg tgaagggccg attcaccatc tccagagaca attccaagaa cacgctgtat     240

cttcaaatga gcagtctgag cgctgaggac acggctatgt attactgtgt gaaaactagt     300

agtgattatt actacgccta ctggggccag ggaaccctgg tcaccgtctc ctcaggaggt     360

ggcgggtctg gtggaggcgg tagcggtggt ggcggatccc agactgtggt gactcaggag     420

ccatcgttct cagtgtcccc tggagggaca gtcacactca cttgtggctt gagctctggc     480

tcagtctcta ctggcaactc cccacctgg taccagcaga ccccaggcca ggctccacgc      540

acgctcatct acagcacaaa cactcgctct tctggggtcc ctgatcgctt ctctggctcc     600

atccttggga acaaagctgc cctcaccatc acgggggccc aggcagatga tgaatctgat     660

tattactgtg tgctgtatat gggtagtggc tattgggtgt tcggcggagg gaccaaggtc     720

accgtcctag gt                                                        732
```

<210> SEQ ID NO 76
<211> LENGTH: 244
<212> TYPE: PRT
<213> ORGANISM: Artificial

<220> FEATURE:
<223> OTHER INFORMATION: BCMA ScFv binder MTB-4-12

<400> SEQUENCE: 76

Gln Val Gln Leu Val Gln Ser Gly Gly Gly Val Val Gln Pro Gly Gly
1 5 10 15

Ser Leu Arg Leu Ser Cys Ala Ala Ser Gly Phe Thr Phe Ser Ser Tyr
20 25 30

Val Ile His Trp Val Arg Gln Ala Pro Gly Lys Gly Leu Glu Trp Val
35 40 45

Ala Ala Ile Ser His Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Ser Ser Leu Ser Ala Glu Asp Thr Ala Met Tyr Tyr Cys
85 90 95

Val Lys Thr Ser Ser Asp Tyr Tyr Tyr Ala Tyr Trp Gly Gln Gly Thr
100 105 110

Leu Val Thr Val Ser Ser Gly Gly Gly Gly Ser Gly Gly Gly Gly Ser
115 120 125

Gly Gly Gly Gly Ser Gln Thr Val Val Thr Gln Glu Pro Ser Phe Ser
130 135 140

Val Ser Pro Gly Gly Thr Val Thr Leu Thr Cys Gly Leu Ser Ser Gly
145 150 155 160

Ser Val Ser Thr Gly Asn Ser Pro Thr Trp Tyr Gln Gln Thr Pro Gly
165 170 175

Gln Ala Pro Arg Thr Leu Ile Tyr Ser Thr Asn Thr Arg Ser Ser Gly
180 185 190

Val Pro Asp Arg Phe Ser Gly Ser Ile Leu Gly Asn Lys Ala Ala Leu
195 200 205

Thr Ile Thr Gly Ala Gln Ala Asp Asp Glu Ser Asp Tyr Tyr Cys Val
210 215 220

Leu Tyr Met Gly Ser Gly Tyr Trp Val Phe Gly Gly Gly Thr Lys Val
225 230 235 240

Thr Val Leu Gly

<210> SEQ ID NO 77
<211> LENGTH: 723
<212> TYPE: DNA
<213> ORGANISM: Artificial
<220> FEATURE:
<223> OTHER INFORMATION: BCMA ScFv binder MTB-4-45

<400> SEQUENCE: 77
gaggtgcagc tggtgcagtc tggggctgag gtgaagaagc ctggggcctc agtgaaggtt 60
tcctgcaagg catctggata cacctccacc agctactata tgcactgggt gcgacaggcc 120
cctggacaag ggcttgagtg gatgggaata atcaacccta gtggtggtag cacaagctac 180
gcacagaagt tccagggcag agtcaccatg accagggaca cgtccacgag cacagtctac 240
atggagctga gcagcttgag atctgaggac acggccgtgt attactgtgc gagagatttg 300
ggtgatggcg cttttgatat ctggggccaa gggacaatgg tcaccgtctc ttcaggaggt 360
ggcgggtctg gtggaggcgg tagcggtggt ggcggatccg acatccagat gacccagtct 420
ctatcctccc tgtctgcatc tgtaggagac agagtcacca tcgcttgccg ggcaagtcag 480
accattagta ggtatttaaa ttggtatcag cagaaaccag ggaaagcccc taagctcctg 540

```
atctatgctg catccagttt gcaaagtggg gtctcatcaa ggttcagtgg cagtggatct    600

gggacagagt tcactctcac catcagcagt ctgcagcctg aagattttgc aacttatttc    660

tgtcaacaga cttacagtcc cccgatcacc ttcggccaag ggacacgact ggagattaaa    720

cga                                                                  723


<210> SEQ ID NO 78
<211> LENGTH: 241
<212> TYPE: PRT
<213> ORGANISM: Artificial
<220> FEATURE:
<223> OTHER INFORMATION: BCMA ScFv binder  MTB-4-45

<400> SEQUENCE: 78

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Ser Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Leu Gly Asp Gly Ala Phe Asp Ile Trp Gly Gln Gly Thr
            100                 105                 110

Met Val Thr Val Ser Ser Gly Gly Gly Gly Ser Gly Gly Gly Gly Ser
        115                 120                 125

Gly Gly Gly Gly Ser Asp Ile Gln Met Thr Gln Ser Leu Ser Ser Leu
    130                 135                 140

Ser Ala Ser Val Gly Asp Arg Val Thr Ile Ala Cys Arg Ala Ser Gln
145                 150                 155                 160

Thr Ile Ser Arg Tyr Leu Asn Trp Tyr Gln Gln Lys Pro Gly Lys Ala
                165                 170                 175

Pro Lys Leu Leu Ile Tyr Ala Ala Ser Ser Leu Gln Ser Gly Val Ser
            180                 185                 190

Ser Arg Phe Ser Gly Ser Gly Ser Gly Thr Glu Phe Thr Leu Thr Ile
        195                 200                 205

Ser Ser Leu Gln Pro Glu Asp Phe Ala Thr Tyr Phe Cys Gln Gln Thr
    210                 215                 220

Tyr Ser Pro Pro Ile Thr Phe Gly Gln Gly Thr Arg Leu Glu Ile Lys
225                 230                 235                 240

Arg


<210> SEQ ID NO 79
<211> LENGTH: 36
<212> TYPE: DNA
<213> ORGANISM: Homo sapiens

<400> SEQUENCE: 79

gagagcaaat acgggccgcc atgtcccccg tgtccg                               36


<210> SEQ ID NO 80
<211> LENGTH: 12
```

<212> TYPE: PRT
<213> ORGANISM: Homo sapiens

<400> SEQUENCE: 80

Glu Ser Lys Tyr Gly Pro Pro Cys Pro Pro Cys Pro
1               5                   10

<210> SEQ ID NO 81
<211> LENGTH: 327
<212> TYPE: DNA
<213> ORGANISM: Homo sapiens

<400> SEQUENCE: 81
gcaccaccag ttgctggccc tagtgtcttc ttgttccctc ccaagcccaa agacaccttg     60
atgatttcca gaactcctga ggttacctgc gttgtcgtag atgtttctca ggaggaccca    120
gaggtccaat ttaactggta cgttgatggg gtggaagttc acaatgcgaa gacaaagccg    180
cgggaagaac aatttcagtc cacttaccgg gttgtcagcg ttctgacggt attgcatcaa    240
gactggctta atggaaagga atataagtgt aaggtgtcca acaaaggttt gccgagcagt    300
attgagaaga ccatatcaaa ggcgaag                                        327

<210> SEQ ID NO 82
<211> LENGTH: 109
<212> TYPE: PRT
<213> ORGANISM: Homo sapiens

<400> SEQUENCE: 82

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser Gln Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Gln Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Gly
                85                  90                  95

Leu Pro Ser Ser Ile Glu Lys Thr Ile Ser Lys Ala Lys
            100                 105

<210> SEQ ID NO 83
<211> LENGTH: 321
<212> TYPE: DNA
<213> ORGANISM: Homo sapiens

<400> SEQUENCE: 83
gggcagccgc gcgagccaca agtttacact ttgccgccat ctcaagagga aatgactaaa     60
aaccaggtat ccttgacatg cctcgtaaaa ggattttatc catctgatat tgctgtggaa    120
tgggagtcta acgggcagcc ggaaaataat tacaaaacta caccacctgt gctcgattca    180
gatggaagtt tcttccttta cagtagactt acggtggaca aatctaggtg gcaggaaggg    240
aatgtgttta gttgtagtgt aatgcacgag gcacttcata accactatac acagaagtca    300
ctgagtttga gtcttggcaa a                                              321

<210> SEQ ID NO 84

<211> LENGTH: 107
<212> TYPE: PRT
<213> ORGANISM: Homo sapiens

<400> SEQUENCE: 84

```
Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105
```

<210> SEQ ID NO 85
<211> LENGTH: 684
<212> TYPE: DNA
<213> ORGANISM: Homo sapiens

<400> SEQUENCE: 85

```
gagagcaaat acgggccgcc atgtcccccg tgtccggcac caccagttgc tggccctagt      60

gtcttcttgt tccctcccaa gcccaaagac accttgatga tttccagaac tcctgaggtt     120

acctgcgttg tcgtagatgt ttctcaggag gacccagagg tccaatttaa ctggtacgtt     180

gatggggtgg aagttcacaa tgcgaagaca aagccgcggg aagaacaatt tcagtccact     240

taccgggttg tcagcgttct gacggtattg catcaagact ggcttaatgg aaaggaatat     300

aagtgtaagg tgtccaacaa aggtttgccg agcagtattg agaagaccat atcaaaggcg     360

aaggggcagc cgcgcgagcc acaagtttac actttgccgc catctcaaga ggaaatgact     420

aaaaaccagg tatccttgac atgcctcgta aaaggatttt atccatctga tattgctgtg     480

gaatgggagt ctaacgggca gccggaaaat aattacaaaa ctacaccacc tgtgctcgat     540

tcagatggaa gtttcttcct ttacagtaga cttacggtgg acaaatctag gtggcaggaa     600

gggaatgtgt ttagttgtag tgtaatgcac gaggcacttc ataaccacta tacacagaag     660

tcactgagtt tgagtcttgg caaa                                            684
```

<210> SEQ ID NO 86
<211> LENGTH: 228
<212> TYPE: PRT
<213> ORGANISM: Homo sapiens

<400> SEQUENCE: 86

```
Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60
```

-continued

```
Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys
225
```

<210> SEQ ID NO 87
<211> LENGTH: 1497
<212> TYPE: DNA
<213> ORGANISM: Artificial
<220> FEATURE:
<223> OTHER INFORMATION: D0084 (Ef1a-BCMA sequence 5 CD8 BBz)

<400> SEQUENCE: 87

```
atgctgctgc tggtgaccag cctgcttctg tgtgaactgc cgcatccggc gtttctgctg      60

attccggagg tccagctggt gcagtctgga ggaggcgtgg tccagcctgg tgggtccctg     120

agactctcct gtgcagcgtc tggattcacc ttcagtagct atggcatgca ctgggtccgc     180

caggctccag gcaaggggct ggagtgggtg gcatttatac ggtatgatgg aagtaataaa     240

tactatgcag actccgtgaa gggccgattc accatctcca gagacaattc caagaacacg     300

ctgtatctgc aaatgaacag cctgagagct gaggacacgg ctgtgtatta ctgtgcgaga     360

gattgggccg gggattgtac taatggccaa tgcggcgtct actggggaca gggaaccctg     420

gtcaccgtct cctcaggagg tggcggatct ggtggaggcg gtagcggtgg tggcggatcc     480

gaaattgtgt tgacgcagtc tccactctcc ctgcccgtca cccctggaga gccggcctcc     540

atctcctgca ggtctagtca gagcctcctg catagtaatg gatacaacta tttggattgg     600

tacctgcaga agccagggca gtctccacag ctcctgatct atttgggttc taatcgggcc     660

tccggggtcc ctgacaggtt cagtggcagt ggatcaggca cagattttac actgaaaatc     720

agcagagtgg aggctgagga tgttggggtt tattactgca tgcaagctct acaaactccg     780

tacacttttg gccaggggac caagctggag atcaaacgtg cggccgcaac gaccactcct     840

gcaccccgcc ctccgactcc ggccccaacc attgccagcc agcccctgtc cctgcggccg     900

gaagcctgca gaccggctgc cggcggagcc gtccataccc ggggactgga tttcgcctgc     960

gatatctata tctgggcacc actcgccgga acctgtggag tgctgctgct gtcccttgtg    1020

atcaccctgt actgcaagcg cggacggaag aaactcttgt acatcttcaa gcagccgttc    1080
```

-continued

```
atgcgccctg tgcaaaccac ccaagaagag gacgggtgct cctgccggtt cccggaagag   1140

gaagagggcg gctgcgaact gcgcgtgaag ttttcccggt ccgccgacgc tccggcgtac   1200

cagcaggggc aaaaccagct gtacaacgaa cttaacctcg gtcgccggga agaatatgac   1260

gtgctggaca agcggcgggg aagagatccc gagatgggtg gaaagccgcg gcggaagaac   1320

cctcaggagg gcttgtacaa cgagctgcaa aaggacaaaa tggccgaagc ctactccgag   1380

attggcatga agggagagcg cagacgcggg aagggacacg atggactgta ccagggactg   1440

tcaaccgcga ctaaggacac ttacgacgcc ctgcacatgc aggccctgcc cccgcgc      1497
```

<210> SEQ ID NO 88
<211> LENGTH: 499
<212> TYPE: PRT
<213> ORGANISM: Artificial
<220> FEATURE:
<223> OTHER INFORMATION: D0084 (Ef1a-BCMA sequence 5 CD8 BBz)

<400> SEQUENCE: 88

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Gly Gly
            20                  25                  30

Val Val Gln Pro Gly Gly Ser Leu Arg Leu Ser Cys Ala Ala Ser Gly
        35                  40                  45

Phe Thr Phe Ser Ser Tyr Gly Met His Trp Val Arg Gln Ala Pro Gly
    50                  55                  60

Lys Gly Leu Glu Trp Val Ala Phe Ile Arg Tyr Asp Gly Ser Asn Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Asp Trp Ala Gly Asp Cys Thr Asn
        115                 120                 125

Gly Gln Cys Gly Val Tyr Trp Gly Gln Gly Thr Leu Val Thr Val Ser
    130                 135                 140

Ser Gly Gly Gly Gly Ser Gly Gly Gly Gly Ser Gly Gly Gly Gly Ser
145                 150                 155                 160

Glu Ile Val Leu Thr Gln Ser Pro Leu Ser Leu Pro Val Thr Pro Gly
                165                 170                 175

Glu Pro Ala Ser Ile Ser Cys Arg Ser Ser Gln Ser Leu Leu His Ser
            180                 185                 190

Asn Gly Tyr Asn Tyr Leu Asp Trp Tyr Leu Gln Lys Pro Gly Gln Ser
        195                 200                 205

Pro Gln Leu Leu Ile Tyr Leu Gly Ser Asn Arg Ala Ser Gly Val Pro
    210                 215                 220

Asp Arg Phe Ser Gly Ser Gly Ser Gly Thr Asp Phe Thr Leu Lys Ile
225                 230                 235                 240

Ser Arg Val Glu Ala Glu Asp Val Gly Val Tyr Tyr Cys Met Gln Ala
                245                 250                 255

Leu Gln Thr Pro Tyr Thr Phe Gly Gln Gly Thr Lys Leu Glu Ile Lys
            260                 265                 270

Arg Ala Ala Ala Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
```

```
    290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Leu Tyr Cys Lys Arg Gly Arg Lys Lys Leu
            340                 345                 350

Leu Tyr Ile Phe Lys Gln Pro Phe Met Arg Pro Val Gln Thr Thr Gln
        355                 360                 365

Glu Glu Asp Gly Cys Ser Cys Arg Phe Pro Glu Glu Glu Glu Gly Gly
    370                 375                 380

Cys Glu Leu Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg
```

<210> SEQ ID NO 89
<211> LENGTH: 1473
<212> TYPE: DNA
<213> ORGANISM: Artificial
<220> FEATURE:
<223> OTHER INFORMATION: D0085 (Ef1a-BCMA sequence 16 CD8 BBz)

<400> SEQUENCE: 89

```
atgctgctgc tggtgaccag cctgcttctg tgcgaactgc cgcatccggc gtttctgttg      60

attccggagg tccagctggt gcagtctggg ggaggcgtgg tccagcctgg ggggtccctg     120

agactctcct gtgcagcgtc tggattcacc ttcagtagct atggcatgca ctgggtccgc     180

caggctccag gcaaggggct ggagtgggtg gcatttatac ggtatgatgg aagtaataaa     240

tactacgcag actccgtgaa gggccgattc accatctcca gagacaattc caagaacacg     300

ctgtatctgc aaatgaacag cctgagagct gaggacacgg ctgtgtatta ctgtgcgaga     360

gaccttaatg actacggtga cccacccccct tactggggcc agggaaccct ggtcaccgtc     420

tcctcaggag gtggcggatc tggtggaggc ggtagcggtg gtggcggatc cgacatccag     480

atgacccagt ctccatcctc cctgtctgca tctgtaggag acagagtcac catcacttgc     540

cgggcaagtc agagcattag cagctattta aattggtatc agcagaaacc agggaaagcc     600

cctaagctcc tgatctacga tgcatccaat ttggaaacag gggtctcatc aaggttcagt     660

ggcagtggat ctgggacaga gttcactctc accatcagca gtctgcagcc tgaagatttt     720

gcaacttatt tctgtcaaca gacttacagt cccccgatca ccttcggcca agggacacga     780

ctggagatta aacgagcggc cgcaacgacc actcctgcac cccgccctcc gactccggcc     840

ccaaccattg ccagccagcc cctgtccctg cggccggaag cctgcagacc ggctgccggc     900
```

-continued ggagccgtcc atacccgggg actggatttc gcctgcgata tctatatctg ggcaccactc 960
gccggaacct gtggagtgct gctgctgtcc cttgtgatca ccctgtactg caagcgcgga 1020
cggaagaaac tcttgtacat cttcaagcag ccgttcatgc gccctgtgca aaccacccaa 1080
gaagaggacg ggtgctcctg ccggttcccg gaagaggaag agggcggctg cgaactgcgc 1140
gtgaagtttt cccggtccgc cgacgctccg gcgtaccagc aggggcaaaa ccagctgtac 1200
aacgaactta acctcggtcg ccgggaagaa tatgacgtgc tggacaagcg gcggggaaga 1260
gatcccgaga tgggtggaaa gccgcggcgg aagaaccctc aggagggctt gtacaacgag 1320
ctgcaaaagg acaaaatggc cgaagcctac tccgagattg gcatgaaggg agagcgcaga 1380
cgcgggaagg gacacgatgg actgtaccag ggactgtcaa ccgcgactaa ggacacttac 1440
gacgccctgc acatgcaggc cctgcccccg cgc 1473

<210> SEQ ID NO 90
<211> LENGTH: 491
<212> TYPE: PRT
<213> ORGANISM: Artificial
<220> FEATURE:
<223> OTHER INFORMATION: D0085 (Ef1a-BCMA sequence 16 CD8 BBz)

<400> SEQUENCE: 90

Met Leu Leu Leu Val Thr Ser Leu Leu Leu Cys Glu Leu Pro His Pro
1 5 10 15

Ala Phe Leu Leu Ile Pro Glu Val Gln Leu Val Gln Ser Gly Gly Gly
20 25 30

Val Val Gln Pro Gly Gly Ser Leu Arg Leu Ser Cys Ala Ala Ser Gly
35 40 45

Phe Thr Phe Ser Ser Tyr Gly Met His Trp Val Arg Gln Ala Pro Gly
50 55 60

Lys Gly Leu Glu Trp Val Ala Phe Ile Arg Tyr Asp Gly Ser Asn Lys
65 70 75 80

Tyr Tyr Ala Asp Ser Val Lys Gly Arg Phe Thr Ile Ser Arg Asp Asn
85 90 95

Ser Lys Asn Thr Leu Tyr Leu Gln Met Asn Ser Leu Arg Ala Glu Asp
100 105 110

Thr Ala Val Tyr Tyr Cys Ala Arg Asp Leu Asn Asp Tyr Gly Asp Pro
115 120 125

Pro Pro Tyr Trp Gly Gln Gly Thr Leu Val Thr Val Ser Ser Gly Gly
130 135 140

Gly Gly Ser Gly Gly Gly Gly Ser Gly Gly Gly Gly Ser Asp Ile Gln
145 150 155 160

Met Thr Gln Ser Pro Ser Ser Leu Ser Ala Ser Val Gly Asp Arg Val
165 170 175

Thr Ile Thr Cys Arg Ala Ser Gln Ser Ile Ser Ser Tyr Leu Asn Trp
180 185 190

Tyr Gln Gln Lys Pro Gly Lys Ala Pro Lys Leu Leu Ile Tyr Asp Ala
195 200 205

Ser Asn Leu Glu Thr Gly Val Ser Ser Arg Phe Ser Gly Ser Gly Ser
210 215 220

Gly Thr Glu Phe Thr Leu Thr Ile Ser Ser Leu Gln Pro Glu Asp Phe
225 230 235 240

Ala Thr Tyr Phe Cys Gln Gln Thr Tyr Ser Pro Pro Ile Thr Phe Gly
245 250 255

-continued

```
Gln Gly Thr Arg Leu Glu Ile Lys Arg Ala Ala Ala Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490


<210> SEQ ID NO 91
<211> LENGTH: 1476
<212> TYPE: DNA
<213> ORGANISM: Artificial
<220> FEATURE:
<223> OTHER INFORMATION: D0086 (Ef1a-BCMA sequence 37 CD8 BBz) (Ef1a-
      BCMA sequence 37 CD8 BBz)

<400> SEQUENCE: 91

atgctgctgc tggtgaccag cctgcttctg tgcgaactgc cgcatccggc gtttctgttg      60

attccggagg tgcagctggt ggagtctggg ggaggcttgg tcaagcctgg agggtccctg     120

agactctcct gtgcagcgtc tggattcacc ttcagtagct atggcatgca ctgggtccgc     180

caggctccag gcaaggggct ggagtgggtg gcatttatac ggtatgatgg aagtaataaa     240

tactatgcag actccgtgaa gggccgattc accatctcca gagacaattc caagaacacg     300

ctgtatctgc aaatgaacag cctgagagct gaggacacgg ctgtgtatta ctgtgcgaaa     360

gattgggaat atagtggata cgatgcacac ccgggatggg gtcagggaac cctggtcacc     420

gtctcttcag gaggtggtgg gtctggtgga ggcggtagcg gtggtggcgg atccgacatc     480

cagttgaccc agtctccatc ctccctgtct gcatctgtag gagacagagt caccatcact     540

tgccgggcaa gtcagggcat tagcagtgct ttagcctggt atcagcagaa accagggaaa     600

gctcctaagc tcctgatcta tgatgcctcc agtttggaaa gtggggtccc atcaaggttc     660

agtggcagtg gatctgggac agagttcact ctcaccatca gcagtctgca gcctgaagat     720
```

```
tttgcaactt atttctgtca acagacttac agtcccccga tcaccttcgg ccaagggaca    780

cgactggaga ttaaacgagc ggccgcaacg accactcctg caccccgccc tccgactccg    840

gccccaacca ttgccagcca gcccctgtcc ctgcggccgg aagcctgcag accggctgcc    900

ggcggagccg tccatacccg ggactggat ttcgcctgcg atatctatat ctgggcacca     960

ctcgccggaa cctgtggagt gctgctgctg tcccttgtga tcaccctgta ctgcaagcgc   1020

ggacggaaga aactcttgta catcttcaag cagccgttca tgcgccctgt gcaaaccacc   1080

caagaagagg acgggtgctc ctgccggttc ccggaagagg aagagggcgg ctgcgaactg   1140

cgcgtgaagt tttcccggtc cgccgacgct ccggcgtacc agcaggggca aaaccagctg   1200

tacaacgaac ttaacctcgg tcgccgggaa gaatatgacg tgctggacaa gcggcgggga   1260

agagatcccg agatgggtgg aaagccgcgg cggaagaacc ctcaggaggg cttgtacaac   1320

gagctgcaaa aggacaaaat ggccgaagcc tactccgaga ttggcatgaa gggagagcgc   1380

agacgcggga agggacacga tggactgtac cagggactgt caaccgcgac taaggacact   1440

tacgacgccc tgcacatgca ggccctgccc ccgcgc                             1476
```

```
<210> SEQ ID NO 92
<211> LENGTH: 492
<212> TYPE: PRT
<213> ORGANISM: Artificial
<220> FEATURE:
<223> OTHER INFORMATION: D0086 (Ef1a-BCMA sequence 37 CD8 BBz) (Ef1a-
      BCMA sequence 37 CD8 BBz)

<400> SEQUENCE: 92

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Ser Tyr Gly Met His Trp Val Arg Gln Ala Pro Gly
    50                  55                  60

Lys Gly Leu Glu Trp Val Ala Phe Ile Arg Tyr Asp Gly Ser Asn Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Asp Trp Glu Tyr Ser Gly Tyr Asp
        115                 120                 125

Ala His Pro Gly Trp Gly Gln Gly Thr Leu Val Thr Val Ser Ser Gly
    130                 135                 140

Gly Gly Gly Ser Gly Gly Gly Gly Ser Gly Gly Gly Gly Ser Asp Ile
145                 150                 155                 160

Gln Leu Thr Gln Ser Pro Ser Ser Leu Ser Ala Ser Val Gly Asp Arg
                165                 170                 175

Val Thr Ile Thr Cys Arg Ala Ser Gln Gly Ile Ser Ser Ala Leu Ala
            180                 185                 190

Trp Tyr Gln Gln Lys Pro Gly Lys Ala Pro Lys Leu Leu Ile Tyr Asp
        195                 200                 205

Ala Ser Ser Leu Glu Ser Gly Val Pro Ser Arg Phe Ser Gly Ser Gly
    210                 215                 220
```

```
Ser Gly Thr Glu Phe Thr Leu Thr Ile Ser Ser Leu Gln Pro Glu Asp
225                 230                 235                 240

Phe Ala Thr Tyr Phe Cys Gln Gln Thr Tyr Ser Pro Pro Ile Thr Phe
                245                 250                 255

Gly Gln Gly Thr Arg Leu Glu Ile Lys Arg Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490


<210> SEQ ID NO 93
<211> LENGTH: 1479
<212> TYPE: DNA
<213> ORGANISM: Artificial
<220> FEATURE:
<223> OTHER INFORMATION: D0087_LTG2092 (Ef1a-BCMA sequence 40 CD8 BBz)

<400> SEQUENCE: 93

atgctgctgc tggtgaccag cctgcttctg tgcgaactgc cgcatccggc gtttcttctg      60

attccggagg tgcagctggt gcagtctggg ggaggcgtgg tccagcctgg ggggtccctg     120

agactctcct gtgcagcgtc tggattcacc ttcagtagct atggcatgca ctgggtccgc     180

caggctccag gcaaggggct ggagtgggtg gcatttatac ggtatgatgg aagtaataaa     240

tactacgcag actccgtgaa gggccgattc accatctcca gagacaattc caagaacacg     300

ctgtatctgc aaatgaacag cctgagagct gaggacacgg ctgtgtatta ctgtgcgaaa     360

gaaccccccg agtattacta tgatagtagt ggttattcgt ggggccaggg aaccctggtc     420

accgtctcct caggaggtgg cgggtctggt ggaggcggta gcggtggtgg cggatccgac     480

atccagttga cccagtctcc atcctccctg tctgcatctg taggagacag agtcaccatc     540
```

-continued

```
acttgccagg cgagtcagga cattgacacc tatttaaact ggtatcagca gaaaccaggg    600

aaagccccta agctcctgat ctatgctgca tccagtttgc aaagtggggt ctcatcaagg    660

ttcagtggca gtggatctgg gacagagttc actctcacca tcagcagtct gcagcctgaa    720

gattttgcaa cttatttctg tcaacagact tacagtcccc cgatcacctt cggccaaggg    780

acacgactgg agattaaacg agcggccgca acgaccactc ctgcaccccg ccctccgact    840

ccggccccaa ccattgccag ccagcccctg tccctgcggc cggaagcctg cagaccggct    900

gccggcggag ccgtccatac ccggggactg gatttcgcct gcgatatcta tatctgggca    960

ccactcgccg gaacctgtgg agtgctgctg ctgtcccttg tgatcaccct gtactgcaag   1020

cgcggacgga agaaactctt gtacatcttc aagcagccgt tcatgcgccc tgtgcaaacc   1080

acccaagaag aggacgggtg ctcctgccgg ttcccggaag aggaagaggg cggctgcgaa   1140

ctgcgcgtga agttttcccg gtccgccgac gctccggcgt accagcaggg gcaaaaccag   1200

ctgtacaacg aacttaacct cggtcgccgg gaagaatatg acgtgctgga caagcggcgg   1260

ggaagagatc ccgagatggg tggaaagccg cggcggaaga accctcagga gggcttgtac   1320

aacgagctgc aaaaggacaa aatggccgaa gcctactccg agattggcat gaagggagag   1380

cgcagacgcg ggaagggaca cgatggactg taccagggac tgtcaaccgc gactaaggac   1440

acttacgacg ccctgcacat gcaggccctg cccccgcgc                           1479
```

```
<210> SEQ ID NO 94
<211> LENGTH: 493
<212> TYPE: PRT
<213> ORGANISM: Artificial
<220> FEATURE:
<223> OTHER INFORMATION: D0087_LTG2092 (Ef1a-BCMA sequence 40 CD8 BBz)

<400> SEQUENCE: 94

Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Gly Gly
            20                  25                  30

Val Val Gln Pro Gly Gly Ser Leu Arg Leu Ser Cys Ala Ala Ser Gly
        35                  40                  45

Phe Thr Phe Ser Ser Tyr Gly Met His Trp Val Arg Gln Ala Pro Gly
    50                  55                  60

Lys Gly Leu Glu Trp Val Ala Phe Ile Arg Tyr Asp Gly Ser Asn Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Glu Pro Pro Glu Tyr Tyr Tyr Asp
        115                 120                 125

Ser Ser Gly Tyr Ser Trp Gly Gln Gly Thr Leu Val Thr Val Ser Ser
    130                 135                 140

Gly Gly Gly Gly Ser Gly Gly Gly Gly Ser Gly Gly Gly Gly Ser Asp
145                 150                 155                 160

Ile Gln Leu Thr Gln Ser Pro Ser Ser Leu Ser Ala Ser Val Gly Asp
                165                 170                 175

Arg Val Thr Ile Thr Cys Gln Ala Ser Gln Asp Ile Asp Thr Tyr Leu
            180                 185                 190
```

-continued

```
Asn Trp Tyr Gln Gln Lys Pro Gly Lys Ala Pro Lys Leu Leu Ile Tyr
        195                 200                 205

Ala Ala Ser Ser Leu Gln Ser Gly Val Ser Ser Arg Phe Ser Gly Ser
    210                 215                 220

Gly Ser Gly Thr Glu Phe Thr Leu Thr Ile Ser Ser Leu Gln Pro Glu
225                 230                 235                 240

Asp Phe Ala Thr Tyr Phe Cys Gln Gln Thr Tyr Ser Pro Pro Ile Thr
                245                 250                 255

Phe Gly Gln Gly Thr Arg Leu Glu Ile Lys Arg Ala Ala Ala Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 95
<211> LENGTH: 1476
<212> TYPE: DNA
<213> ORGANISM: Artificial
<220> FEATURE:
<223> OTHER INFORMATION: D0099_LTG2944 (Ef1a-BCMA sequence 4-12 CD8 BBz)

<400> SEQUENCE: 95

```
atgctgctgc tggtgaccag cctgctgctg tgcgaactgc cgcatccggc gtttctgctg     60

attccgcagg tgcagctggt gcagtctggg ggaggcgtgg tccagcctgg ggggtccctg    120

agactctcct gtgcagcctc tggattcacc ttcagtagtt acgttataca ttgggtccgc    180

caggctccag gcaaggggct ggagtgggtg gcagctatat cgcatgatgg aagcaataaa    240

tactacgcag actccgtgaa gggccgattc accatctcca gagacaattc caagaacacg    300

ctgtatcttc aaatgagcag tctgagcgct gaggacacgg ctatgtatta ctgtgtgaaa    360
```

-continued

```
actagtagtg attattacta cgcctactgg ggccagggaa ccctggtcac cgtctcctca    420

ggaggtggcg ggtctggtgg aggcggtagc ggtggtggcg gatcccagac tgtggtgact    480

caggagccat cgttctcagt gtcccctgga gggacagtca cactcacttg tggcttgagc    540

tctggctcag tctctactgg caactccccc acctggtacc agcagacccc aggccaggct    600

ccacgcacgc tcatctacag cacaaacact cgctcttctg ggtccctga tcgcttctct     660

ggctccatcc ttgggaacaa agctgccctc accatcacgg gggcccaggc agatgatgaa    720

tctgattatt actgtgtgct gtatatgggt agtggctatt gggtgttcgg cggagggacc    780

aaggtcaccg tcctaggtgc ggccgcaacg accactcctg caccccgccc tccgactccg    840

gccccaacca ttgccagcca gcccctgtcc ctgcggccgg aagcctgcag accggctgcc    900

ggcggagccg tccatacccg gggactggat ttcgcctgcg atatctatat ctgggcacca    960

ctcgccggaa cctgtggagt gctgctgctg tcccttgtga tcaccctgta ctgcaagcgc   1020

ggacggaaga aactcttgta catcttcaag cagccgttca tgcgccctgt gcaaaccacc   1080

caagaagagg acgggtgctc ctgccggttc ccggaagagg aagagggcgg ctgcgaactg   1140

cgcgtgaagt tttcccggtc cgccgacgct ccggcgtacc agcaggggca aaaccagctg   1200

tacaacgaac ttaacctcgg tcgccgggaa gaatatgacg tgctggacaa gcggcgggga   1260

agagatcccg agatgggtgg aaagccgcgg cggaagaacc ctcaggaggg cttgtacaac   1320

gagctgcaaa aggacaaaat ggccgaagcc tactccgaga ttggcatgaa gggagagcgc   1380

agacgcggga agggacacga tggactgtac cagggactgt caaccgcgac taaggacact   1440

tacgacgccc tgcacatgca ggccctgccc ccgcgc                             1476
```

```
<210> SEQ ID NO 96
<211> LENGTH: 492
<212> TYPE: PRT
<213> ORGANISM: Artificial
<220> FEATURE:
<223> OTHER INFORMATION: D0099_LTG2944 (Ef1a-BCMA sequence 4-12 CD8 BBz)

<400> SEQUENCE: 96

Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Gly Gly
            20                  25                  30

Val Val Gln Pro Gly Gly Ser Leu Arg Leu Ser Cys Ala Ala Ser Gly
        35                  40                  45

Phe Thr Phe Ser Ser Tyr Val Ile His Trp Val Arg Gln Ala Pro Gly
    50                  55                  60

Lys Gly Leu Glu Trp Val Ala Ala Ile Ser His Asp Gly Ser Asn Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Ser Ser Leu Ser Ala Glu Asp
            100                 105                 110

Thr Ala Met Tyr Tyr Cys Val Lys Thr Ser Ser Asp Tyr Tyr Tyr Ala
        115                 120                 125

Tyr Trp Gly Gln Gly Thr Leu Val Thr Val Ser Ser Gly Gly Gly Gly
    130                 135                 140

Ser Gly Gly Gly Gly Ser Gly Gly Gly Gly Ser Gln Thr Val Val Thr
145                 150                 155                 160

Gln Glu Pro Ser Phe Ser Val Ser Pro Gly Gly Thr Val Thr Leu Thr
```

```
                165                 170                 175

Cys Gly Leu Ser Ser Gly Ser Val Ser Thr Gly Asn Ser Pro Thr Trp
            180                 185                 190

Tyr Gln Gln Thr Pro Gly Gln Ala Pro Arg Thr Leu Ile Tyr Ser Thr
        195                 200                 205

Asn Thr Arg Ser Ser Gly Val Pro Asp Arg Phe Ser Gly Ser Ile Leu
    210                 215                 220

Gly Asn Lys Ala Ala Leu Thr Ile Thr Gly Ala Gln Ala Asp Asp Glu
225                 230                 235                 240

Ser Asp Tyr Tyr Cys Val Leu Tyr Met Gly Ser Gly Tyr Trp Val Phe
                245                 250                 255

Gly Gly Gly Thr Lys Val Thr Val Leu Gly Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490


<210> SEQ ID NO 97
<211> LENGTH: 1467
<212> TYPE: DNA
<213> ORGANISM: Artificial
<220> FEATURE:
<223> OTHER INFORMATION: D0100_LTG2945 (Ef1a-BCMA sequence 4-45 CD8 BBz)

<400> SEQUENCE: 97

atgctgctgc tggtgaccag cctgctgctg tgcgaactgc cgcatccggc gtttctgctg      60

attccggagg tgcagctggt gcagtctggg gctgaggtga agaagcctgg ggcctcagtg     120

aaggtttcct gcaaggcatc tggatacacc tccaccagct actatatgca ctgggtgcga     180

caggcccctg gacaagggct tgagtggatg ggaataatca accctagtgg tggtagcaca     240
```

```
agctacgcac agaagttcca gggcagagtc accatgacca gggacacgtc cacgagcaca    300

gtctacatgg agctgagcag cttgagatct gaggacacgg ccgtgtatta ctgtgcgaga    360

gatttgggtg atggcgcttt tgatatctgg ggccaaggga caatggtcac cgtctcttca    420

ggaggtggcg ggtctggtgg aggcggtagc ggtggtggcg gatccgacat ccagatgacc    480

cagtctctat cctccctgtc tgcatctgta ggagacagag tcaccatcgc ttgccgggca    540

agtcagacca ttagtaggta tttaaattgg tatcagcaga aaccagggaa agcccctaag    600

ctcctgatct atgctgcatc cagtttgcaa agtggggtct catcaaggtt cagtggcagt    660

ggatctggga cagagttcac tctcaccatc agcagtctgc agcctgaaga ttttgcaact    720

tatttctgtc aacagactta cagtcccccg atcaccttcg gccaagggac acgactggag    780

attaaacgag cggccgcaac gaccactcct gcaccccgcc ctccgactcc ggccccaacc    840

attgccagcc agcccctgtc cctgcggccg gaagcctgca gaccggctgc cggcggagcc    900

gtccataccc ggggactgga tttcgcctgc gatatctata tctgggcacc actcgccgga    960

acctgtggag tgctgctgct gtcccttgtg atcaccctgt actgcaagcg cggacggaag   1020

aaactcttgt acatcttcaa gcagccgttc atgcgccctg tgcaaaccac ccaagaagag   1080

gacgggtgct cctgccggtt cccggaagag gaagagggcg gctgcgaact gcgcgtgaag   1140

ttttcccggt ccgccgacgc tccggcgtac cagcaggggc aaaaccagct gtacaacgaa   1200

cttaacctcg gtcgccggga agaatatgac gtgctggaca agcggcgggg aagagatccc   1260

gagatgggtg gaaagccgcg gcggaagaac cctcaggagg gcttgtacaa cgagctgcaa   1320

aaggacaaaa tggccgaagc ctactccgag attggcatga agggagagcg cagacgcggg   1380

aagggacacg atggactgta ccagggactg tcaaccgcga ctaaggacac ttacgacgcc   1440

ctgcacatgc aggccctgcc cccgcgc                                       1467
```

<210> SEQ ID NO 98
<211> LENGTH: 489
<212> TYPE: PRT
<213> ORGANISM: Artificial
<220> FEATURE:
<223> OTHER INFORMATION: D0100_LTG2945 (Ef1a-BCMA sequence 4-45 CD8 BBz)

<400> SEQUENCE: 98

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Ser Thr Ser Tyr Tyr Met His Trp Val Arg Gln Ala Pro Gly
    50                  55                  60

Gln Gly Leu Glu Trp Met Gly Ile Ile Asn Pro Ser Gly Gly Ser Thr
65                  70                  75                  80

Ser Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Asp Leu Gly Asp Gly Ala Phe Asp
        115                 120                 125

Ile Trp Gly Gln Gly Thr Met Val Thr Val Ser Ser Gly Gly Gly Gly
    130                 135                 140
```

```
Ser Gly Gly Gly Gly Ser Gly Gly Gly Gly Ser Asp Ile Gln Met Thr
145                 150                 155                 160

Gln Ser Leu Ser Ser Leu Ser Ala Ser Val Gly Asp Arg Val Thr Ile
                165                 170                 175

Ala Cys Arg Ala Ser Gln Thr Ile Ser Arg Tyr Leu Asn Trp Tyr Gln
            180                 185                 190

Gln Lys Pro Gly Lys Ala Pro Lys Leu Leu Ile Tyr Ala Ala Ser Ser
        195                 200                 205

Leu Gln Ser Gly Val Ser Ser Arg Phe Ser Gly Ser Gly Ser Gly Thr
    210                 215                 220

Glu Phe Thr Leu Thr Ile Ser Ser Leu Gln Pro Glu Asp Phe Ala Thr
225                 230                 235                 240

Tyr Phe Cys Gln Gln Thr Tyr Ser Pro Pro Ile Thr Phe Gly Gln Gly
                245                 250                 255

Thr Arg Leu Glu Ile Lys Arg Ala Ala Ala Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485
```

<210> SEQ ID NO 99
<211> LENGTH: 1485
<212> TYPE: DNA
<213> ORGANISM: Artificial
<220> FEATURE:
<223> OTHER INFORMATION: D0153 (BCMA 4-1c CD8 BBz)

<400> SEQUENCE: 99

```
atgctgctgc tggtgaccag cctgctgctg tgcgaactgc cgcatccggc gtttctgctg      60
```

-continued

```
attccggagg tgcagctggt ggagaccggg ggaggcgtgg tccagcctgg ggggtccctg    120
agactctcct gtgcagcgtc tggattcacc ttcagtagct atggcatgca ctgggtccgc    180
caggctccag gcaaggggct ggagtgggtg gcatttatac ggtatgatgg aagtaataaa    240
tactacgcag actccgtgaa gggccgattc accatctcca gagacaattc caagaacacg    300
ctgtatctgc aaatgaacag cctgagagct gaggacacgg ctgtgtatta ctgtgcgaaa    360
gattgggata cgtattacta tgatagtagt ggttatgatc gggcctgggg ccagggaacc    420
ctggtcaccg tctcctcagg aggtggcggg tctggtggag gcggtagcgg tggtggcgga    480
tccgacatcc agatgaccca gtctccctcc tccctgtctg catctgtagg agacagagtc    540
accatcactt gccaggcgag tcaggacatt aacaactatt taaattggta tcagcagaaa    600
ccagggaaag cccctaagct cctgatctat gctgcatcca gtttgcaaag tggggtctca    660
tcaaggttca gtggcagtgg atctgggaca gagttcactc tcaccatcag cagtctgcag    720
cctgaagatt ttgcaactta tttctgtcaa cagacttaca gtcccccgat caccttcggc    780
caagggacac gactggagat taaacgagcg gccgcaacga ccactcctgc accccgccct    840
ccgactccgg ccccaaccat tgccagccag cccctgtccc tgcggccgga agcctgcaga    900
ccggctgccg gcggagccgt ccatacccgg ggactggatt tcgcctgcga tatctatatc    960
tgggcaccac tcgccggaac ctgtggagtg ctgctgctgt cccttgtgat caccctgtac   1020
tgcaagcgcg gacggaagaa actcttgtac atcttcaagc agccgttcat gcgccctgtg   1080
caaaccaccc aagaagagga cgggtgctcc tgccggttcc cggaagagga agagggcggc   1140
tgcgaactgc gcgtgaagtt ttcccggtcc gccgacgctc cggcgtacca gcaggggcaa   1200
aaccagctgt acaacgaact taacctcggt cgccgggaag aatatgacgt gctggacaag   1260
cggcggggaa gagatcccga gatgggtgga aagccgcggc ggaagaaccc tcaggagggc   1320
ttgtacaacg agctgcaaaa ggacaaaatg gccgaagcct actccgagat tggcatgaag   1380
ggagagcgca gacgcgggaa gggacacgat ggactgtacc agggactgtc aaccgcgact   1440
aaggacactt acgacgccct gcacatgcag gccctgcccc cgcgc                   1485
```

<210> SEQ ID NO 100
<211> LENGTH: 495
<212> TYPE: PRT
<213> ORGANISM: Artificial
<220> FEATURE:
<223> OTHER INFORMATION: D0153 (BCMA 4-1c CD8 BBz)

<400> SEQUENCE: 100

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Thr Gly Gly Gly
            20                  25                  30

Val Val Gln Pro Gly Gly Ser Leu Arg Leu Ser Cys Ala Ala Ser Gly
        35                  40                  45

Phe Thr Phe Ser Ser Tyr Gly Met His Trp Val Arg Gln Ala Pro Gly
    50                  55                  60

Lys Gly Leu Glu Trp Val Ala Phe Ile Arg Tyr Asp Gly Ser Asn Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110
```

-continued

```
Thr Ala Val Tyr Tyr Cys Ala Lys Asp Trp Asp Thr Tyr Tyr Tyr Asp
        115                 120                 125

Ser Ser Gly Tyr Asp Arg Ala Trp Gly Gln Gly Thr Leu Val Thr Val
    130                 135                 140

Ser Ser Gly Gly Gly Gly Ser Gly Gly Gly Gly Ser Gly Gly Gly Gly
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Gln Ala Ser Gln Asp Ile Asn Asn
            180                 185                 190

Tyr Leu Asn Trp Tyr Gln Gln Lys Pro Gly Lys Ala Pro Lys Leu Leu
        195                 200                 205

Ile Tyr Ala Ala Ser Ser Leu Gln Ser Gly Val Ser Ser Arg Phe Ser
    210                 215                 220

Gly Ser Gly Ser Gly Thr Glu Phe Thr Leu Thr Ile Ser Ser Leu Gln
225                 230                 235                 240

Pro Glu Asp Phe Ala Thr Tyr Phe Cys Gln Gln Thr Tyr Ser Pro Pro
                245                 250                 255

Ile Thr Phe Gly Gln Gly Thr Arg Leu Glu Ile Lys Arg Ala Ala Ala
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495
```

<210> SEQ ID NO 101
<211> LENGTH: 2142
<212> TYPE: DNA
<213> ORGANISM: Artificial
<220> FEATURE:
<223> OTHER INFORMATION: D158 (BCMA 4-45 CD8 BBz 2A TGFBRIIdn)

<400> SEQUENCE: 101

```
atgctgctgc tggtgaccag cctgctgctg tgcgaactgc cgcatccggc gtttctgctg     60
attccggagg tgcagctggt gcagtctggg gctgaggtga agaagcctgg ggcctcagtg    120
aaggtttcct gcaaggcatc tggatacacc tccaccagct actatatgca ctgggtgcga    180
caggcccctg gacaagggct tgagtggatg ggaataatca accctagtgg tggtagcaca    240
agctacgcac agaagttcca gggcagagtc accatgacca gggacacgtc cacgagcaca    300
gtctacatgg agctgagcag cttgagatct gaggacacgg ccgtgtatta ctgtgcgaga    360
gatttgggtg atggcgcttt tgatatctgg ggccaaggga caatggtcac cgtctcttca    420
ggaggtggcg ggtctggtgg aggcggtagc ggtggtggcg gatccgacat ccagatgacc    480
cagtctctat cctccctgtc tgcatctgta ggagacagag tcaccatcgc ttgccgggca    540
agtcagacca ttagtaggta tttaaattgg tatcagcaga aaccagggaa agcccctaag    600
ctcctgatct atgctgcatc cagtttgcaa agtggggtct catcaaggtt cagtggcagt    660
ggatctggga cagagttcac tctcaccatc agcagtctgc agcctgaaga ttttgcaact    720
tatttctgtc aacagactta cagtcccccg atcaccttcg gccaagggac acgactggag    780
attaaacgag cggccgctac cacaacccct gcgccccggc ctcctacccc cgcacccacg    840
attgcttctc aacctctttc actccgacct gaggcttgta gacctgcagc cgggggtgcc    900
gtccacacac ggggactcga cttcgcttgt gatatatata tttgggcgcc cctggccggc    960
acttgtggag ttcttttgct ctctcttgtt atcacattgt actgcaagcg aggtaggaag   1020
aaattgcttt acatttttaa gcagccgttc atgcgaccag tacagactac tcaagaagaa   1080
gatgggtgct cttgtcggtt cccggaagaa gaagagggtg gttgcgagtt gagggtgaag   1140
ttctcccgct ctgccgacgc accggcatat cagcagggac aaaaccagct ctacaacgaa   1200
ttgaacctgg gtcggcggga agaatatgac gtgctcgata agcggcgggg tcgcgaccca   1260
gaaatgggag gcaaaccgcg caggaaaaat ccacaggagg gactttataa cgaacttcaa   1320
aaggataaga tggcagaggc atacagcgaa atcgggatga aaggcgagag aagaaggggg   1380
aaagggcacg atggtcttta ccaggggctt tctaccgcga cgaaggatac ctacgatgct   1440
ctccatatgc aagcacttcc tcctagacgg gcaaagcggg gctcaggggc gactaacttt   1500
tcactgttga agcaggccgg ggatgtggag gagaatcctg gtcctagagc taagcgagta   1560
gacatgggaa gagggctgct ccgaggcttg tggccgttgc atattgtatt gtggacgcgg   1620
atagcgagta caatcccgcc tcacgtgcaa aaatcagtta ataacgacat gatcgttact   1680
gacaacaatg gcgcagttaa atttccgcag ctttgtaaat tctgtgatgt aagattttca   1740
acgtgcgata accagaaaag ctgtatgtcc aactgcagca tcacatcaat ctgtgaaaaa   1800
ccccaagagg tatgtgtggc cgtctggcga aagaatgacg aaaatatcac actggagacc   1860
gtttgtcacg atcctaaact cccttatcat gactttattc tggaagacgc agcgtcaccg   1920
aagtgtataa tgaaagagaa gaagaagcct ggagagacgt tttcatgtg cagttgctcc    1980
tcagatgagt gtaatgacaa catcattttt tccgaggagt acaatacgag taacccagac   2040
ctcctgctgg ttattttcca ggtaaccggc atcagtttgt tgcccccact gggtgttgca   2100
atcagtgtaa taatcatatt ttattgttac cgggtgtgat aa                      2142
```

<210> SEQ ID NO 102
<211> LENGTH: 712
<212> TYPE: PRT

<213> ORGANISM: Artificial
<220> FEATURE:
<223> OTHER INFORMATION: D158 (BCMA 4-45 CD8 BBz 2A TGFBRIIdn)

<400> SEQUENCE: 102

Met Leu Leu Leu Val Thr Ser Leu Leu Leu Cys Glu Leu Pro His Pro
1 5 10 15

Ala Phe Leu Leu Ile Pro Glu Val Gln Leu Val Gln Ser Gly Ala Glu
20 25 30

Val Lys Lys Pro Gly Ala Ser Val Lys Val Ser Cys Lys Ala Ser Gly
35 40 45

Tyr Thr Ser Thr Ser Tyr Tyr Met His Trp Val Arg Gln Ala Pro Gly
50 55 60

Gln Gly Leu Glu Trp Met Gly Ile Ile Asn Pro Ser Gly Gly Ser Thr
65 70 75 80

Ser Tyr Ala Gln Lys Phe Gln Gly Arg Val Thr Met Thr Arg Asp Thr
85 90 95

Ser Thr Ser Thr Val Tyr Met Glu Leu Ser Ser Leu Arg Ser Glu Asp
100 105 110

Thr Ala Val Tyr Tyr Cys Ala Arg Asp Leu Gly Asp Gly Ala Phe Asp
115 120 125

Ile Trp Gly Gln Gly Thr Met Val Thr Val Ser Ser Gly Gly Gly Gly
130 135 140

Ser Gly Gly Gly Gly Ser Gly Gly Gly Gly Ser Asp Ile Gln Met Thr
145 150 155 160

Gln Ser Leu Ser Ser Leu Ser Ala Ser Val Gly Asp Arg Val Thr Ile
165 170 175

Ala Cys Arg Ala Ser Gln Thr Ile Ser Arg Tyr Leu Asn Trp Tyr Gln
180 185 190

Gln Lys Pro Gly Lys Ala Pro Lys Leu Leu Ile Tyr Ala Ala Ser Ser
195 200 205

Leu Gln Ser Gly Val Ser Ser Arg Phe Ser Gly Ser Gly Ser Gly Thr
210 215 220

Glu Phe Thr Leu Thr Ile Ser Ser Leu Gln Pro Glu Asp Phe Ala Thr
225 230 235 240

Tyr Phe Cys Gln Gln Thr Tyr Ser Pro Pro Ile Thr Phe Gly Gln Gly
245 250 255

Thr Arg Leu Glu Ile Lys Arg Ala Ala Ala Thr Thr Thr Pro Ala Pro
260 265 270

Arg Pro Pro Thr Pro Ala Pro Thr Ile Ala Ser Gln Pro Leu Ser Leu
275 280 285

Arg Pro Glu Ala Cys Arg Pro Ala Ala Gly Gly Ala Val His Thr Arg
290 295 300

Gly Leu Asp Phe Ala Cys Asp Ile Tyr Ile Trp Ala Pro Leu Ala Gly
305 310 315 320

Thr Cys Gly Val Leu Leu Leu Ser Leu Val Ile Thr Leu Tyr Cys Lys
325 330 335

Arg Gly Arg Lys Lys Leu Leu Tyr Ile Phe Lys Gln Pro Phe Met Arg
340 345 350

Pro Val Gln Thr Thr Gln Glu Glu Asp Gly Cys Ser Cys Arg Phe Pro
355 360 365

Glu Glu Glu Glu Gly Gly Cys Glu Leu Arg Val Lys Phe Ser Arg Ser
370 375 380

Ala Asp Ala Pro Ala Tyr Gln Gln Gly Gln Asn Gln Leu Tyr Asn Glu

-continued

```
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg Arg Ala Lys Arg Gly Ser Gly
                485                 490                 495

Ala Thr Asn Phe Ser Leu Leu Lys Gln Ala Gly Asp Val Glu Glu Asn
            500                 505                 510

Pro Gly Pro Arg Ala Lys Arg Val Asp Met Gly Arg Gly Leu Leu Arg
        515                 520                 525

Gly Leu Trp Pro Leu His Ile Val Leu Trp Thr Arg Ile Ala Ser Thr
    530                 535                 540

Ile Pro Pro His Val Gln Lys Ser Val Asn Asn Asp Met Ile Val Thr
545                 550                 555                 560

Asp Asn Asn Gly Ala Val Lys Phe Pro Gln Leu Cys Lys Phe Cys Asp
                565                 570                 575

Val Arg Phe Ser Thr Cys Asp Asn Gln Lys Ser Cys Met Ser Asn Cys
            580                 585                 590

Ser Ile Thr Ser Ile Cys Glu Lys Pro Gln Glu Val Cys Val Ala Val
        595                 600                 605

Trp Arg Lys Asn Asp Glu Asn Ile Thr Leu Glu Thr Val Cys His Asp
    610                 615                 620

Pro Lys Leu Pro Tyr His Asp Phe Ile Leu Glu Asp Ala Ala Ser Pro
625                 630                 635                 640

Lys Cys Ile Met Lys Glu Lys Lys Lys Pro Gly Glu Thr Phe Phe Met
                645                 650                 655

Cys Ser Cys Ser Ser Asp Glu Cys Asn Asp Asn Ile Ile Phe Ser Glu
            660                 665                 670

Glu Tyr Asn Thr Ser Asn Pro Asp Leu Leu Leu Val Ile Phe Gln Val
        675                 680                 685

Thr Gly Ile Ser Leu Leu Pro Pro Leu Gly Val Ala Ile Ser Val Ile
    690                 695                 700

Ile Ile Phe Tyr Cys Tyr Arg Val
705                 710
```

<210> SEQ ID NO 103
<211> LENGTH: 372
<212> TYPE: DNA
<213> ORGANISM: Artificial
<220> FEATURE:
<223> OTHER INFORMATION: Binder 4-1c VH

<400> SEQUENCE: 103

```
gaggtgcagc tggtggagac cgggggaggc gtggtccagc ctgggggtc cctgagactc     60

tcctgtgcag cgtctggatt caccttcagt agctatggca tgcactgggt ccgccaggct    120

ccaggcaagg ggctggagtg ggtggcattt atacggtatg atggaagtaa taaatactac    180

gcagactccg tgaagggccg attcaccatc tccagagaca attccaagaa cacgctgtat    240
```

ctgcaaatga acagcctgag agctgaggac acggctgtgt attactgtgc gaaagattgg 300
gatacgtatt actatgatag tagtggttat gatcgggcct ggggccaggg aaccctggtc 360
accgtctcct ca 372

<210> SEQ ID NO 104
<211> LENGTH: 124
<212> TYPE: PRT
<213> ORGANISM: Artificial
<220> FEATURE:
<223> OTHER INFORMATION: Binder 4-1c VH

<400> SEQUENCE: 104

Glu Val Gln Leu Val Glu Thr Gly Gly Gly Val Val Gln Pro Gly Gly
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Phe Ile Arg Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Trp Asp Thr Tyr Tyr Tyr Asp Ser Ser Gly Tyr Asp Arg
100 105 110

Ala Trp Gly Gln Gly Thr Leu Val Thr Val Ser Ser
115 120

<210> SEQ ID NO 105
<211> LENGTH: 326
<212> TYPE: DNA
<213> ORGANISM: Artificial
<220> FEATURE:
<223> OTHER INFORMATION: Binder 4-1c VL

<400> SEQUENCE: 105
gacatccaga tgacccagtc tccctcctcc ctgtctgcat ctgtaggaga cagagtcacc 60
atcacttgcc aggcgagtca ggacattaac aactatttaa attggtatca gcagaaacca 120
gggaaagccc ctaagctcct gatctatgct gcatccagtt tgcaaagtgg ggtctcatca 180
aggttcagtg gcagtggatc tgggacagag ttcactctca ccatcagcag tctgcagcct 240
gaagattttg caacttattt ctgtcaacag acttacagtc ccccgatcac cttcggccaa 300
gggacacgac tggagattaa acgagc 326

<210> SEQ ID NO 106
<211> LENGTH: 108
<212> TYPE: PRT
<213> ORGANISM: Artificial
<220> FEATURE:
<223> OTHER INFORMATION: Binder 4-1c VL

<400> SEQUENCE: 106

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Asn Asn Tyr
20 25 30

```
Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Ser Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Thr Tyr Ser Pro Pro Ile
                85                  90                  95

Thr Phe Gly Gln Gly Thr Arg Leu Glu Ile Lys Arg
            100                 105


<210> SEQ ID NO 107
<211> LENGTH: 90
<212> TYPE: DNA
<213> ORGANISM: Artificial
<220> FEATURE:
<223> OTHER INFORMATION: Furin P2A Furin

<400> SEQUENCE: 107

cgggcaaagc ggggctcagg ggcgactaac ttttcactgt tgaagcaggc cggggatgtg      60

gaggagaatc ctggtcctag agctaagcga                                        90


<210> SEQ ID NO 108
<211> LENGTH: 30
<212> TYPE: PRT
<213> ORGANISM: Artificial
<220> FEATURE:
<223> OTHER INFORMATION: Furin P2A Furin

<400> SEQUENCE: 108

Arg Ala Lys Arg Gly Ser Gly Ala Thr Asn Phe Ser Leu Leu Lys Gln
1               5                   10                  15

Ala Gly Asp Val Glu Glu Asn Pro Gly Pro Arg Ala Lys Arg
            20                  25                  30


<210> SEQ ID NO 109
<211> LENGTH: 573
<212> TYPE: DNA
<213> ORGANISM: Artificial
<220> FEATURE:
<223> OTHER INFORMATION: TGFBRIIdn

<400> SEQUENCE: 109

atgggaagag ggctgctccg aggcttgtgg ccgttgcata ttgtattgtg gacgcggata      60

gcgagtacaa tcccgcctca cgtgcaaaaa tcagttaata acgacatgat cgttactgac     120

aacaatggcg cagttaaatt tccgcagctt tgtaaattct gtgatgtaag attttcaacg     180

tgcgataacc agaaaagctg tatgtccaac tgcagcatca catcaatctg tgaaaaaccc     240

caagaggtat gtgtggccgt ctggcgaaag aatgacgaaa atatcacact ggagaccgtt     300

tgtcacgatc ctaaactccc ttatcatgac tttattctgg aagacgcagc gtcaccgaag     360

tgtataatga aagagaagaa gaagcctgga gagacgtttt tcatgtgcag ttgctcctca     420

gatgagtgta atgacaacat catttttcc gaggagtaca atacgagtaa cccagacctc     480

ctgctggtta ttttccaggt aaccggcatc agtttgttgc ccccactggg tgttgcaatc     540

agtgtaataa tcatatttta ttgttaccgg gtg                                   573


<210> SEQ ID NO 110
<211> LENGTH: 191
<212> TYPE: PRT
```

-continued

```
<213> ORGANISM: Artificial
<220> FEATURE:
<223> OTHER INFORMATION: TGFBRIIdn

<400> SEQUENCE: 110

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val
            180                 185                 190
```

COMPOSITIONS AND METHODS FOR TREATING CANCER WITH ANTI-BCMA IMMUNOTHERAPY

CROSS-REFERENCE TO RELATED APPLICATIONS

This application is a continuation of U.S. patent application Ser. No. 16/888,020, filed May 29, 2020, which claims priority to U.S. Provisional Patent Application Ser. No. 62/854,574, filed on May 30, 2019, the entire contents of which are hereby incorporated by reference.

SEQUENCE LISTING

The instant application contains a Sequence Listing which has been submitted electronically in ASCII format and is hereby incorporated by reference in its entirety. Said ASCII copy, created on May 28, 2020, is named Sequence_Listing.txt and is 146 kilobytes in size.

FIELD OF THE DISCLOSURE

This application relates to the field of cancer, particularly to B-cell maturation antigen (BCMA) antigen binding domains and chimeric antigen receptors (CARs) containing such BCMA antigen binding domains and methods of use thereof.

BACKGROUND

Cancer is one of the most deadly threats to human health. In the U.S. alone, cancer affects nearly 1.3 million new patients each year, and is the second leading cause of death after cardiovascular disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making treatment extremely difficult.

Multiple myeloma (MM) the second most common blood cancer in the US (after non-Hodgkin's lymphoma), with overall 5-year survival rate of approximately 50%, whereas types of genetic abnormalities determine the aggressiveness of MM, and older age at diagnosis, higher disease stage, and metastatic disease are associated with lower chances for survival (www.cancer.net).

MM is a multi-organ disease. In MM, the overgrowth of plasma cells in the bone marrow results in diminished normal hematopoiesis, leading to anemia, thromvocytopenia, and susceptibility to infections. Myeloma cells promote bone resorption by osteoclasts, leading to bone pain, bone loss, osteoporosis, fractions, and elevated blood calcium. Secretion of high level monoclonal immunoglobulins by myeloma cells leads to kidney damage and impaired kidney function. In addition, fractures of the vertebrae can cause elevated pressure on the nerve routes, causing neurologic symptoms, numbness tingling, pain, muscle weakness. MM is twice as prevalent in blacks as whites, and has a slight male predominance, with the median onset age is 66 years (Landgren O et al., Leukemia; Kyle R A et al., Mayo Clin Proc. 2003). An early abnormality leading to MM, termed monoclonal gammopathy of undetermined significance (MGUS), is an asymptomatic condition present in 3%-4% of the general population, which raises the risk of developing MM later in life by 1% per year (Kyle R. A et al., N Engl J Med. 2002 346.8 (2002): 564-569; Landgren O., et al., Blood. 2009 May 28; 113 (22): 5412-7). An intermediate stage condition leading up to the development of MM, smoldering multiple myeloma (SMM), is associated with 10% higher risk of progression to MM (Kyle R. A et al., N Engl J Med. 356.25 (2007): 2582-2590).

First line therapies of MM include combination regiments, often a combination therapy consisting of thalidomide, bortezomib and lenalidomide, and in some cases carfilzomib, pomalidomide and panobinostat. However, each of these se medications carries a risk of toxicity. For example, in one MM study the combination of lenalidomide and dexamethasone was associated with garage 3+ toxicity in almost all patients enrolled in the study, as well as early mortality, and venous embolism (Blood 105:4050-4053, 2005). Furthermore, frail or elderly patients, may not be able to tolerate the triple regiment, bringing down the chances of successful therapy. For such patients, alternative treatment approaches are needed. In eligible patients, high dose chemotherapy in combination with autologous stem cell transplant is practiced (Attal M. et al., N Engl J Med. 1996; Child J. A. et al., N Engl J Med. 2003). In some cases, a tandem ASCT is administered, aiming to improve chances of survival (Krishnan A et al., Lancet Oncol. 2011; Fermand J et al., Hematol J. 2003; 4 (Suppl 1): S59). This approach, however, is associated with additional costs, medical risks and discomfort for the patients. If patients are not eligible for ASCT, however, their chances of recovery are low under currently available treatment options.

Treatment consolidation, and management of relapsed or refractory MM involves drug combinations, such as lenalidomide, pomalidomide, cyclophosphamide, prednisolone, which carry risk of treatment-related toxicities and are not curative.

Two monoclonal antibodies, daratumumab and SAR650984, targeting the CD38 molecule, have been used in relapsed and refractory MM (Sagar Lonial et J Clin Oncol. 2015;33 (suppl; abstr LBA8512); Plesner T, Jeckert J et al., CCR 2014, DOI: 10.1158/1078-0432.CCR-14-0695; Front Immunol. 2018; 9:1228. doi: 10.3389). A monoclonal antibody elotuzumab, targeting SLAMF7 (signaling lymphocytic activation molecule F7), has shown activity in relapsed MM when given is part of combination therapy (Lonial S, et al., N Engl J Med. 2015). However, better treatment options are necessary to improve success rate for relapsed or refractory disease, for the treatment of elderly of frail patients, and as an alternative to the currently accepted first-line therapies, in order to reduce side effects and improve efficacy.

B-cell maturation antigen (BCMA, CD269, TNFRSF17) is a marker of MM cells, and is expressed on early 100% MM tumor cells, while normal tissue expression is restricted to plasma cells and a subset of mature B-cells (Avery D T et al., J Clin Invest. 2003, 112 (2)). In addition to MM, BCMA is expressed on a subset of lymphoma clinical samples, and in many lymphoma cell lines, including Raji Non-Hodgkin's lymphoma line (Thompson J S et al., Exp Med. 2000 Jul. 3; 192 (1): 129-35.; Rennert P et al., J Exp Med. 2000 Dec. 4; 192 (11): 1677-84).

CAR approaches targeting BCMA are superior to small molecule combination therapy because they may achieve better efficacy in eliminating BCMA-positive tumor cells and tumor stem cells, and because they avoid the toxicities associated with combination therapy. In addition, CAR T treatment may obviate the need for hematopoetic stem cell transplant, or a tandem transplant an and improve treatment's long-term tolerability, efficacy and survival.

Fully-human BCMA CARs represent an improvement over prior art because unique human ScFv sequences are used in the CAR design, as opposed to murine-derived ScFvs employed in CAR design elsewhere. Mouse-derived sequences carry the risk of immunogenicity, and may induce allergic or anaphylactic responses in patients, leading to CAR T elimination, or life-threatening anaphylaxis.

Chimeric Antigen Receptors (CARs) are hybrid molecules comprising three essential units: (1) an extracellular antigen-binding motif, (2) linking/transmembrane motifs, and (3) intracellular T-cell signaling motifs (Long A H, Haso W M, Orentas R J. Lessons learned from a highly-active CD22-specific chimeric antigen receptor. Oncoimmunology. 2013; 2 (4):e23621). The antigen-binding motif of a CAR is commonly fashioned after an single chain Fragment variable (ScFv), the minimal binding domain of an immunoglobulin (Ig) molecule. Alternate antigen-binding motifs, such as receptor ligands (i.e., IL-13 has been engineered to bind tumor expressed IL-13 receptor), intact immune receptors, library-derived peptides, and innate immune system effector molecules (such as NKG2D) also have been engineered. Alternate cell targets for CAR expression (such as NK or gamma-delta T cells) are also under development (Brown C E et al. Clin Cancer Res. 2012; 18 (8): 2199-209; Lehner M et al. PLOS One. 2012; 7 (2):e31210). There remains significant work with regard to defining the most active T-cell population to transduce with CAR vectors, determining the optimal culture and expansion techniques, and defining the molecular details of the CAR protein structure itself.

The linking motifs of a CAR can be a relatively stable structural domain, such as the constant domain of IgG, or designed to be an extended flexible linker. Structural motifs, such as those derived from IgG constant domains, can be used to extend the ScFv binding domain away from the T-cell plasma membrane surface. This may be important for some tumor targets where the binding domain is particularly close to the tumor cell surface membrane (such as for the disialoganglioside GD2; Orentas et al., unpublished observations). To date, the signaling motifs used in CARs always include the CD3-chain because this core motif is the key signal for T cell activation. The first reported second-generation CARs featured CD28 signaling domains and the CD28 transmembrane sequence. This motif was used in third-generation CARs containing CD137 (4-1BB) signaling motifs as well (Zhao Y et al. J Immunol. 2009; 183 (9): 5563-74). With the advent of new technology, the activation of T cells with beads linked to anti-CD3 and anti-CD28 antibody, and the presence of the canonical "signal 2" from CD28 was no longer required to be encoded by the CAR itself. Using bead activation, third-generation vectors were found to be not superior to second-generation vectors in in vitro assays, and they provided no clear benefit over second-generation vectors in mouse models of leukemia (Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. Anti-CD22-chimeric antigen receptors targeting B cell precursor acute lymphoblastic leukemia, Blood. 2013; 121 (7): 1165-74; Kochenderfer J N et al. Blood. 2012; 119 (12): 2709-20). This is borne out by the clinical success of CD19-specific CARs that are in a second generation CD28/CD3-ζ (Lee D W et al. American Society of Hematology Annual Meeting. New Orleans, LA; Dec. 7-10, 2013) and a CD137/CD3-ζ signaling format (Porter D L et al. N Engl J Med. 2011; 365 (8): 725-33). In addition to CD137, other tumor necrosis factor receptor superfamily members such as OX40 also are able to provide important persistence signals in CAR-transduced T cells (Yvon E et al. Clin Cancer Res. 2009; 15 (18): 5852-60). Equally important are the culture conditions under which the CAR T-cell populations were cultured.

Current challenges in the more widespread and effective adaptation of CAR therapy for cancer relate to a paucity of compelling targets. Creating binders to cell surface antigens is now readily achievable, but discovering a cell surface antigen that is specific for tumor while sparing normal tissues remains a formidable challenge. One potential way to imbue greater target cell specificity to CAR-expressing T cells is to use combinatorial CAR approaches. In one system, the CD3-2 and CD28 signal units are split between two different CAR constructs expressed in the same cell; in another, two CARs are expressed in the same T cell, but one has a lower affinity and thus requires the alternate CAR to be engaged first for full activity of the second (Lanitis E et al. Cancer Immunol Res. 2013; 1 (1): 43-53; Kloss C C et al. Nat Biotechnol. 2013; 31 (1): 71-5). A second challenge for the generation of a single ScFv-based CAR as an immunotherapeutic agent is tumor cell heterogeneity. At least one group has developed a CAR strategy for glioblastoma whereby the effector cell population targets multiple antigens (HER2, IL-13Ra, EphA2) at the same time in the hope of avoiding the outgrowth of target antigen-negative populations. (Hegde M et al. Mol Ther. 2013; 21 (11): 2087-101).

T-cell-based immunotherapy has become a new frontier in synthetic biology; multiple promoters and gene products are envisioned to steer these highly potent cells to the tumor microenvironment, where T cells can both evade negative regulatory signals and mediate effective tumor killing. The elimination of unwanted T cells through the drug-induced dimerization of inducible caspase 9 constructs with AP1903 demonstrates one way in which a powerful switch that can control T-cell populations can be initiated pharmacologically (Di Stasi A et al. N Engl J Med. 2011; 365 (18): 1673-83). The creation of effector T-cell populations that are immune to the negative regulatory effects of transforming growth factor-β by the expression of a decoy receptor further demonstrates that degree to which effector T cells can be engineered for optimal anti-tumor activity (Foster A E et al. J Immunother. 2008;31 (5): 500-5). Thus, while it appears that CARs can trigger T-cell activation in a manner similar to an endogenous T-cell receptor, a major impediment to the clinical application of this technology to date has been limited in vivo expansion of CAR+ T cells, rapid disappearance of the cells after infusion, and disappointing clinical activity. Accordingly, there is an urgent and long felt need in the art for discovering novel compositions and methods for treatment of MM using an approach that can exhibit specific and efficacious anti-tumor effect without the aforementioned short comings.

The present invention addresses these needs by providing CAR compositions and therapeutic methods that can be used to treat BCMA-positive cancers and other diseases and/or conditions. In particular, the present invention as disclosed and described herein provides CARs that may be used the treatment of BCMA-positive cancers, and which CARs contain BCMA antigen binding domains that exhibit a high surface expression on transduced T cells, exhibit a high degree of cytolysis and transduced T cell in vivo expansion and persistence.

SUMMARY

Novel anti-BCMA antibodies or antigen binding domains thereof and chimeric antigen receptors (CARs) that contain such BCMA antigen binding domains are provided herein, as well as host cells (e.g., T cells) expressing the receptors, and nucleic acid molecules encoding the receptors. CAR may consist either of a single molecule expressed on the effector cell surface, or a CAR comprised of an effector cell-expressed signaling module and a soluble targeting module, such as when the soluble targeting module binds to the cell-expressed signaling module, a complete functional CAR is formed. The CARs exhibit a high surface expression on transduced T cells, with a high degree of cytolysis and transduced T cell expansion and persistence in vivo. Methods of using the disclosed CARs, host cells, and nucleic acid molecules are also provided, for example, to treat a cancer in a subject.

Thus, in one aspect, an isolated polynucleotide encoding a human anti-BCMA antibody or a fragment thereof is provided comprising a nucleic acid sequence selected from the group consisting of SEQ ID NOs: 1, 3, 5, 7, 9, 11, 15, 17, 19, 21, 23, 25, 69, 71, 73, 75, and 77.

In one embodiment, an isolated polynucleotide encoding a fully human anti-BCMA antibody or a fragment thereof is provided, wherein the antibody or a fragment thereof comprises a fragment selected from the group consisting of an Fab fragment, an F(ab') 2 fragment, an Fv fragment, and a single chain Fv (ScFv).

In one embodiment, an isolated polynucleotide encoding a fully human anti-BCMA antibody or a fragment thereof is provided, wherein the antibody or a fragment thereof comprises an amino acid sequence selected from the group consisting of SEQ ID NOs: 2, 4, 6, 8, 10, 12, 16, 18, 20, 22, 24, 26, 70, 72, 74, 76, and 78.

In one aspect, an isolated nucleic acid molecule encoding a chimeric antigen receptor (CAR) is provided comprising, from N-terminus to C-terminus, at least one BCMA antigen binding domain encoded by a nucleotide sequence comprising a nucleic acid sequence selected from the group consisting of SEQ ID NOs: 1, 3, 5, 7, 9, 11, 15, 17, 19, 21, 23, 25, 69, 71, 73, 75, and 77, at least one transmembrane domain, and at least one intracellular signaling domain.

In one embodiment, an isolated nucleic acid molecule encoding the CAR is provided wherein the encoded extracellular BCMA antigen binding domain comprises at least one single chain variable fragment of an antibody that binds to BCMA.

In another embodiment, an isolated nucleic acid molecule encoding the CAR is provided wherein the encoded extracellular BCMA antigen binding domain comprises at least one heavy chain variable region of an antibody that binds to BCMA.

In another embodiment, an isolated nucleic acid molecule encoding the CAR is provided wherein the encoded extracellular BCMA antigen binding domain comprises an ScFv.

In one embodiment, the targeting domain of the CAR is expressed separately in the form of monoclonal antibody, ScFv Fab, Fab'2 and is containing an antigen-targeting domain comprising a nucleic acid sequence selected from the group consisting of SEQ ID NOs: 1, 3, 5, 7, 9, 11, 15, 17, 19, 21, 23, 25, 69, 71, 73, 75, and 77, coupled to an additional binding tag or epitope, whereas the effector-cell expressed component of the CAR contains a binding domain specifically directed to bind the tag or epitope expressed on the soluble CAR module, such as specific binding on the soluble component of the CAR to the cell bound component of the CAR forms the full functional CAR structure.

In another embodiment, the targeting domain of the CAR is expressed separately in the form of a monoclonal antibody, ScFv Fab, Fab'2 and contains an antigen-targeting domain comprising a nucleic acid sequence selected from the group consisting of SEQ ID NOs: 1, 3, 5, 7, 9, 11, 15, 17, 19, 21, 23, 25, 69, 71, 73, 75, and 77, and an additional ScFv, whereas the effector-cell expressed component of the CAR contains a tag or epitope specifically reactive with the additional ScFv expressed on the soluble CAR module, such as specific binding on the soluble component of the CAR to the cell bound component of the CAR forms the full functional CAR structure.

In yet another embodiment, an isolated nucleic acid molecule encoding the CAR is provided wherein the encoded CAR extracellular BCMA antigen binding domain further comprises at least one lipocalin-based antigen binding antigen (anticalins) that binds to BCMA.

In one embodiment, an isolated nucleic acid molecule is provided wherein the encoded extracellular BCMA antigen binding domain is connected to the transmembrane domain by a linker domain.

In another embodiment, an isolated nucleic acid molecule encoding the CAR is provided wherein the encoded BCMA extracellular antigen binding domain is preceded by a sequence encoding a leader or signal peptide.

In yet another embodiment, an isolated nucleic acid molecule encoding the CAR is provided comprising at least one BCMA antigen binding domain encoded by a nucleotide sequence comprising a nucleic acid sequence selected from the group consisting of SEQ ID NOs: 1, 3, 5, 7, 9, 11, 15, 17, 19, 21, 23, 25, 69, 71, 73, 75, and 77, and wherein the CAR additionally encodes an extracellular antigen binding domain targets an antigen that includes, but is not limited to, CD19, CD20, CD22, ROR1, mesothelin, CD33, CD38, CD123 (IL3RA), CD138, GPC2, GPC3, FGFR4, c-Met, PSMA, Glycolipid F77, EGFRVIII, GD-2, NY-ESO-1 TCR, MAGE A3 TCR, or any combination thereof.

In certain embodiments, an isolated nucleic acid molecule encoding the CAR is provided wherein the additionally encoded extracellular antigen binding domain comprises an anti-CD19 ScFv antigen binding domain, an anti-CD20 ScFv antigen binding domain, an anti-CD22 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-GPC2 ScFv antigen binding domain, an anti-GPC3 ScFv antigen binding domain, an anti-FGFR4 ScFv antigen binding domain, an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESO-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In one aspect, the CARs provided herein further comprise a linker or spacer domain.

In one embodiment, an isolated nucleic acid molecule encoding the CAR is provided wherein the extracellular BCMA antigen binding domain, the intracellular signaling domain, or both are connected to the transmembrane domain by a linker or spacer domain.

In one embodiment, an isolated nucleic acid molecule encoding the CAR is provided wherein the encoded linker domain is derived from the extracellular domain of CD8 or CD28, and is linked to a transmembrane domain.

In another embodiment, an isolated nucleic acid molecule encoding the CAR is provided wherein the encoded CAR further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In yet another embodiment, an isolated nucleic acid molecule encoding the CAR is provided wherein the encoded intracellular signaling domain further comprises a CD3 zeta intracellular domain.

In one embodiment, an isolated nucleic acid molecule encoding the CAR is provided wherein the encoded intracellular signaling domain is arranged on a C-terminal side relative to the CD3 zeta intracellular domain.

In another embodiment, an isolated nucleic acid molecule encoding the CAR is provided wherein the encoded at least one intracellular signaling domain comprises a costimulatory domain, a primary signaling domain, or a combination thereof.

In further embodiments, an isolated nucleic acid molecule encoding the CAR is provided wherein the encoded at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, an isolated nucleic acid molecule encoding the CAR is provided that further contains a leader sequence or signal peptide wherein the leader or signal peptide nucleotide sequence comprises the nucleotide sequence of SEQ ID NO: 13, SEQ ID NO: 39, SEQ ID NO: 41, or SEQ ID NO: 43.

In yet another embodiment, an isolated nucleic acid molecule encoding the CAR is provided wherein the encoded leader sequence comprises the amino acid sequence of SEQ ID NO: 14, SEQ ID NO: 40, SEQ ID NO: 42, or SEQ ID NO: 44.

In one aspect, a chimeric antigen receptor (CAR) is provided herein comprising, from N-terminus to C-terminus, at least one BCMA antigen binding domain, at least one transmembrane domain, and at least one intracellular signaling domain.

In one embodiment, a CAR is provided wherein the extracellular BCMA antigen binding domain comprises at least one single chain variable fragment of an antibody that binds to the antigen, or at least one heavy chain variable region of an antibody that binds to the antigen, or a combination thereof.

In another embodiment, a CAR is provided wherein the at least one transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In some embodiments, the CAR is provided wherein CAR additionally encodes an extracellular antigen binding domain comprising CD19, CD20, CD22, ROR1, mesothelin, CD33, CD38, CD123 (IL3RA), CD138, GPC2, GPC3, FGFR4, c-Met, PSMA, Glycolipid F77, EGFRVIII, GD-2, NY-ESO-1 TCR, MAGE A3 TCR, or an amino acid sequence with 85%, 90%, 95%, 96%, 97%, 98% or 99% identity thereof, or any combination thereof.

In one embodiment, the CAR is provided wherein the extracellular antigen binding domain additionally comprises an anti-CD19 ScFv antigen binding domain, an anti-CD20 ScFv antigen binding domain, an anti-CD22 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-GPC2 ScFv antigen binding domain, an anti-GPC3 ScFv antigen binding domain, an anti-FGFR4 ScFv antigen binding domain, an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESo-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In another embodiment, the CAR is provided wherein the extracellular antigen binding domain additionally comprises an immunoglobulin variable heavy chain only (VH) anti-CD19 antigen binding domain, an anti-CD20 VH antigen binding domain, an anti-CD22 VH antigen binding domain, an anti-ROR1 VH antigen binding domain, an anti-mesothelin VH antigen binding domain, an anti-CD33 VH antigen binding domain, an anti-CD38 VH antigen binding domain, an anti-CD123 (IL3RA) VH antigen binding domain, an anti-CD138 VH antigen binding domain, an anti-GPC2 VH antigen binding domain, an anti-GPC3 VH antigen binding domain, an anti-FGFR4 VH antigen binding domain, an anti-c-Met VH antigen binding domain, an anti-PMSA VH antigen binding domain, an anti-glycolipid F77 VH antigen binding domain, an anti-EGFRvIII VH antigen binding domain, an anti-GD-2 VH antigen binding domain, an anti-NY-ESO-1 TCR VH antigen binding domain, an anti-MAGE A3 TCR VH antigen binding domain, or an amino acid sequence with 85%, 90%, 95%, 96%, 97%, 98% or 99% identity thereof, or any combination thereof.

In another embodiment, the CAR is provided wherein the extracellular antigen binding domain additionally comprises a protein or a peptide (P) sequence capable of specifically binding target antigen, which may be derived from a natural or a synthetic sequence comprising anti-CD19 P antigen binding domain, an anti-CD20 P antigen binding domain, an anti-CD22 P antigen binding domain, an anti-ROR1 P antigen binding domain, an anti-mesothelin P antigen binding domain, an anti-CD33 P antigen binding domain, an anti-CD38 P antigen binding domain, an anti-CD123 (IL3RA) P antigen binding domain, an anti-CD138 P antigen binding domain, an anti-BCMA (CD269) P antigen binding domain, an anti-GPC2 P antigen binding domain, an anti-GPC3 P antigen binding domain, an anti-FGFR4 P antigen binding domain, an anti-c-Met P antigen binding domain, an anti-PMSA P antigen binding domain, an anti-glycolipid F77 P antigen binding domain, an anti-EGFRvIII P antigen binding domain, an anti-GD-2 P antigen binding domain, an anti-NY-ESO-1 TCR P antigen binding domain, an anti-MAGE A3 TCR P antigen binding domain, or an amino acid sequence with 85%, 90%, 95%, 96%, 97%, 98% or 99% identity thereof, or any combination thereof. In another embodiment, a CAR is provided wherein the at least one intracellular signaling domain comprises a costimulatory domain and a primary signaling domain.

In yet another embodiment, a CAR is provided wherein the at least one intracellular signaling domain comprises a costimulatory domain comprising a functional signaling domain of a protein selected from the group consisting of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, the nucleic acid sequence encoding a CAR comprises the nucleic acid sequence of SEQ ID NO: 87. In one embodiment, the nucleic acid sequence encodes a CAR comprising the amino acid sequence of SEQ ID NO: 88.

In another embodiment, the nucleic acid sequence encoding a CAR comprises the nucleic acid sequence of SEQ ID NO: 89. In one embodiment, the nucleic acid sequence encodes a CAR comprising the amino acid sequence of SEQ ID NO: 90.

In another embodiment, the nucleic acid sequence encoding a CAR comprises the nucleic acid sequence of SEQ ID NO: 91. In one embodiment, the nucleic acid sequence encodes a CAR comprising the amino acid sequence of SEQ ID NO: 92.

In another embodiment, the nucleic acid sequence encoding a CAR comprises the nucleic acid sequence of SEQ ID NO: 93. In one embodiment, the nucleic acid sequence encodes a CAR comprising the amino acid sequence of SEQ ID NO: 94.

In another embodiment, the nucleic acid sequence encoding a CAR comprises the nucleic acid sequence of SEQ ID NO: 95. In one embodiment, the nucleic acid sequence encodes a CAR comprising the amino acid sequence of SEQ ID NO: 96.

In another embodiment, the nucleic acid sequence encoding a CAR comprises the nucleic acid sequence of SEQ ID NO: 97. In one embodiment, the nucleic acid sequence encodes a CAR comprising the amino acid sequence of SEQ ID NO: 98.

In another embodiment, the nucleic acid sequence encoding a CAR comprises the nucleic acid sequence of SEQ ID NO: 99. In one embodiment, the nucleic acid sequence encodes a CAR comprising the amino acid sequence of SEQ ID NO: 100.

In another embodiment, the nucleic acid sequence encoding a CAR comprises the nucleic acid sequence of SEQ ID NO: 101. In one embodiment, the nucleic acid sequence encodes a CAR comprising the amino acid sequence of SEQ ID NO: 102.

In one aspect, the CARs disclosed herein are modified to express or contain a detectable marker for use in diagnosis, monitoring, and/or predicting the treatment outcome such as progression free survival of cancer patients or for monitoring the progress of such treatment.

In one embodiment, the nucleic acid molecule encoding the disclosed CARs can be contained in a vector, such as a viral vector. The vector is a DNA vector, an RNA vector, a plasmid vector, a cosmid vector, a herpes virus vector, a measles virus vector, a lentivirus vector, adenoviral vector, or a retrovirus vector, or a combination thereof.

In certain embodiments, the vector further comprises a promoter wherein the promoter is an inducible promoter, a tissue specific promoter, a constitutive promoter, a suicide promoter or any combination thereof.

In yet another embodiment, the vector expressing the CAR can be further modified to include one or more operative elements to control the expression of CAR T cells, or to eliminate CAR-T cells by virtue of a suicide switch. The suicide switch can include, for example, an apoptosis inducing signaling cascade or a drug that induces cell death. In a preferred embodiment, the vector expressing the CAR can be further modified to express an enzyme such thymidine kinase (TK) or cytosine deaminase (CD).

In another aspect, host cells including the nucleic acid molecule encoding the CAR are also provided. In some embodiments, the host cell is a T cell, such as a primary T cell obtained from a subject. In one embodiment, the host cell is a CD8+ T cell.

In yet another aspect, a pharmaceutical composition is provided comprising an anti-tumor effective amount of a population of human T cells, wherein the T cells comprise a nucleic acid sequence that encodes a chimeric antigen receptor (CAR), wherein the CAR comprises at least one extracellular antigen binding domain comprising a BCMA antigen binding domain comprising the amino acid sequence selected from the group consisting of SEQ ID NOs: 2, 4, 6, 8, 10, 12, 16, 18, 20, 22, 24, 26, 70, 72, 74, 76, and 78; at least one linker domain; at least one transmembrane domain; and at least one intracellular signaling domain, wherein the T cells are T cells of a human having a cancer. The cancer includes, inter alia, a hematological cancer such as leukemia (e.g., chronic lymphocytic leukemia (CLL), acute lymphocytic leukemia (ALL), or chronic myelogenous leukemia (CML), lymphoma (e.g., mantle cell lymphoma, non-Hodgkin's lymphoma or Hodgkin's lymphoma) or multiple myeloma, or a combination thereof.

In one embodiment, a pharmaceutical composition is provided wherein the at least one transmembrane domain of the CAR contains a transmembrane domain of a protein selected from the group consisting of the alpha, beta or zeta chain of the T-cell receptor, CD28, CD3 epsilon, CD45, CD4, CD5, CD8, CD9, CD16, CD22, Mesothelin, CD33, CD37, CD64, CD80, CD86, CD134, CD137 and CD154, or a combination thereof.

In another embodiment, a pharmaceutical composition is provided wherein the human cancer includes an adult carcinoma comprising oral and pharynx cancer (tongue, mouth, pharynx, head and neck), digestive system cancers (esophagus, stomach, small intestine, colon, rectum, anus, liver, interhepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, the genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

In yet another embodiment, a pharmaceutical composition is provided comprising an anti-tumor effective amount of a population of human T cells of a human having a cancer wherein the cancer is a refractory cancer non-responsive to one or more chemotherapeutic agents. The cancer includes hematopoietic cancer, myelodysplastic syndrome pancreatic cancer, head and neck cancer, cutaneous tumors, minimal residual disease (MRD) in multiple myeloma (MM), smoldering multiple myeloma (SMM), monoclonal gammopathy of undetermined significance (MGUS), adult and pediatric hematologic malignancies, including acute lymphoblastic leukemia (ALL), CLL (Chronic lymphocytic leukemia), non-Hodgkin's lymphoma (NHL), including follicular lymphoma (FL), diffuse large B cell lymphoma (DLBCL), mantle cell lymphoma (MCL), Hodgkin's lymphoma (HL). chronic myelogenous leukemia (CML), lung cancer, breast cancer, ovarian cancer, prostate cancer, colon cancer, melanoma or other hematological cancer and solid tumors, or any combination thereof.

In another aspect, methods of making CAR-containing T cells (hereinafter “CAR-T cells”) are provided. The methods include transducing a T cell with a vector or nucleic acid molecule encoding a disclosed CAR that specifically binds BCMA, thereby making the CAR-T cell.

In yet another aspect, a method of generating a population of RNA-engineered cells is provided that comprises introducing an in vitro transcribed RNA or synthetic RNA of a nucleic acid molecule encoding a disclosed CAR into a cell of a subject, thereby generating a CAR cell.

In yet another aspect, a method for diagnosing a disease, disorder or condition associated with the expression of BCMA on a cell, is provided comprising a) contacting the cell with a human anti-BCMA antibody or fragment thereof, wherein the antibody or a fragment thereof comprises an amino acid sequence selected from the group consisting of SEQ ID NOs: 2, 4, 6, 8, 10, 12, 16, 18, 20, 22, 24, 26, 70, 72, 74, 76, and 78; and b) detecting the presence of BCMA wherein the presence of BCMA diagnoses for the disease, disorder or condition associated with the expression of BCMA.

In one embodiment, the disease, disorder or condition associated with the expression of BCMA is cancer including hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (chronic lymphocytic leukemia), CML (chronic myelogenous leukemia), non-Hodgkin’s lymphoma (NHL), pediatric B cell malignancies (including B lineage ALL (acute lymphocytic leukemia)), multiple myeloma lung cancer, breast cancer, ovarian cancer, prostate cancer, colon cancer, melanoma or other hematological cancer and solid tumors, or any combination thereof.

In another embodiment, a method of diagnosing, prognosing, or determining risk of a BCMA-related disease in a mammal, is provided comprising detecting the expression of BCMA in a sample derived from the mammal comprising: a) contacting the sample with a human anti-BCMA antibody or fragment thereof, wherein the antibody or a fragment thereof comprises an amino acid sequence selected from the group consisting of SEQ ID NOs: 2, 4, 6, 8, 10, 12, 16, 18, 20, 22, 24, 26, 70, 72, 74, 76, and 78; and b) detecting the presence of BCMA wherein the presence of BCMA diagnoses for a BCMA-related disease in the mammal.

In another embodiment, a method of inhibiting BCMA-dependent T cell inhibition, is provided comprising contacting a cell with a human anti-BCMA antibody or fragment thereof, wherein the antibody or a fragment thereof comprises an amino acid sequence selected from the group consisting of SEQ ID NOs: 2, 4, 6, 8, 10, 12, 16, 18, 20, 22, 24, 26, 70, 72, 74, 76, and 78. In one embodiment, the cell is selected from the group consisting of a BCMA-expressing tumor cell, a tumor-associated macrophage, and any combination thereof.

In another embodiment, a method of blocking T-cell inhibition mediated by a BCMA-expressing cell and altering the tumor microenvironment to inhibit tumor growth in a mammal, is provided comprising administering to the mammal an effective amount of a composition comprising an isolated anti-BCMA antibody or fragment thereof, wherein the antibody or a fragment thereof comprises an amino acid sequence selected from the group consisting of SEQ ID NOs: 2, 4, 6, 8, 10, 12, 16, 18, 20, 22, 24, 26, 70, 72, 74, 76, and 78. In one embodiment, the cell is selected from the group consisting of a BCMA-expressing tumor cell, a tumor-associated macrophage, and any combination thereof.

In another embodiment, a method of inhibiting, suppressing or preventing immunosuppression of an anti-tumor or anti-cancer immune response in a mammal, is provided comprising administering to the mammal an effective amount of a composition comprising an isolated anti-BCMA antibody or fragment thereof, wherein the antibody or a fragment thereof comprises an amino acid sequence selected from the group consisting of SEQ ID NOs: 2, 4, 6, 8, 10, 12, 16, 18, 20, 22, 24, 26, 70, 72, 74, 76, and 78. In one embodiment, the antibody or fragment thereof inhibits the interaction between a first cell with a T cell, wherein the first cell is selected from the group consisting of a BCMA-expressing tumor cell, a tumor-associated macrophage, and any combination thereof.

In another aspect, a method is provided for inducing an anti-tumor immunity in a mammal comprising administering to the mammal a therapeutically effective amount of a T cell transduced with vector or nucleic acid molecule encoding a disclosed CAR.

In another embodiment, a method of treating or preventing cancer in a mammal is provided comprising administering to the mammal one or more of the disclosed CARs, in an amount effective to treat or prevent cancer in the mammal. The method includes administering to the subject a therapeutically effective amount of host cells expressing a disclosed CAR that specifically binds BCMA and/or one or more of the aforementioned antigens, under conditions sufficient to form an immune complex of the antigen binding domain on the CAR and the extracellular domain of BCMA and/or one or more of the aforementioned antigens in the subject.

In yet another embodiment, a method is provided for treating a mammal having a disease, disorder or condition associated with an elevated expression of a tumor antigen, the method comprising administering to the subject a pharmaceutical composition comprising an anti-tumor effective amount of a population of T cells, wherein the T cells comprise a nucleic acid sequence that encodes a chimeric antigen receptor (CAR), wherein the CAR includes at least one extracellular BCMA antigen binding domain comprising the amino acid sequence of SEQ ID NOs: 2, 4, 6, 8, 10, 12, 16, 18, 20, 22, 24, 26, 70, 72, 74, 76, and 78, or any combination thereof, at least one linker or spacer domain, at least one transmembrane domain, at least one intracellular signaling domain, and wherein the T cells are T cells of the subject having cancer.

In yet another embodiment, a method is provided for treating cancer in a subject in need thereof comprising administering to the subject a pharmaceutical composition comprising an anti-tumor effective amount of a population of T cells, wherein the T cells comprise a nucleic acid sequence that encodes a chimeric antigen receptor (CAR), wherein the CAR comprises at least one BCMA antigen binding domain comprising the amino acid sequence of SEQ ID NOs: 2, 4, 6, 8, 10, 12, 16, 18, 20, 22, 24, 26, 70, 72, 74, 76, and 78, or any combination thereof, at least one linker or spacer domain, at least one transmembrane domain, at least one intracellular signaling domain, wherein the T cells are T cells of the subject having cancer. In some embodiments of the aforementioned methods, the at least one transmembrane domain comprises a transmembrane the alpha, beta or zeta chain of the T-cell receptor, CD28, CD3 epsilon, CD45, CD4, CD5, CD8, CD9, CD16, CD22, Mesothelin, CD33, CD37, CD64, CD80, CD86, CD134, CD137 and CD154, or a combination thereof.

In yet another embodiment, a method is provided for generating a persisting population of genetically engineered T cells in a human diagnosed with cancer. In one embodiment, the method comprises administering to a human a T cell genetically engineered to express a CAR wherein the CAR comprises at least one BCMA antigen binding domain comprising the amino acid sequence of SEQ ID NOs: 2, 4, 6, 8, 10, 12, 16, 18, 20, 22, 24, 26, 70, 72, 74, 76, and 78, or any combination thereof; at least one transmembrane domain; and at least one intracellular signaling domain wherein the persisting population of genetically engineered T cells, or the population of progeny of the T cells, persists in the human for at least one month, two months, three months, four months, five months, six months, seven months, eight months, nine months, ten months, eleven months, twelve months, two years, or three years after administration.

In one embodiment, the progeny T cells in the human comprise a memory T cell. In another embodiment, the T cell is an autologous T cell.

In all of the aspects and embodiments of methods described herein, any of the aforementioned cancers, diseases, disorders or conditions associated with an elevated expression of a tumor antigen that may be treated or prevented or ameliorated using one or more of the CARs disclosed herein, In yet another aspect, a kit is provided for making a chimeric antigen receptor T-cell as described supra or for preventing, treating, or ameliorating any of the cancers, diseases, disorders or conditions associated with an elevated expression of a tumor antigen in a subject as described supra, comprising a container comprising any one of the nucleic acid molecules, vectors, host cells, or compositions disclosed supra or any combination thereof, and instructions for using the kit.

It will be understood that the CARs, host cells, nucleic acids, and methods are useful beyond the specific aspects and embodiments that are described in detail herein. The foregoing features and advantages of the disclosure will become more apparent from the following detailed description, which proceeds with reference to the accompanying figures.

BRIEF DESCRIPTION OF THE FIGURES

FIGS. 3A-C depict CAR T cytotoxicity in vitro. CARs are designated by their ScFv number, preceded by a prefix "BCMA". Luciferase-based cytotoxicity assays were performed using, BCMA-positive tumor lines RPMI-8226 (FIG. 3A), and MM1.S (FIG. 3B), or BCMA-negative cell line 293T (FIG. 3C), stably transduced with firefly luciferase. Bars represent mean+SD values from three technical replicates.

FIGS. 4A-B depict surface expression of BCMA-targeting CAR T constructs on human primary T cells. T cells were isolated form a buffy coat via CD4+CD8+ positive selection using Miltenyi cell isolation reagents. CAR T expression was determined by flow cytometry. T cells were activated with Miltenyi Biotec TransAct™ CD3 CD28 reagent in the presence of IL-2, and transduced with LV as described in Materials and Methods. On culture day 8, viable transduced T cells (7-AAD negative) were assayed for CAR surface expression using the BCMA-Fc method. CAR construct number is listed to the left of each figure. Expression of CAR T in CD8−(CD4+) and CD8+ cell population is shown in the left column (FIG. 4A), and the total CAR expression is shown in the histogram on the right (FIG. 4B). Bars on the right represent the percentage of CAR T-positive populations in relation to non-transduced T cell control (UTD, not shown).

FIGS. 5A-B depict the cytotoxicity of anti-BCMA CARs D0084, D0085, D0086, D0087, D0099, D0100 in vitro, in two separate donors. Luciferase-based cytotoxicity assays were performed using BCMA-positive tumor lines RPMI-8226, and MM1.S, or BCMA-negative cell line 293T, stably transduced with firefly luciferase. Bars represent mean+SD values from three technical replicates.

FIGS. 6A-G depict the superior functionality of the D100 BCMA CAR in comparison to the D085 BCMA CAR in a long-term in vitro co-incubation assay. (FIG. 6A) The structure of the BCMA CARs D100 and D085 includes an scFv CAR targeting domain linked to the CD8 extracellular and transmembrane domains, followed by the 4-1BB co-stimulatory molecule and the CD32 domain. (FIG. 6B) T-cells were transduced at various MOIs with lentiviral vectors harboring either the D100 or the D085 BCMA CAR constructs, and the cell surface expression of the CARs was assessed by flow cytometry. (FIG. 6C) In the long-term co-culture experiment, CAR T-cells were co-incubated with the target multiple myeloma cell line, MM1.S tagged with GFP, at an ETT ratio of 0.1. The co-culture was repeated for four rounds in the span of 20 days. The absolute counts of (FIG. 6D) T-cells and (FIG. 6E) target cells were assessed by flow cytometry at different time points during the four rounds of co-culture by quantifying the number of CD3+ cells and GFP+ cells, respectively. The absolute counts were determined by using CountBright Absolute Counting Beads. (FIG. 6F) The changes in the percentages of CAR+CD4+ and CD8+ at various timepoints during the long term co-culture were assessed by flow cytometry. (FIG. 6F) The production of IL-2, TNFα, and IFNγ in CD3+ cells was determined by intracellular staining and flow cytometric analysis on day 11 during the third round of co-culture (FIG. 6G).

FIGS. 7A-C depict in vivo evaluation of BCMA-targeting CAR Constructs. (FIG. 7A) Eight millions of RPMI-8226 cells were intradermally injected on the abdomen of NSG mice (all groups n=8, except untreated, n=5) and allowed to engraft for 17 days before the intravenous injection of five million/mouse CAR T-cells. The number of CAR T-cells that was infused was normalized based on CAR expression levels. On day 6, after T-cell infusion, 3 mice from each group were sacrificed for tumor harvest while the rest of the mice were monitored for (FIG. 7B) tumor growth and (FIG. 7C) survival.

FIGS. 8A-D depict in vitro characterization of CAR D153, incorporating the scFv sequence 4-1c. The scFv 4-1c was cloned into a CAR backbone comprised of CD8 extracellular and transmembrane domains, 4-1BB co-stimulatory domain, and CD3ζ activating domain, identical to that used in CARD100 and D085, as shown in FIG. 6A. (FIG. 8A) Lentiviral transduction efficiency of CAR D153, D100 and D085 in primary human T cells was measured by flow cytometry. (FIG. 8B) The cytotoxicity of anti-BCMA CARs D153, D100, D085, or non-transduced UTD control T cells in vitro. Luciferase-based cytotoxicity assays were performed using BCMA-positive tumor lines RPMI-8226, and MM1.S, stably transduced with firefly luciferase. (FIG. 8C). In vivo evaluation of BCMA-targeting CAR D153 as compared to BCMA CAR D100 in RPMI-8226 intradermal NSG xenograft model. (n=5) (FIG. 8D). Tumors were established for 17 days following intradermal injection of eight million RPMI-8226 cells per mouse. Tumor-bearing mice were distributed to groups with equal mean tumor volumes. Five million CAR T cells or UTD control were injected i.v., and tumor volume was recorded three times a week up to study day 40. Untreated-tumor only control.

FIGS. 9A-E depict the resistance to immunosuppressive TGFβ effects exhibited by the armored BCMA CAR incorporating the truncated TGFBRII dominant negative receptor. (FIG. 9A) The sequence of the extracellular binding and transmembrane domains of TGFBRII, but excluding the intracellular kinase domain, was cloned into the D100 BCMA CAR construct. A P2A element was utilized to allow for the separate co-expression of the BCMA CAR and the TGFBRII DN. (FIG. 9B) T-cells were transduced with lentiviral vectors containing either the D100 BCMA CAR construct or the armored BCMA CAR construct combining the D100 CAR with the TGFBRII DN element (D158) at MOI 10 and 80, respectively. The cell surface expression of the BCMA CAR (upper panel) and TGFBRII (lower panel) was assessed by flow cytometry. (FIG. 9C) In the long term co-culture experiment, CAR T-cells were co-incubated with the target cells, MM1.S-GFP, at an ETT ratio of 0.1, and the media was treated with 10 ng/ml of TGF-beta or remained untreated. When the target cells were eliminated on day 6, the co-culture was extended for a second round at an initial ETT ratio of 0.1. The absolute counts of (FIG. 9D) T-cells and (FIG. 9E) target cells at different time points during the long-term co-culture was assessed by quantifying the number of CD3+ and GFP+ cells via flow cytometry using absolute counting beads.

FIGS. 10A-H depict the superior efficacy of the armored BCMA CAR D158 incorporating the truncated TGFBRII dominant negative element in eradicating tumors in vivo. (FIG. 10A) Multiple myeloma cell lines, RPMI-8226 and MM1.S, were cultured for 4 days, and supernatants were collected and treated with 1 M HCL to activate latent TGFβ, or the supernatants remained untreated. The presence of active TGFβ, in the supernatants was detected by ELISA. (FIG. 10B) NSG mice were intradermally injected on the abdomen with 8e6 RPMI-8226 cells (n=8 except untreated, n=5). On day 17 after tumor injection, 5e6 CAR+ T-cells were intravenously injected. The differences in CAR expression levels were normalized by adjusting the total number of infused T-cells. On day 7 after T-cell infusion, 3 mice from each group (except the untreated group) were sacrificed for tumor harvest, while the rest were monitored for (FIG. 10C) tumor progression and (FIG. 10D) survival. (FIG. 10E) The absolute counts of CD3+ cells, (FIG. 10F) the percentage of CD3+CAR+, (FIG. 10G) CD3+PD1+, and (FIG. 10H) CD3+CD45RO+ cells in the tumors on day 6 were determined by flow cytometry.

DETAILED DESCRIPTION

Definitions

Figure 1:
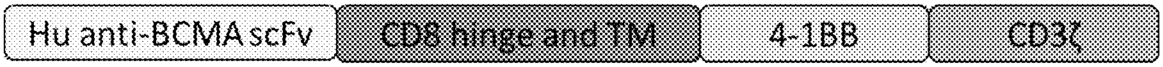
FIG. 1 depicts the construction of CARs targeting BCMA. The anti-BCMA ScFv targeting domain was linked in frame to CD8 hinge and transmembrane domain, the 4-1BB (CD137) signaling domain and the CD3 zeta signaling domain.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements. The phrase "and/or" means "and" or "or." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

The term "about" when referring to a measurable value such as an amount, a temporal duration, and the like, is meant to encompass variations of. +-. 20% or in some instances. +-. 10%, or in some instances. +-. 5%, or in some instances. +-. 1%, or in some instances. +-. 0.1% from the specified value, as such variations are appropriate to perform the disclosed methods.

Unless otherwise noted, the technical terms herein are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

The present disclosure provides for BCMA antibodies or fragments thereof as well as chimeric antigen receptors (CARs) having such BCMA antigen binding domains. The enhancement of the functional activity of the CAR directly relates to the enhancement of functional activity of the CAR-expressing T cell. As a result of one or more of these modifications, the CARs exhibit both a high degree of cytokine-induced cytolysis and cell surface expression on transduced T cells, along with an increased level of in vivo T cell expansion and persistence of the transduced CAR-expressing T cell.

The unique ability to combine functional moieties derived from different protein domains has been a key innovative feature of Chimeric Antigen Receptors (CARs). The choice of each of these protein domains is a key design feature, as is the way in which they are specifically combined. Each design domain is an essential component that can be used across different CAR platforms to engineer the function of lymphocytes. For example, the choice of the extracellular binding domain can make an otherwise ineffective CAR be effective.

The invariable framework components of the immunoglobulin-derived protein sequences used to create the extracellular antigen binding domain of a CAR can either be entirely neutral, or they can self-associate and drive the T cell to a state of metabolic exhaustion, thus making the therapeutic T cell expressing that CAR far less effective. This occurs independently of the antigen binding function of this CAR domain. Furthermore, the choice of the intracellular signaling domain(s) also can govern the activity and the durability of the therapeutic lymphocyte population used for immunotherapy. While the ability to bind target antigen and the ability to transmit an activation signal to the T cell through these extracellular and intracellular domains, respectively, are important CAR design aspects, what has also become apparent is that the choice of the source of the extracellular antigen binding fragments can have a significant effect on the efficacy of the CAR and thereby have a defining role for the function and clinical utility of the CAR.

Surprisingly and unexpectedly it has now been discovered that use of an entirely human antigen binding domain in a CAR, rather than using mouse-derived antigen binding fragments which are prone to induce anti-mouse immune response and CAR T elimination in a host (c.f., the UPenn-sponsored clinical trial using mouse derived SS1 ScFv sequence, NCT02159716), may also determine the functional activity of a CAR-expressing T cell.

The CARs disclosed herein are expressed at a high level in a cell. A cell expressing the CAR has a high in vivo proliferation rate, produces large amounts of cytokines, and has a high cytotoxic activity against a cell having, on its surface, a BCMA antigen to which a CAR binds. The use of a human extracellular BCMA antigen binding domain results in generation of a CAR that functions better in vivo, while avoiding the induction of anti-CAR immunity in the host immune response and the killing of the CAR T cell population. The CARs expressing the entirely human extracellular BCMA ScFv antigen binding domain exhibit superior activities/properties including i) prevention of poor CAR T persistence and function as seen with mouse-derived binding sequences; ii) lack of regional (i.e. intrapleural) delivery of the CAR to be efficacious; and iii) ability to generate CAR T cell designs based both on binders with high and low affinity to BCMA. This latter property allows investigators to better tune efficacy vs toxicity, and/or tissue specificity of the CAR T product, since lower-affinity binders may have higher specificity to tumors vs normal tissues due to higher expression of BCMA on tumors than normal tissue, which may prevent on-target off tumor toxicity and bystander cell killing.

What follows is a detailed description of the inventive CARs including a description of their extracellular BCMA antigen binding domain, the transmembrane domain and the intracellular domain, along with additional description of the CARs, antibodies and antigen binding fragments thereof, conjugates, nucleotides, expression, vectors, and host cells, methods of treatment, compositions, and kits employing the disclosed CARs.

A. Chimeric Antigen Receptors (CARs)

The CARs disclosed herein comprise at least one BCMA antigen binding domain capable of binding to BCMA, at least one transmembrane domain, and at least one intracellular domain.

A chimeric antigen receptor (CAR) is an artificially constructed hybrid protein or polypeptide containing the antigen binding domains of an antibody (e.g., single chain variable fragment (ScFv)) linked to T-cell signaling domains via the transmembrane domain. Characteristics of CARs include their ability to redirect T-cell specificity and reactivity toward a selected target in a non-MHC-restricted manner, and exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

As disclosed herein, the intracellular T cell signaling domains of the CARs can include, for example, a T cell receptor signaling domain, a T cell costimulatory signaling domain, or both. The T cell receptor signaling domain refers to a portion of the CAR comprising the intracellular domain of a T cell receptor, such as, for example, and not by way of limitation, the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen.

1. Extracellular Domain

In one embodiment, the CAR comprises a target-specific binding element otherwise referred to as an antigen binding domain or moiety. The choice of domain depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen binding domain in the CAR include those associated with viral, bacterial and parasitic infections, autoimmune disease and cancer cells.

In one embodiment, the CAR can be engineered to target a tumor antigen of interest by way of engineering a desired antigen binding domain that specifically binds to an antigen on a tumor cell. Tumor antigens are proteins that are produced by tumor cells that elicit an immune response, particularly T-cell mediated immune responses. The selection of the antigen binding domain will depend on the particular type of cancer to be treated. Tumor antigens include, for example, a glioma-associated antigen, carcinoembryonic antigen (CEA), .beta.-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-la, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and BCMA. The tumor antigens disclosed herein are merely included by way of example. The list is not intended to be exclusive and further examples will be readily apparent to those of skill in the art.

In one embodiment, the tumor antigen comprises one or more antigenic cancer epitopes associated with a malignant tumor. Malignant tumors express a number of proteins that can serve as target antigens for an immune attack. These molecules include, but are not limited to, tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

In one preferred embodiment, the tumor antigen is BCMA and the tumors associated with expression of BCMA comprise lung mesothelioma, ovarian, and pancreatic cancers that express high levels of the extracellular protein BCMA, or any combination thereof.

The type of tumor antigen may also be a tumor-specific antigen (TSA) or a tumor-associated antigen (TAA). A TSA is unique to tumor cells and does not occur on other cells in the body. A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSAs or TAAs include the following: Differentiation antigens such as MART-1/MelanA (MART-I), gp100 (Pmel 17), tyrosinase, TRP-1, TRP-2 and tumor-specific multi-lineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCASI, SDCCAG16, TA-90\Mac-2 binding protein\cyclophilin C-associated protein, TAAL6, TAG72, TLP, and TPS.

In one embodiment, the antigen binding domain portion of the CAR targets an antigen that includes but is not limited to CD19, CD20, CD22, ROR1, CD33, c-Met, PSMA, Glycolipid F77, EGFRVIII, GD-2, MY-ESO-1 TCR, MAGE A3 TCR, and the like.

In a preferred embodiment, the antigen binding domain portion of the CAR targets the extracellular BCMA antigen.

In one preferred embodiment, the isolated nucleic acid molecule encoding the extracellular BCMA ScFv Clone 5 D0084 antigen binding domain comprises a nucleotide sequence of SEQ ID NO: 9, or a sequence with 85%, 90%, 95%, 96%, 97%, 98% or 99% identity thereof. In one embodiment, an isolated nucleic acid molecule is provided wherein the encoded extracellular BCMA ScFv Clone 5 D0084 antigen binding domain comprises an amino acid sequence of SEQ ID NO: 10, or an amino acid sequence with 85%, 90%, 95%, 96%, 97%, 98% or 99% identity to an amino acid sequence of SEQ ID NO: 10.

In one preferred embodiment, the isolated nucleic acid molecule encoding the extracellular BCMA ScFv Clone 16 D0085 antigen binding domain comprises a nucleotide sequence of SEQ ID NO: 17, or a sequence with 85%, 90%, 95%, 96%, 97%, 98% or 99% identity thereof. In one embodiment, an isolated nucleic acid molecule is provided wherein the encoded extracellular BCMA ScFv Clone 16 D0085 antigen binding domain comprises an amino acid sequence of SEQ ID NO: 18, or an amino acid sequence with 85%, 90%, 95%, 96%, 97%, 98% or 99% identity to an amino acid sequence of SEQ ID NO: 18.

In one preferred embodiment, the isolated nucleic acid molecule encoding the extracellular BCMA ScFv Clone 37 D0086 antigen binding domain comprises a nucleotide sequence of SEQ ID NO: 23, or a sequence with 85%, 90%, 95%, 96%, 97%, 98% or 99% identity thereof. In one embodiment, an isolated nucleic acid molecule is provided wherein the encoded extracellular BCMA ScFv Clone 37 D0086 antigen binding domain comprises an amino acid sequence of SEQ ID NO: 24, or an amino acid sequence with 85%, 90%, 95%, 96%, 97%, 98% or 99% identity to an amino acid sequence of SEQ ID NO: 24.

In one preferred embodiment, the isolated nucleic acid molecule encoding the extracellular BCMA ScFv Clone 40 D0087 antigen binding domain comprises a nucleotide sequence of SEQ ID NO: 69, or a sequence with 85%, 90%, 95%, 96%, 97%, 98% or 99% identity thereof. In one embodiment, an isolated nucleic acid molecule is provided wherein the encoded extracellular BCMA ScFv Clone 40 D0087 antigen binding domain comprises an amino acid sequence of SEQ ID NO: 70, or an amino acid sequence with 85%, 90%, 95%, 96%, 97%, 98% or 99% identity to an amino acid sequence of SEQ ID NO: 70.

In one preferred embodiment, the isolated nucleic acid molecule encoding the extracellular BCMA ScFv Clone 4-12 D0099 antigen binding domain comprises a nucleotide sequence of SEQ ID NO: 75, or a sequence with 85%, 90%, 95%, 96%, 97%, 98% or 99% identity thereof. In one embodiment, an isolated nucleic acid molecule is provided wherein the encoded extracellular BCMA ScFv Clone 4-12 D0099 antigen binding domain comprises an amino acid sequence of SEQ ID NO: 76, or an amino acid sequence with 85%, 90%, 95%, 96%, 97%, 98% or 99% identity to an amino acid sequence of SEQ ID NO: 76.

In one preferred embodiment, the isolated nucleic acid molecule encoding the extracellular BCMA ScFv Clone 4-45 D0100 antigen binding domain comprises a nucleotide sequence of SEQ ID NO: 77, or a sequence with 85%, 90%, 95%, 96%, 97%, 98% or 99% identity thereof. In one embodiment, an isolated nucleic acid molecule is provided wherein the encoded extracellular BCMA ScFv Clone 4-45 D0100 antigen binding domain comprises an amino acid sequence of SEQ ID NO: 78, or an amino acid sequence with 85%, 90%, 95%, 96%, 97%, 98% or 99% identity to an amino acid sequence of SEQ ID NO: 78.

In one preferred embodiment, the isolated nucleic acid molecule encoding the extracellular 4-1c VH antigen binding domain comprises a nucleotide sequence of SEQ ID NO: 103, or a sequence with 85%, 90%, 95%, 96%, 97%, 98% or 99% identity thereof. In one embodiment, an isolated nucleic acid molecule is provided wherein the encoded extracellular 4-1c VH antigen binding domain comprises an amino acid sequence of SEQ ID NO: 104, or an amino acid sequence with 85%, 90%, 95%, 96%, 97%, 98% or 99% identity to an amino acid sequence of SEQ ID NO: 104.

In one preferred embodiment, the isolated nucleic acid molecule encoding the extracellular 4-1c VL antigen binding domain comprises a nucleotide sequence of SEQ ID NO: 105, or a sequence with 85%, 90%, 95%, 96%, 97%, 98% or 99% identity thereof. In one embodiment, an isolated nucleic acid molecule is provided wherein the encoded extracellular 4-1c VL antigen binding domain comprises an amino acid sequence of SEQ ID NO: 106, or an amino acid sequence with 85%, 90%, 95%, 96%, 97%, 98% or 99% identity to an amino acid sequence of SEQ ID NO: 106.

In one preferred embodiment, the isolated nucleic acid molecule encoding the extracellular TGFBRIIdn domain comprises a nucleotide sequence of SEQ ID NO: 109, or a sequence with 85%, 90%, 95%, 96%, 97%, 98% or 99% identity thereof. In one embodiment, an isolated nucleic acid molecule is provided wherein the encoded extracellular TGFBRIIdn domain comprises an amino acid sequence of SEQ ID NO: 110, or an amino acid sequence with 85%, 90%, 95%, 96%, 97%, 98% or 99% identity to an amino acid sequence of SEQ ID NO: 110.

The generation and binding characteristics of the specific BCMA ScFv antigen binding fragments described herein is shown in Example 1.

In the various embodiments of the BCMA-specific CARs disclosed herein, the general scheme is set forth in FIG. 1 and includes, from the N-terminus to the C-terminus, a signal or leader peptide, anti-BCMA ScFv, extracellular linker, CD8 transmembrane, 4-1BB, CD3 zeta, wherein the bolded text represents the cloning sites for linking domains.

In one embodiment, the nucleic acid sequence encoding a CAR comprises the nucleic acid sequence of SEQ ID NO: 87, and encodes the CAR comprising the amino acid sequence as set forth in SEQ ID NO: 88.

In one embodiment, the nucleic acid sequence encoding a CAR comprises the nucleic acid sequence of SEQ ID NO: 87, or a sequence with 85%, 90%, 95%, 96%, 97%, 98% or 99% identity thereof, and encodes the CAR comprising the amino acid sequence as set forth in SEQ ID NO: 88 or a sequence with 85%, 90%, 95%, 96%, 97%, 98% or 99% identity thereof.

In another embodiment, the nucleic acid sequence encoding a CAR comprises the nucleic acid sequence of SEQ ID NO: 89, and encodes the CAR comprising the amino acid sequence as set forth in SEQ ID NO: 90.

In another embodiment, the nucleic acid sequence encoding a CAR comprises the nucleic acid sequence of SEQ ID NO: 89 or a sequence with 85%, 90%, 95%, 96%, 97%, 98% or 99% identity thereof, and encodes the CAR comprising the amino acid sequence as set forth in SEQ ID NO: 90 or a sequence with 85%, 90%, 95%, 96%, 97%, 98% or 99% identity thereof.

In another embodiment, the nucleic acid sequence encoding a CAR comprises the nucleic acid sequence of SEQ ID NO: 91, and encodes the CAR comprising the amino acid sequence as set forth in SEQ ID NO: 92.

In another embodiment, the nucleic acid sequence encoding a CAR comprises the nucleic acid sequence of SEQ ID NO: 91 or a sequence with 85%, 90%, 95%, 96%, 97%, 98% or 99% identity thereof, and encodes the CAR comprising the amino acid sequence as set forth in SEQ ID NO: 92 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 93, and encodes the CAR comprising the amino acid sequence as set forth in SEQ ID NO: 94.

In yet another embodiment, the nucleic acid sequence encoding a CAR comprises the nucleic acid sequence of SEQ ID NO: 93 or a sequence with 85%, 90%, 95%, 96%, 97%, 98% or 99% identity thereof, and encodes the CAR comprising the amino acid sequence as set forth in SEQ ID NO: 94 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 95, and encodes the CAR comprising the amino acid sequence as set forth in SEQ ID NO: 96.

In yet another embodiment, the nucleic acid sequence encoding a CAR comprises the nucleic acid sequence of SEQ ID NO: 95 or a sequence with 85%, 90%, 95%, 96%, 97%, 98% or 99% identity thereof, and encodes the CAR comprising the amino acid sequence as set forth in SEQ ID NO: 96 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 97, and encodes the CAR comprising the amino acid sequence as set forth in SEQ ID NO: 98.

In yet another embodiment, the nucleic acid sequence encoding a CAR comprises the nucleic acid sequence of SEQ ID NO: 99, and encodes the CAR comprising the amino acid sequence as set forth in SEQ ID NO: 100.

In yet another embodiment, the nucleic acid sequence encoding a CAR comprises the nucleic acid sequence of SEQ ID NO: 101, and encodes the CAR comprising the amino acid sequence as set forth in SEQ ID NO: 102.

In yet another embodiment, the nucleic acid sequence encoding a CAR comprises the nucleic acid sequence of SEQ ID NO: 97 or a sequence with 85%, 90%, 95%, 96%, 97%, 98% or 99% identity thereof, and encodes the CAR comprising the amino acid sequence as set forth in SEQ ID NO: 98 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 99 or a sequence with 85%, 90%, 95%, 96%, 97%, 98% or 99% identity thereof, and encodes the CAR comprising the amino acid sequence as set forth in SEQ ID NO: 100 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 101 or a sequence with 85%, 90%, 95%, 96%, 97%, 98% or 99% identity thereof, and encodes the CAR comprising the amino acid sequence as set forth in SEQ ID NO: 102 or a sequence with 85%, 90%, 95%, 96%, 97%, 98% or 99% identity thereof.

The surface expression of anti-BCMA CARs incorporating immunoglobulin single chain fragment variable (ScFv) sequences reactive with BCMA antigen, is shown in Example 2 infra. The expression level for each ScFv-containing CAR was determined by flow cytometric analysis of LV-transduced T cells from healthy donors using a recombinant BCMA-Fc peptide, followed by anti-human Fc F(ab') 2 fragment conjugated to AF647, and detected in the APC channel, (c.f., Example 2, FIG. 2). Alternatively, CAR detection was performed using protein L-biotin conjugate, followed by Streptavidin-PE, with similar results (Example 2, FIG. 2). Further confirmation of CAR expression for constructs selected for further investigation was performed using the BCMA-Fc staining method (Example 2, FIG. 4). All anti-BCMA CAR constructs were readily detected on the surface of T cells, except for the sequence 15 CAR construct, demonstrating robust CAR expression. By contrast, no CAR expression was detected in the negative control non-transduced T cells (UTD), thus demonstrating the specificity of the detection method used (c.f., Example 2, FIG. 2, FIG. 4).

Without being intended to limit to any particular mechanism of action, it is believed that possible reasons for the enhanced therapeutic function associated with the exemplary CARs of the invention include, for example, and not by way of limitation, a) improved lateral movement within the plasma membrane allowing for more efficient signal transduction, b) superior location within plasma membrane microdomains, such as lipid rafts, and greater ability to interact with transmembrane signaling cascades associated with T cell activation, c) superior location within the plasma membrane by preferential movement away from dampening or down-modulatory interactions, such as less proximity to or interaction with phosphatases such as CD45, and d) superior assembly into T cell receptor signaling complexes (i.e. the immune synapse), or any combination thereof.

While the disclosure has been illustrated with an exemplary extracellular BCMA ScFv antigen binding domains, other nucleotide and/or amino acid variants within the BCMA variable ScFv antigen binding domains may be used to derive the BCMA antigen binding domains for use in the CARs described herein.

Depending on the desired antigen to be targeted, the CAR can be additionally engineered to include the appropriate antigen binding domain that is specific to the desired antigen target. For example, if CD19 is the desired antigen that is to be targeted, an antibody for CD19 can be used as the antigen bind domain incorporation into the CAR.

In one exemplary embodiment, the antigen binding domain portion of the CAR additionally targets CD19. Preferably, the antigen binding domain in the CAR is anti-CD19 ScFv, wherein the nucleic acid sequence of the anti-CD19 ScFv comprises the sequence set forth in SEQ ID NO: 37 In one embodiment, the anti-CD19 ScFv comprises the nucleic acid sequence that encodes the amino acid sequence of SEQ ID NO: 30. In another embodiment, the anti-CD19 ScFv portion of the CAR comprises the amino acid sequence set forth in SEQ ID NO: 38.

In one aspect of the present invention, there is provided a CAR capable of binding to a non-TSA or non-TAA including, for example and not by way of limitation, an antigen derived from Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, Ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus, or any combination thereof.

In another aspect of the present invention, there is provided a CAR capable of binding to an antigen derived from a bacterial strain of Staphylococci, *Streptococcus, Escherichia coli, Pseudomonas*, or *Salmonella*. Particularly, there is provided a CAR capable of binding to an antigen derived from an infectious bacterium, for example, *Helicobacter pyloris, Legionella* pneumophilia, a bacterial strain of Mycobacteria sps. (e.g. *M. tuberculosis, M. avium, M. intracellulare, M. kansaii*, or *M. gordonea*), *Staphylococcus aureus, Neisseria gonorrhoeae, Neisseria meningitides, Listeria monocytogenes, Streptococcus pyogenes*, Group A *Streptococcus*, Group B *Streptococcus* (*Streptococcus agalactiae*), *Streptococcus pneumoniae*, or *Clostridium tetani*, or a combination thereof.

2. Transmembrane Domain

With respect to the transmembrane domain, the CAR comprises one or more transmembrane domains fused to the extracellular BCMA antigen binding domain of the CAR.

The transmembrane domain may be derived either from a natural or from a synthetic source. Where the source is natural, the domain may be derived from any membrane-bound or transmembrane protein.

Transmembrane regions of particular use in the CARs described herein may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, mesothelin, CD33, CD37, CD64, CD80, CD86, CD134, CD137, CD154. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain that naturally is associated with one of the domains in the CAR is used in addition to the transmembrane domains described supra.

In some instances, the transmembrane domain can be selected by amino acid substitution to avoid binding of such domains to the transmembrane domains of the same or different surface membrane proteins to minimize interactions with other members of the receptor complex.

In one embodiment, the transmembrane domain in the CAR of the invention is the CD8 transmembrane domain. In one embodiment, the CD8 transmembrane domain comprises the nucleic acid sequence of SEQ ID NO: 27. In one embodiment, the CD8 transmembrane domain comprises the nucleic acid sequence that encodes the amino acid sequence of SEQ ID NO: 28. In another embodiment, the CD8 transmembrane domain comprises the amino acid sequence of SEQ ID NO: 28.

In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO: 28, or a sequence with 95-99% identity to an amino acid sequence of SEQ ID NO: 28.

In some instances, the transmembrane domain of the CAR comprises the CD8.alpha.hinge domain. In one embodiment, the CD8 hinge domain comprises the nucleic acid sequence of SEQ ID NO: 29. In one embodiment, the CD8 hinge domain comprises the nucleic acid sequence that encodes the amino acid sequence of SEQ ID NO: 30. In another embodiment, the CD8 hinge domain comprises the amino acid sequence of SEQ ID NO: 30, or a sequence with 95-99% identify thereof.

In one embodiment, an isolated nucleic acid molecule is provided wherein the encoded linker domain is derived from the extracellular domain of CD8, and is linked to the transmembrane CD8 domain, the transmembrane CD28 domain, or a combination thereof.

In one embodiment, the transmembrane domain in the CAR of the invention is the TNFRSF19 transmembrane domain. In one embodiment, the TNFRSF19 transmembrane domain comprises the nucleic acid sequence of SEQ ID NO: 51. In one embodiment, the TNFRSF19 transmembrane domain comprises the nucleic acid sequence that encodes the amino acid sequence of SEQ ID NO: 52. In another embodiment, the TNFRSF19 transmembrane domain comprises the amino acid sequence of SEQ ID NO: 52.

In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO: 52, or a sequence with 95-99% identity to an amino acid sequence of SEQ ID NO: 52.

3. Spacer Domain

In the CAR, a spacer domain, also termed hinge domain, can be arranged between the extracellular domain and the transmembrane domain, or between the intracellular domain and the transmembrane domain. The spacer domain means any oligopeptide or polypeptide that serves to link the transmembrane domain with the extracellular domain and/or the transmembrane domain with the intracellular domain. The spacer domain comprises up to 300 amino acids, preferably 10 to 100 amino acids, and most preferably 25 to 50 amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,5667, 498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

The spacer domain preferably has a sequence that promotes binding of a CAR with an antigen and enhances signaling into a cell. Examples of an amino acid that is expected to promote the binding include cysteine, a charged amino acid, and serine and threonine in a potential glycosylation site, and these amino acids can be used as an amino acid constituting the spacer domain.

As the spacer domain, the entire or a part of amino acid numbers 118 to 178 (SEQ ID NO: 31) which is a hinge region of CD8.alpha. (NCBI RefSeq: NP.sub.-001759.3), amino acid numbers 135 to 195 of CD8.beta. (GenBank: AAA35664.1), amino acid numbers 315 to 396 of CD4 (NCBI RefSeq: NP.sub.-000607.1), or amino acid numbers 137 to 152 of CD28 (NCBI RefSeq: NP.sub.-006130.1) can be used. Also, as the spacer domain, a part of a constant region of an antibody H chain or L chain (CH1 region or CL region, for example, a peptide having an amino acid sequence shown in SEQ ID NO: 32) can be used. Further, the spacer domain may be an artificially synthesized sequence.

In addition, an entire or a part of amino acids comprising the constant region of a human IgG4 (UniProt ID: P01861), including CH1, (amino acid numbers 1-98), hinge, SEQ ID NO: 80, and the corresponding nucleotide SEQ ID NO: 79, (amino acid numbers 99-110), CH2, amino acid SEQ ID NO: 81 and corresponding nucleotide SEQ ID NO: 80, (amino acid numbers 111-220) and CH3, SEQ ID NO: 84 and corresponding nucleotide SEQ ID NO: 83, (amino acid numbers 221-327) or a combination thereof, such as IgG4 Hinge CH2 CH3 domain, SEQ ID NO: 86, and the corresponding nucleotide SEQ ID NO: 85, can be used.

In one embodiment, the spacer domain of the CAR comprises the TNFRSF19 hinge domain which comprises the nucleic acid sequence of SEQ ID NO: 53. In one embodiment, the TNFRSF19 hinge domain comprises the nucleic acid sequence that encodes the amino acid sequence of SEQ ID NO: 54. In another embodiment, the TNFRSF19 hinge domain comprises the amino acid sequence of SEQ ID NO: 54, or a sequence with 95-99% identify thereof.

In one embodiment, the spacer domain of the CAR comprises the TNFRSF19 truncated hinge domain comprises the nucleic acid sequence of SEQ ID NO: 55. In one embodiment, the TNFRSF19 truncated hinge domain comprises the nucleic acid sequence that encodes the amino acid sequence of SEQ ID NO: 56. In another embodiment, the TNFRSF19 truncated hinge domain comprises the amino acid sequence of SEQ ID NO: 56, or a sequence with 95-99% identify thereof.

In one embodiment, the TNFRSF19 hinge and transmembrane domains comprise the nucleic acid sequence of SEQ ID NO: 49. In one embodiment, the TNFRSF19 hinge and transmembrane domains comprise the nucleic acid sequence that encodes the amino acid sequence of SEQ ID NO: 50. In another embodiment, the TNFRSF19 hinge and transmembrane domains comprise the amino acid sequence of SEQ ID NO: 50, or a sequence with 95-99% identify thereof.

In one embodiment, a CD8a hinge domain is fused to a TNFRSF19 transmembrane domain comprising the nucleic acid sequence of SEQ ID NO: 57. In one embodiment, the CD8a hinge domain is fused to a TNFRSF19 transmembrane domain comprises the nucleic acid sequence that encodes the amino acid sequence of SEQ ID NO: 58. In another embodiment, the CD8a hinge domain is fused to a TNFRSF19 transmembrane domain comprises the amino acid sequence of SEQ ID NO: 58, or a sequence with 95-99% identify thereof.

Further, in the CAR, a signal peptide sequence, also termed leader peptide, can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the CAR. In one embodiment, the signal peptide comprises the amino acid sequence shown in SEQ ID NO: 14).

In one embodiment, the CD8 alpha leader peptide, is comprising the nucleic acid sequence of SEQ ID NO: 43. In one embodiment, CD8 alpha leader peptide comprises the nucleic acid sequence that encodes the amino acid sequence of SEQ ID NO: 44. In another embodiment, the CD8a hinge domain is fused to a TNFRSF19 transmembrane domain comprises the amino acid sequence of SEQ ID NO: 44, or a sequence with 95-99% identify thereof.

In another embodiment, the GMCSF leader peptide, is comprising the nucleic acid sequence of SEQ ID NO: 39. In one embodiment, the GMCSF leader peptide, comprises the nucleic acid sequence that encodes the amino acid sequence of SEQ ID NO: 40. In another embodiment, the CD8a hinge domain is fused to a TNFRSF19 transmembrane domain comprises the amino acid sequence of SEQ ID NO: 40, or a sequence with 95-99% identify thereof.

In another embodiment, the TNFRSF19 leader peptide is comprising the nucleic acid sequence of SEQ ID NO: 41. In one embodiment, TNFRSF19 leader peptide, and CD8 alpha leader peptide comprises the nucleic acid sequence that encodes the amino acid sequence of SEQ ID NO: 42. In another embodiment, the CD8a hinge domain is fused to a TNFRSF19 transmembrane domain comprises the amino acid sequence of SEQ ID NO: 42, or a sequence with 95-99% identify thereof.

In one embodiment, a tag sequence encoding a truncated sequence of epidermal growth factor receptor (EGFR) is comprising the nucleic acid sequence of SEQ ID NO: 67. In one embodiment, tEGFR comprises the nucleic acid sequence that encodes the amino acid sequence of SEQ ID NO: 68. In another embodiment, the tEGFR tag comprises the amino acid sequence of SEQ ID NO: 68, or a sequence with 95-99% identify thereof.

In one embodiment, a furin recognition site and downstream T2A self-cleaving peptide sequence, designed for simultaneous bicistronic expression of the tag sequence and the CAR sequence, is comprising the nucleic acid sequence of SEQ ID NO: 65. In one embodiment, furin and T2A sequence comprises the nucleic acid sequence that encodes the amino acid sequence of SEQ ID NO: 66. In another embodiment, the tEGFR tag comprises the amino acid sequence of SEQ ID NO: 66 or a sequence with 95-99% identify thereof.

In one embodiment, an upstream furin recognition site and T2A self-cleaving peptide sequence and a furin recognition downstream site, designed for simultaneous bicistronic expression of the tag sequence and the CAR sequence, is comprising the nucleic acid sequence of SEQ ID NO: 67. In one embodiment, furin and T2A sequence comprises the nucleic acid sequence that encodes the amino acid sequence of SEQ ID NO: 68. In another embodiment, the tEGFR tag comprises the amino acid sequence of SEQ ID NO: 68 or a sequence with 95-99% identify thereof.

In one embodiment, the targeting domain of the CAR is expressed separately in the form of monoclonal antibody, ScFv Fab, Fab'2 and is containing at binding tag or epitope, whereas the effector-cell expressed component of the CAR contains a binding domain specifically directed to bind the tag or epitope expressed on the soluble CAR module, such as specific binding on the soluble component of the CAR to the cell bound component forms the full functional CAR structure.

4. Intracellular Domain

The cytoplasmic domain or otherwise the intracellular signaling domain of the CAR is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus, the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the CARs disclosed herein include those derived from TCR zeta (CD3 Zeta), FcR gamma, FcR beta, CD3 gamma, CD3 delta, CD3 epsilon, CD5, CD22, CD79a, CD79b, and CD66d. Specific, non-limiting examples, of the ITAM include peptides having sequences of amino acid numbers 51 to 164 of CD3.zeta. (NCBI RefSeq: NP.sub.-932170.1), amino acid numbers 45 to 86 of Fc.epsilon.RI.gamma. (NCBI RefSeq: NP.sub.-004097.1), amino acid numbers 201 to 244 of Fc.epsilon.RI.beta. (NCBI RefSeq: NP.sub.-000130.1), amino acid numbers 139 to 182 of CD3.gamma. (NCBI RefSeq: NP.sub.-000064.1), amino acid numbers 128 to 171 of CD3.delta. (NCBI RefSeq: NP.sub.-000723.1), amino acid numbers 153 to 207 of CD3.epsilon. (NCBI RefSeq: NP.sub.-000724.1), amino acid numbers 402 to 495 of CD5 (NCBI RefSeq: NP.sub.-055022.2), amino acid numbers 707 to 847 of 0022 (NCBI RefSeq: NP.sub.-001762.2), amino acid numbers 166 to 226 of CD79a (NCBI RefSeq: NP.sub.-001774.1), amino acid numbers 182 to 229 of CD79b (NCBI RefSeq: NP.sub.-000617.1), and amino acid numbers 177 to 252 of CD66d (NCBI RefSeq: NP.sub.-001806.2), and their variants having the same function as these peptides have. The amino acid number based on amino acid sequence information of NCBI RefSeq ID or GenBank described herein is numbered based on the full length of the precursor (comprising a signal peptide sequence etc.) of each protein. In one embodiment, the cytoplasmic signaling molecule in the CAR comprises a cytoplasmic signaling sequence derived from CD3 zeta.

In a preferred embodiment, the intracellular domain of the CAR can be designed to comprise the CD3-zeta signaling domain by itself or combined with any other desired cytoplasmic domain(s) useful in the context of the CAR. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such costimulatory molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Specific, non-limiting examples, of such costimulatory molecules include peptides having sequences of amino acid numbers 236 to 351 of CD2 (NCBI RefSeq: NP.sub.-001758.2), amino acid numbers 421 to 458 of CD4 (NCBI RefSeq: NP.sub.-000607.1), amino acid numbers 402 to 495 of CD5 (NCBI RefSeq: NP.sub.-055022.2), amino acid numbers 207 to 235 of CD8.alpha. (NCBI RefSeq: NP.sub.-001759.3), amino acid numbers 196 to 210 of CD83 (GenBank: AAA35664.1), amino acid numbers 181 to 220 of CD28 (NCBI RefSeq: NP.sub.-006130.1), amino acid numbers 214 to 255 of CD137 (4-1BB, NCBI RefSeq: NP.sub.-001552.2), amino acid numbers 241 to 277 of CD134 (OX40, NCBI RefSeq: NP.sub.-003318.1), and amino acid numbers 166 to 199 of ICOS (NCBI RefSeq: NP.sub.-036224.1), and their variants having the same function as these peptides have. Thus, while the disclosure herein is exemplified primarily with 4-1BB as the co-stimulatory signaling element, other costimulatory elements are within the scope of the disclosure.

The cytoplasmic signaling sequences within the cytoplasmic signaling portion of the CAR may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB. In yet another embodiment, the intracellular domain is designed to comprise the signaling domain of CD3-zeta and the signaling domain of CD28 and 4-1BB.

In one embodiment, the intracellular domain in the CAR is designed to comprise the signaling domain of 4-1BB and the signaling domain of CD3-zeta, wherein the signaling domain of 4-1BB comprises the nucleic acid sequence set forth in SEQ ID NO: 33, SEQ ID NO: 45, or SEQ ID NO: 59, respectively and the signaling domain of CD3-zeta comprises the nucleic acid sequence set forth in SEQ ID NO: 35, SEQ ID NO: 47, or SEQ ID NO: 61, respectively.

In one embodiment, the intracellular domain in the CAR is designed to comprise the signaling domain of 4-1BB and the signaling domain of CD3-zeta, wherein the signaling domain of 4-1BB comprises the nucleic acid sequence that encodes the amino acid sequence of SEQ ID NO: 34, SEQ ID NO: 46, or SEQ ID NO: 60, respectively and the signaling domain of CD3-zeta comprises the nucleic acid sequence that encodes the amino acid sequence of SEQ ID NO: 36, or SEQ ID NO: 48, or SEQ ID NO: 62.

In one embodiment, the intracellular domain in the CAR is designed to comprise the signaling domain of 4-1BB and the signaling domain of CD3-zeta, wherein the signaling domain of 4-1BB comprises the amino acid sequence set forth in SEQ ID NO: 34, SEQ ID NO: 46, or SEQ ID NO: 60, respectively and the signaling domain of CD3-zeta comprises the amino acid sequence set forth in SEQ ID NO: 36, SEQ ID NO: 48, or SEQ ID NO: 62, respectively.

In one embodiment, the intracellular domain in the CAR is designed to comprise the signaling domain of CD28 and the signaling domain of CD3-zeta, wherein the signaling domain of CD28 comprises the nucleic acid sequence set forth in SEQ ID NO: 45, or SEQ ID NO: 59, respectively, and the signaling domain of CD3-zeta comprises the nucleic acid sequence set forth in SEQ ID NO: 35, SEQ ID NO: 47, or SEQ ID NO: 61, respectively.

In one embodiment, the intracellular domain in the CAR is designed to comprise the signaling domain of CD28 and the signaling domain of CD3-zeta, wherein the signaling domain of CD28 comprises the nucleic acid sequence that encodes the amino acid sequence of SEQ ID NO: 46, or SEQ ID NO: 60, respectively and the signaling domain of CD3-zeta comprises the nucleic acid sequence that encodes the amino acid sequence of SEQ ID NO: 36, or SEQ ID NO: 48, or SEQ ID NO: 62.

In one embodiment, the intracellular domain in the CAR is designed to comprise the signaling domain of CD28 and the signaling domain of CD3-zeta, wherein the signaling domain of CD28 comprises the amino acid sequence set forth in SEQ ID NO: 46, or SEQ ID NO: 60, respectively and the signaling domain of CD3-zeta comprises the amino acid sequence set forth in SEQ ID NO: 36, SEQ ID NO: 48, or SEQ ID NO: 62, respectively.

5. Additional Description of CARs

Also expressly included within the scope of the invention are functional portions of the CARs disclosed herein. The term "functional portion" when used in reference to a CAR refers to any part or fragment of one or more of the CARs disclosed herein, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the disclosure are functional variants of the CARs disclosed herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, He, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., He, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine,-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine,-aminocyclopentane carboxylic acid, α-aminocyclohexane carboxylic acid, α-aminocycloheptane carboxylic acid, a-(2-amino-2-norbornane)-carboxylic acid, γ-diaminobutyric acid, β-diaminopropionic acid, homophenylalanine, and a-tert-butylglycine.

The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, 3rd ed., Cold Spring Harbor Press, Cold Spring Harbor, NY 2001; and Ausubel et al., Current Protocols in Molecular Biology, Greene Publishing Associates and John Wiley & Sons, NY, 1994. Further, some of the CARs (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies. In this respect, the CARs can be synthetic, recombinant, isolated, and/or purified.

B. Antibodies and Antigen Binding Fragments

One embodiment further provides a CAR, a T cell expressing a CAR, an antibody, or antigen binding domain or portion thereof, which specifically binds to one or more of the antigens disclosed herein. As used herein, a "T cell expressing a CAR," or a "CAR T cell" means a T cell expressing a CAR, and has antigen specificity determined by, for example, the antibody-derived targeting domain of the CAR.

As used herein, and "antigen binding domain" can include an antibody and antigen binding fragments thereof. The term "antibody" is used herein in the broadest sense and encompasses various antibody structures, including but not limited to monoclonal antibodies, polyclonal antibodies, multi-specific antibodies (e.g., bispecific antibodies), and antigen binding fragments thereof, so long as they exhibit the desired antigen-binding activity. Non-limiting examples of antibodies include, for example, intact immunoglobulins and variants and fragments thereof known in the art that retain binding affinity for the antigen.

A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. In some examples, a monoclonal antibody is an antibody produced by a single clone of B lymphocytes or by a cell into which nucleic acid encoding the light and heavy variable regions of the antibody of a single antibody (or an antigen binding fragment thereof) have been transfected, or a progeny thereof. In some examples monoclonal antibodies are isolated from a subject. Monoclonal antibodies can have conservative amino acid substitutions which have substantially no effect on antigen binding or other immunoglobulin functions. Exemplary methods of production of monoclonal antibodies are known, for example, see Harlow & Lane, Antibodies, A Laboratory Manual, 2nd ed. Cold Spring Harbor Publications, New York (2013).

Typically, an immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, $6^{th}$ ed., W. H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). References to "VH" or "VH" refer to the variable region of an antibody heavy chain, including that of an antigen binding fragment, such as Fv, ScFv, dsFv or Fab. References to "VL" or "VL" refer to the variable domain of an antibody light chain, including that of an Fv, ScFv, dsFv or Fab. Light and heavy chain variable regions contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," $5^{th}$ Ed. Public Health Service, National Institutes of Health, Bethesda, MD, 1991; "Kabat" numbering scheme), Al-Lazikani et al., (JMB 273,927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a VH CDR3 is the CDR3 from the variable domain of the heavy chain of the antibody in which it is found, whereas a VL CDR1 is the CDR1 from the variable domain of the light chain of the antibody in which it is found. Light chain CDRs are sometimes referred to as LCDR1, LCDR2, and LCDR3. Heavy chain CDRs are sometimes referred to as HCDR1, HCDR2, and HCDR3.

An "antigen binding fragment" is a portion of a full length antibody that retains the ability to specifically recognize the cognate antigen, as well as various combinations of such portions. Non-limiting examples of antigen binding fragments include Fv, Fab, Fab', Fab'-SH, F(ab') 2; diabodies; linear antibodies; single-chain antibody molecules (e.g. ScFv); and multi-specific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$ Ed., Springer Press, 2010).

A single-chain antibody (ScFv) is a genetically engineered molecule containing the VH and VL domains of one or more antibody(ies) linked by a suitable polypeptide linker as a genetically fused single chain molecule (see, for example, Bird et al., Science, 242:423 426, 1988; Huston et al., Proc. Natl. Acad. Sci., 85:5879 5883, 1988; Ahmad et al., Clin. Dev. Immunol., 2012, doi: 10.1155/2012/980250; Marbry, Idrugs, 13:543-549, 2010). The intramolecular orientation of the VH-domain and the VL-domain in a ScFv, is typically not decisive for ScFvs. Thus, ScFvs with both possible arrangements (VH-domain-linker domain-VL-domain; VL-domain-linker domain-VH-domain) may be used.

In a dsFv, the heavy and light chain variable chains have been mutated to introduce a disulfide bond to stabilize the association of the chains. Diabodies also are included, which are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., Proc. Natl. Acad. Sci., 90:6444 6448, 1993; Poljak et al., Structure, 2:1121 1123, 1994).

Antibodies also include genetically engineered forms such as chimeric antibodies (such as humanized murine antibodies) and heteroconjugate antibodies (such as bispecific antibodies). See also, Pierce Catalog and Handbook, 1994-1995 (Pierce Chemical Co., Rockford, IL); Kuby, J., Immunology, $3^{rd}$ Ed., W. H. Freeman & Co., New York, 1997.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin.

Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. Phage display: A Laboratory Manuel. 1$^{st}$ Ed. New York: Cold Spring Harbor Laboratory Press, 2004. Print.; Lonberg, Nat. Biotech., 23:1117-1125, 2005; Lonenberg, Curr. Opin. Immunol., 20:450-459, 2008).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Methods of testing antibodies for the ability to bind to any functional portion of the CAR are known in the art and include any antibody-antigen binding assay, such as, for example, radioimmunoassay (RIA), ELISA, Western blot, immunoprecipitation, and competitive inhibition assays (see, e.g., Janeway et al., infra, U.S. Patent Application Publication No. 2002/0197266 A1, and U.S. Pat. No. 7,338, 929).

Also, a CAR, a T cell expressing a CAR, an antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

C. Conjugates

A CAR, a T cell expressing a CAR, or monoclonal antibodies, or antigen binding fragments thereof, specific for one or more of the antigens disclosed herein, can be conjugated to an agent, such as an effector molecule or detectable marker, using any number of means known to those of skill in the art. Both covalent and noncovalent attachment means may be used. Conjugates include, but are not limited to, molecules in which there is a covalent linkage of an effector molecule or a detectable marker to an antibody or antigen binding fragment that specifically binds one or more of the antigens disclosed herein. One of skill in the art will appreciate that various effector molecules and detectable markers can be used, including (but not limited to) chemotherapeutic agents, anti-angiogenic agents, toxins, radioactive agents such as $^{125}I$, $^{32}P$, $^{14}C$, $^{3}H$ and $^{35}S$ and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a tumor cell).

The procedure for attaching an effector molecule or detectable marker to an antibody or antigen binding fragment varies according to the chemical structure of the effector. Polypeptides typically contain a variety of functional groups; such as carboxylic acid (COOH), free amine ($—NH_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, IL. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,5667, 498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15 amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio) propionate), SPDB (N-succinimidyl-3-(2-pyridyldithio) butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3 (10): 1299-1304), or a 3'-N-amide analog (Lau et al., 1995, Bioorg-Med-Chem. 3 (10): 1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

In several embodiments, conjugates of a CAR, a T cell expressing a CAR, an antibody, or antigen binding portion thereof, and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are well known in the art, and can be isolated from natural sources according to known methods, produced using genetic engineering techniques (see Yu et al., (2002) PNAS 99:7968-7973), or maytansinol and maytansinol analogues prepared synthetically according to known methods. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference.

Additional toxins can be employed with a CAR, a T cell expressing a CAR, an antibody, or antigen binding portion thereof. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, MO). Contemplated toxins also include variants of the toxins (see, for example, see, U.S. Pat. Nos. 5,079,163 and 4,689,401).

Saporin is a toxin derived from *Saponaria officinalis* that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. Nos. 5,792,458 and 5,208,021.

Ricin is the lectin RCA60 from *Ricinus communis* (Castor bean). For examples of ricin, see, U.S. Pat. Nos. 5,079,163 and 4,689,401. *Ricinus communis* agglutinin (RCA) occurs in two forms designated RCA60 and RCA120 according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87,1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

A CAR, a T cell expressing a CAR, monoclonal antibodies, antigen binding fragments thereof, specific for one or more of the antigens disclosed herein, can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). A CAR, a T cell expressing a CAR, an antibody, or antigen binding portion thereof, can also be conjugated with enzymes that are useful for detection, such as horseradish peroxidase, β-galactosidase, luciferase, alkaline phosphatase, glucose oxidase and the like. When a CAR, a T cell expressing a CAR, an antibody, or antigen binding portion thereof, is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. A CAR, a T cell expressing a CAR, an antibody, or antigen binding portion thereof, may also be conjugated with biotin, and detected through indirect measurement of avidin or streptavidin binding. It should be noted that the avidin itself can be conjugated with an enzyme or a fluorescent label.

A CAR, a T cell expressing a CAR, an antibody, or antigen binding portion thereof, may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

A CAR, a T cell expressing a CAR, an antibody, or antigen binding portion thereof, can also be conjugated with a radiolabeled amino acid. The radiolabel may be used for both diagnostic and therapeutic purposes. For instance, the radiolabel may be used to detect one or more of the antigens disclosed herein and antigen expressing cells by x-ray, emission spectra, or other diagnostic techniques. Further, the radiolabel may be used therapeutically as a toxin for treatment of tumors in a subject, for example for treatment of a neuroblastoma. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

D. Nucleotides, Expression, Vectors, and Host Cells

Further provided by an embodiment of the invention is a nucleic acid comprising a nucleotide sequence encoding any of the CARs, an antibody, or antigen binding portion thereof, described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In some embodiments, the nucleotide sequence may be codon-modified. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-modified nucleotide sequence that encodes the antigen binding domain of the inventive CAR. In another embodiment of the invention, the nucleic acid may comprise a codon-modified nucleotide sequence that encodes any of the CARs described herein (including functional portions and functional variants thereof).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Integrated DNA Technologies (Coralville, IA, USA).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

Also provided is a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids can be incorporated into a recombinant expression vector. In this regard, an embodiment provides recombinant expression vectors comprising any of the nucleic acids. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors are not naturally-occurring as a whole.

However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, MD), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA).

Bacteriophage vectors, such as λUTIO, λUTI 1, λZapII (Stratagene), EMBL4, and λNMI 149, also can be used. Examples of plant expression vectors include pBIOI, pBI101.2, pBHO1.3, pBI121 and pBIN19 (Clontech). Examples of animal expression vectors include pEUK-Cl, pMAM, and pMAMneo (Clontech). The recombinant expression vector may be a viral vector, e.g., a retroviral vector or a lentiviral vector. A lentiviral vector is a vector derived from at least a portion of a lentivirus genome, including especially a self-inactivating lentiviral vector as provided in Milone et al., Mol. Ther. 17 (8): 1453-1464 (2009). Other examples of lentivirus vectors that may be used in the clinic, include, for example, and not by way of limitation, the LENTIVECTOR.RTM. gene delivery technology from Oxford BioMedica plc, the LENTIMAX.TM. vector system from Lentigen and the like. Nonclinical types of lentiviral vectors are also available and would be known to one skilled in the art.

A number of transfection techniques are generally known in the art (see, e.g., Graham et al., Virology, 52:456-467 (1973); Sambrook et al., supra; Davis et al., Basic Methods in Molecular Biology, Elsevier (1986); and Chu et al, Gene, 13:97 (1981).

Transfection methods include calcium phosphate co-precipitation (see, e.g., Graham et al., supra), direct micro injection into cultured cells (see, e.g., Capecchi, Cell, 22:479-488 (1980)), electroporation (see, e.g., Shigekawa et al., BioTechniques, 6:742-751 (1988)), liposome mediated gene transfer (see, e.g., Mannino et al., BioTechniques, 6:682-690 (1988)), lipid mediated transduction (see, e.g., Feigner et al., Proc. Natl. Acad. Sci. USA, 84:7413-7417 (1987)), and nucleic acid delivery using high velocity microprojectiles (see, e.g., Klein et al, Nature, 327:70-73 (1987)).

In an embodiment, the recombinant expression vectors can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

An embodiment further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupTI, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, $CD4^+/CD8^+$ double positive T cells, CD4+ helper T cells, e.g., Th1 and Th2 cells, $CD8^+$ T cells (e.g., cytotoxic T cells), tumor infiltrating cells, memory T cells, memory stem cells, i.e. Tscm, naive T cells, and the like. The T cell may be a $CD8^+$ T cell or a $CD4^+$ T cell.

In an embodiment, the CARs as described herein can be used in suitable non-T cells. Such cells are those with an immune-effector function, such as, for example, NK cells, and T-like cells generated from pluripotent stem cells.

Also provided by an embodiment is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs (including functional portions and variants thereof), nucleic acids, recombinant expression vectors, host cells (including populations thereof), and antibodies (including antigen binding portions thereof), can be isolated and/or purified. For example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

E. Methods of Treatment

It is contemplated that the CARs disclosed herein can be used in methods of treating or preventing a disease in a mammal. In this regard, an embodiment provides a method of treating or preventing cancer in a mammal, comprising administering to the mammal the CARs, the nucleic acids, the recombinant expression vectors, the host cells, the population of cells, the antibodies and/or the antigen binding portions thereof, and/or the pharmaceutical compositions in an amount effective to treat or prevent cancer in the mammal.

An embodiment further comprises lymphodepleting the mammal prior to administering the CARs disclosed herein. Examples of lymphodepletion include, but may not be limited to, nonmyeloablative lymphodepleting chemotherapy, myeloablative lymphodepleting chemotherapy, total body irradiation, etc.

For purposes of the methods, wherein host cells or populations of cells are administered, the cells can be cells that are allogeneic or autologous to the mammal. Preferably, the cells are autologous to the mammal. As used herein, allogeneic means any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically. As used herein, “autologous” means any material derived from the same individual to whom it is later to be re-introduced into the individual.

The mammal referred to herein can be any mammal. As used herein, the term “mammal” refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia, hairy cell leukemia, acute lymphocytic leukemia (ALL), and Burkitt’s lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer.

The terms “treat,” and “prevent” as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods can provide any amount or any level of treatment or prevention of cancer in a mammal.

Furthermore, the treatment or prevention provided by the method can include treatment or prevention of one or more conditions or symptoms of the disease, e.g., cancer, being treated or prevented. Also, for purposes herein, “prevention” can encompass delaying the onset of the disease, or a symptom or condition thereof.

Another embodiment provides a method of detecting the presence of cancer in a mammal, comprising: (a) contacting a sample comprising one or more cells from the mammal with the CARs, the nucleic acids, the recombinant expression vectors, the host cells, the population of cells, the antibodies, and/or the antigen binding portions thereof, or the pharmaceutical compositions, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the method of detecting the presence of a proliferative disorder, e.g., cancer, in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

The contacting can take place in vitro or in vivo with respect to the mammal. Preferably, the contacting is in vitro.

Also, detection of the complex can occur through any number of ways known in the art. For instance, the CARs disclosed herein, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles) as disclosed supra.

Methods of testing a CAR for the ability to recognize target cells and for antigen specificity are known in the art. For instance, Clay et al., J. Immunol, 163:507-513 (1999), teaches methods of measuring the release of cytokines (e.g., interferon-γ, granulocyte/monocyte colony stimulating factor (GM-CSF), tumor necrosis factor α (TNF-α) or interleukin 2 (IL-2)). In addition, CAR function can be evaluated by measurement of cellular cytotoxicity, as described in Zhao et al, J. Immunol, 174:4415-4423 (2005).

Another embodiment provides for the use of the CARs, nucleic acids, recombinant expression vectors, host cells, populations of cells, antibodies, or antigen binding portions thereof, and/or pharmaceutical compositions of the invention, for the treatment or prevention of a proliferative disorder, e.g., cancer, in a mammal. The cancer may be any of the cancers described herein.

Any method of administration can be used for the disclosed therapeutic agents, including local and systemic administration. For example, topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, a chemotherapeutic agent may be administered orally and an antibody or antigen binding fragment or conjugate or composition may be administered intravenously.

Methods of administration include injection for which the CAR, CAR T Cell, conjugates, antibodies, antigen binding fragments, or compositions are provided in a nontoxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody or antigen binding fragment to a region of tissue from which a tumor has been removed, or a region suspected of being prone to tumor development. In some embodiments, sustained intratumoral (or near-tumoral) release of the pharmaceutical preparation that includes a therapeutically effective amount of the antibody or antigen binding fragment may be beneficial. In other examples, the conjugate is applied as an eye drop topically to the cornea, or intravitreally into the eye.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies or conjugates can range from about 0.01 to about 30 mg/kg, such as from about 0.1 to about 10 mg/kg.

In particular examples, the subject is administered a therapeutic composition that includes one or more of the conjugates, antibodies, compositions, CARs, CAR T cells or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, the disclosed methods include providing surgery, radiation therapy, and/or chemotherapeutics to the subject in combination with a disclosed antibody, antigen binding fragment, conjugate, CAR or T cell expressing a CAR (for example, sequentially, substantially simultaneously, or simultaneously). Methods and therapeutic dosages of such agents and treatments are known to those skilled in the art, and can be determined by a skilled clinician. Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

In some embodiments, the combination therapy can include administration of a therapeutically effective amount of an additional cancer inhibitor to a subject. Non-limiting examples of additional therapeutic agents that can be used with the combination therapy include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the CARS, CAR-T cells, antibodies, antigen binding fragment, or conjugates disclosed herein. Methods and therapeutic dosages of such agents are known to those skilled in the art, and can be determined by a skilled clinician.

Additional chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masoprocol, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

In one embodiment, an effective amount of an antibody or antigen binding fragment that specifically binds to one or more of the antigens disclosed herein or a conjugate thereof is administered to a subject having a tumor following anti-cancer treatment. After a sufficient amount of time has elapsed to allow for the administered antibody or antigen binding fragment or conjugate to form an immune complex with the antigen expressed on the respective cancer cell, the immune complex is detected. The presence (or absence) of the immune complex indicates the effectiveness of the treatment. For example, an increase in the immune complex compared to a control taken prior to the treatment indicates that the treatment is not effective, whereas a decrease in the immune complex compared to a control taken prior to the treatment indicates that the treatment is effective.

F. Biopharmaceutical Compositions

Biopharmaceutical or biologics compositions (hereinafter, “compositions”) are provided herein for use in gene therapy, immunotherapy and/or cell therapy that include one or more of the disclosed CARs, or T cells expressing a CAR, antibodies, antigen binding fragments, conjugates, CARs, or T cells expressing a CAR that specifically bind to one or more antigens disclosed herein, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenous) or local (such as intra-tumor) administration. In one example, a disclosed CARs, or T cells expressing a CAR, antibody, antigen binding fragment, conjugate, is formulated for parenteral administration, such as intravenous administration. Compositions including a CAR, or T cell expressing a CAR, a conjugate, antibody or antigen binding fragment as disclosed herein are of use, for example, for the treatment and detection of a tumor, for example, and not by way of limitation, a neuroblastoma. In some examples, the compositions are useful for the treatment or detection of a carcinoma. The compositions including a CAR, or T cell expressing a CAR, a conjugate, antibody or antigen binding fragment as disclosed herein are also of use, for example, for the detection of pathological angiogenesis.

The compositions for administration can include a solution of the CAR, or T cell expressing a CAR, conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents, adjuvant agents, and the like, for example, sodium acetate, sodium chloride, potassium chloride, calcium chloride, sodium lactate and the like. The concentration of a CAR, or T cell expressing a CAR, antibody or antigen binding fragment or conjugate in these formulations can vary widely, and will be selected primarily based on fluid volumes, viscosities, body weight and the like in accordance with the particular mode of administration selected and the subject’s needs. Actual methods of preparing such dosage forms for use in in gene therapy, immunotherapy and/or cell therapy are known, or will be apparent, to those skilled in the art.

A typical composition for intravenous administration includes about 0.01 to about 30 mg/kg of antibody or antigen binding fragment or conjugate per subject per day (or the corresponding dose of a CAR, or T cell expressing a CAR, conjugate including the antibody or antigen binding fragment). Actual methods for preparing administrable compositions will be known or apparent to those skilled in the art and are described in more detail in such publications as Remington’s Pharmaceutical Science, $19^{th}$ ed., Mack Publishing Company, Easton, PA (1995).

A CAR, or T cell expressing a CAR, antibodies, antigen binding fragments, or conjugates may be provided in lyophilized form and rehydrated with sterile water before administration, although they are also provided in sterile solutions of known concentration. The CARs, or T cells expressing a CAR, antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. A CAR, or T cell expressing a CAR, antibodies, antigen binding fragments and conjugates thereof can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, PA, (1995). Particulate systems include microspheres, microparticles, microcapsules, nanocapsules, nanospheres, and nanoparticles. Microcapsules contain the therapeutic protein, such as a cytotoxin or a drug, as a central core. In microspheres, the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., *Colloidal Drug Delivery Systems*, J. Kreuter, ed., Marcel Dekker, Inc., New York, NY, pp. 219-342 (1994); and Tice & Tabibi, *Treatise on Controlled Drug Delivery*, A. Kydonieus, ed., Marcel Dekker, Inc. New York, NY, pp. 315-339, (1992).

Polymers can be used for ion-controlled release of the CARs, or T cells expressing a CAR, antibody or antigen binding fragment or conjugate compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44 (2): 58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, PA (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

G. Kits

In one aspect, kits employing the CARs disclosed herein are also provided. For example, kits for treating a tumor in a subject, or making a CAR T cell that expresses one or more of the CARs disclosed herein. The kits will typically include a disclosed antibody, antigen binding fragment, conjugate, nucleic acid molecule, CAR or T cell expressing a CAR as disclosed herein. More than one of the disclosed antibodies, antigen binding fragments, conjugates, nucleic acid molecules, CARs or T cells expressing a CAR can be included in the kit.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, CARs or T cells expressing a CAR. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed antibodies, antigen binding fragments, conjugates, nucleic acid molecules, CARs or T cells expressing a CAR, for example, in a method of treating or preventing a tumor or of making a CAR T cell. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Derivation of Human BCMA-Specific Binders from a Fully Human Yeast Display Library

Materials and Methods

A large yeast display human naive single chain variable fragment (ScFv) antibody library was used to isolate anti-human BCMA antibodies described herein. The library was constructed using a collection of human antibody gene repertoires from more than 60 individuals. Three rounds of magnetic-activated cell sorting (MACS) were performed to enrich human ScFv binders to the recombinant human BCMA (ectodomain)-Fc. For the first round of yeast library panning, the yeast display ScFv library ($5\times10^{10}$ cells) was incubated with 5 μg/ml BCMA-Fc in 15 ml PBSA (consisting of 0.1% Bovine Serum Albumin (BSA) in Dulbecco's phosphate-buffered saline (PBS) buffer), at room temperature on a rotator for 1.5 hours. After two times washing with 25 ml PBSA, the yeast library mix was incubated with 100 μL Protein G microbeads (Miltenyi Biotec) at room temperature on a rotator for 30 minutes. After one time washing, the library mix was resuspended in 50 ml of PBSA and loaded onto the MACS cell separation column (LS column). After three times washing with 10 ml PBSA. The yeast displayed ScFv binders to the column were then eluted two times with 2 ml PBSA. These eluted yeast cells were combined and then resuspended into 50 ml SDCAA medium (20 g D-glucose, 6.7 g BD Difco™ Yeast Nitrogen Base without Amino Acids, 5 g Bacto™ Casamino Acids, 5.4 g $Na_2 \cdot HPO_4$, and 8.56 g $NaH_2PO_4 \cdot H_2O$ in 1 L water) and amplified with shaking at 225 rpm at 30° C. for 20 hours. The amplified pool was then induced in SGCAA medium (consisting of the same composition of SDCAA medium, but containing galactose instead of glucose), with shaking at 225 rpm at 30° C. for another 16 hours and used for next round of panning. The same process was repeated two more times to enrich the BCMA-Fc specific binders.

To further enrich the binders with higher affinity and better specificity, FACS based sorting was employed to isolate the strongest binders from the pool. The induced pool was incubated with 0.1 μg/ml of biotinylated BCMA-Fc at room temperature for 1 hour and then stained with Anti-c-Myc-Alexa 488 and Streptavidin-PE conjugates, the top 1% of the pool with the highest PE versus FITC signal was gated and sorted. The sorted pool was amplified in SDCAA medium and yeast plasmid DNA was extracted and transformed into bacterial for single clone DNA sequencing. 50 random clones were sequenced and 48 unique sequences were identified. 17 clones designated as MTB-1, MTB-2, MTB-3, MTB-4, MTB-5, MTB-14, MTB-15, MTB-16, MTB-25, MTB-28, MTB-37, MTB-39, MTB-40, MTB-49, MTB-50, MTB-4-12 and MTB-4-45 were cloned into CAR constructs for CAR-T function screening.

Example 2

Generation and Testing of BCMA-Targeting CAR T Constructs Incorporating Fully Human Binder ScFv Sequences This Example 2 describes the creation of a CAR T cells targeting the tumor antigen BCMA for the treatment if MM and other BCMA-positive malignancies.

Schema of BCMA CAR design is shown in FIG. 1. Fully human ScFv binders targeting BCMA were linked in frame to CD8 hinge and transmembrane domain, 4-1BB costimulatory domain and CD3 zeta activation domain. CAR sequences were incorporated into third-generation lentiviral vectors and which were used in transduction of human primary T cells to generate the BCMA CAR T cells.

Table 1 below lists the BCMA CAR constructs built, designated by ScFv sequence used in CAR design in the left column, and the corresponding designation of the ScFv clone nomenclature in each construct in the right column.

TABLE 1

List of ScFv Clones used in CAR designs

| ScFv Sequence Designation | ScFv Clone nomenclature |
|---|---|
| sequence 1 | MTB-1 |
| sequence 2 | MTB-2 |
| sequence 3 | MTB-3 |
| sequence 4 | MTB-4 |
| sequence 5 | MTB-5 |
| sequence 14 | MTB-14 |
| sequence 15 | MTB-15 |
| sequence 16 | MTB-16 |
| sequence 25 | MTB-25 |
| sequence 28 | MTB-28 |
| sequence 37 | MTB-37 |
| sequence 39 | MTB-39 |
| sequence 40 | MTB-40 |

TABLE 1-continued

List of ScFv Clones used in CAR designs

| ScFv Sequence Designation | ScFv Clone nomenclature |
|---|---|
| sequence 49 | MTB-49 |
| sequence 50 | MTB-50 |
| sequence 4-12 | MTB-4-12 |
| sequence 4-45 | MTB-4-45 |

Figure 2:
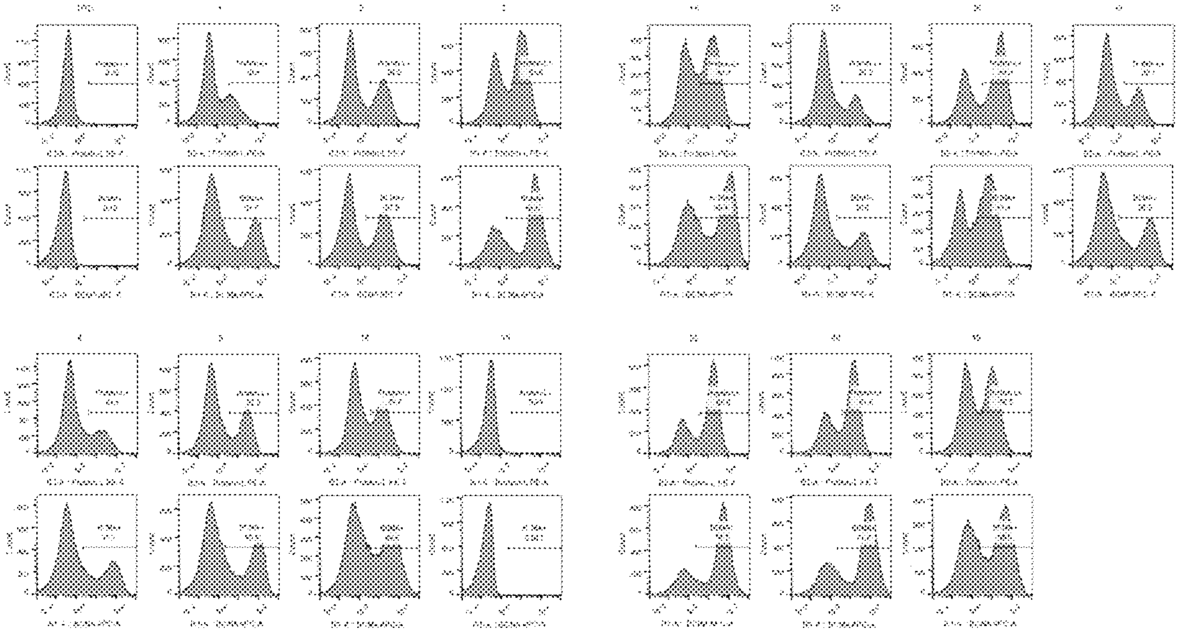
FIG. 2 depicts surface expression of BCMA-targeting CAR T constructs on human primary T cells. CAR T expression was determined by flow cytometry. T cells were activated with Miltenyi Biotec TransAct™ CD3 CD28 reagent in the presence of IL-2, and transduced with LV as described in Materials and Methods. On culture day 8, viable transduced T cells (7-AAD negative) were assayed for CAR surface expression using the Protein L method (top panel) or the BCMA-Fc method (bottom panel). The CAR construct identifier (ScFv number) used in each transduction is listed above each figure. Bars represent the percentage of CAR T-positive populations in relation to non-transduced T cell control (UTD).

The surface expression of anti-BCMA CARs incorporating single chain fragment variable 5 (ScFv) sequences, is shown in FIG. 2. The expression level for each ScFv-containing CAR was determined by flow cytometric analysis of LV-transduced T cells from healthy donors using either Protein L detection method, or the BCMA—Fc method. In a Protein L detection method, CAR T cells and controls were stained in a two-step procedure with: step 1) protein L-biotin conjugate, followed by step 2) streptavidin—PE reagent. In a BCMA-Fc method, cells were stained with: step 1: BCMA-Fc peptide; followed by step 2: anti-Fc APC reagent. Results from 10 both methods were taken into account when analyzing CAR expression. All CAR constructs were successfully expressed in human primary T cells, with the exception of CAR construct with ScFv sequence 15, which could not be detected by either of the staining methods (FIG. 2). Untransduced cells (UTD) were used as a negative staining control indicating the specificity of CAR T staining. Next, the cytolytic function of anti BCMA CARs was evaluated in a luciferase-based killing assay (FIG. 3).

CAR T cells were incubated with multiple myeloma BCMA-positive tumor lines RPMI-8226-luc, or MM1.S-luc, or with a BCMA-negative line 293T-luc, in order to control for non-specific CAR activation.

Effector CAR T cells and tumor cells were combined at effector to target (E:T) ratio of 5:1 or 10:1 in order to compare and contrast the potency of the different CAR constructs (FIG. 3). RPMI-8226 cells were most susceptible cell line to BCMA CAR-mediated tumor killing, with most CAR constructs achieving over 40% tumor lysis at the lowest E:T ratio of 5 (FIG. 3A), except for CARs containing ScFv sequence 1, sequence 2, sequence 15, or sequence 25, whereas the negative control untransduced T cells, the UTD group, caused no appreciable tumor lysis (FIG. 3A). In multiple myeloma MM1.S cells, which are less susceptible to cytolysis, strong killing function of CARs with ScFv sequence 5, sequence 16, sequence 37, and sequence 40 was observed, but not for the other constructs. The UTD group caused no appreciable tumor killing, indicating that the killing is CAR-specific (FIG. 3B). No killing of 293T cells, which lack the BCMA target antigen was seen, indicating the specificity of killing response (FIG. 3C).

Based on these results, CAR T constructs D0084, D0085, D0087, D0099, DO100, incorporating ScFv binder sequences 5, 16, 37, 40, 4-12, and 4-45, respectively, were used for further testing (Table 2).

TABLE 2

CAR Construct Numbers and the Corresponding ScFv sequences

| CAR Construct Number | LTG Number | ScFv Sequence Designation |
|---|---|---|
| D0084 | LTG2860 | sequence 5 |
| D0085 | LTG2861 | sequence 16 |
| D0086 | LTG2862 | sequence 37 |
| D0087 | LTG2863 | sequence 40 |

TABLE 2-continued

| CAR Construct Numbers and the Corresponding ScFv sequences | | |
|---|---|---|
| CAR Construct Number | LTG Number | ScFv Sequence Designation |
| D0099 | LTG2944 | sequence 4-12 |
| D0100 | LTG2945 | sequence 4-45 |

Next, expression of BCMA CAR constructs was evaluated by transduction of human CD4+CD8+ T cells at a fixed multiplicity of infection of 40 (FIG. 4). T cells were isolated from a human buffy coat product and transduced with lentiviral vectors encoding the CARs as described in Materials and Methods. CAR+ T cells were detected using BCMA-Fc peptide, followed by anti-Fc APC. Cells were counterstained with CD8 antibody-FL in order to confirm CAR expression among CD8+ and CD8−(CD4+) T cells. All constructs were expressed robustly, in CD4+ as well as CD8+ T cells. The total CAR expression frequencies ranged from 19.5% to 49.3% (FIG. 4).Data for one representative donor out of three transduction experiments is shown.

Then, CAR constructs D0084, D0085, D0087, D0099, D0100 were compared in terms of their tumor cytolytic capacity in a luciferase-based killing assay. Target lines stably expressing firefly luciferase were used, as above. CAR T cells from two separate donors are shown in order to demonstrate robustness and reproducibility of the results (FIG. 5).

Robust killing capacity of CARs D0084, D0085, D0087, D0099, D0100 was demonstrated in the BCMA-positive multiple myeloma cell lines MM1.S and RPMI-8226. No appreciable killing was observed in UTD negative control groups, indicating the dependence of the killing on CAR expression. Moreover, no killing was seen against BCMA-negative 293T cells, demonstrating that the killing is BCMA-dependent (FIG. 5).

Example 3

In Vivo Testing of BCMA-Targeting CAR T Constructs Incorporating Fully Human Binder ScFv Sequences Example 3 describes long-term in vitro, and xenograft model in vivo evaluation of a CAR T cells targeting the tumor antigen BCMA for the treatment in multiple myeloma and other BCMA-positive malignancies. These testing modalities provide a more stringent environment for CAR T evaluation, and better approximate the conditions that CAR T cells may encounter in human patients.

Note: for clarity and brevity, in this and the following Examples, one zero was omitted form CAR construct names shown in Table 2. Therefore, CAR construct D0100 became D100, CAR construct D0085 became D085, etc.

Materials and Methods

T-Cell Transduction and Culture

Primary CD4 and CD8 T-cells were activated with TransAct (Miltenyi Biotec, Auburn CA) according to the manufacturer's protocol. The cells were cultured overnight at a density of 1e6 cells/ml in TexMACS media (Miltenyi Biotec) supplemented with 30 U/ml of recombinant human IL-2 (Miltenyi Biotec). After 18-24 hours, the T-cells were transduced with lentiviral vectors containing the CAR constructs. The T-cells were incubated with the lentiviral vectors for 2 days, and the cultures were subsequently washed and resuspended in fresh TexMACS media with IL-2 and maintained at a density of 0.5e6 cells/ml. On day 6 or 7 after the start of T-cell culture, the cell surface expression of the CARs was assessed by flow cytometry.

Flow Cytometry Staining

To assess the cell surface expression of BCMA CARs, 0.5-1e6 CAR T-cells were resuspended in FACs buffer (Miltenyi Biotec's autoMACS Rinsing Solution+MACS BSA Stock Solution) and incubated with 0.5 μg of recombinant human BCMA Fc Chimera Protein (RNDsystems) for 20 mins at 4° C. Cells were washed twice and re-suspended in FACs buffer and incubated for 20 mins at 4° C. with anti-Fc-Alexa Fluor 647 at 1:200 dilution. Cells were again washed twice and resuspended in FACs buffer and incubated for 20 mins at 4° C. with anti-CD4-Vioblue or anti-CD8-Viogreen (Miltenyi Biotec) at 1:50 dilution and 7AAD at 1:20 dilution. Cells were subsequently washed and analyzed using the MACSQuant® Analyzer 10 flow cytometer (Miltenyi Biotec).

For exhaustion marker staining, CAR T-cells were resuspended in FACs buffer and incubated with anti-PD-1-Pevio770 (Miltenyi Biotec) and anti-LAG-3-APC (Biolegend) at 1:30 dilution. Memory markers were stained by incubating CAR T-cells with anti-CD45RO-Pevio770, anti-CD45RA-APC, and CD62L-PE (Miltenyi Biotec) at 1:30 dilution. For both exhaustion and memory staining panels, cells were additionally stained with CD8-Viogreen, CD3-Vioblue, and 7AAD. Cells were incubated with the antibodies for 20 mins at 4° C., and subsequently washed then acquired using the MACSQuant Analyzer 10 flow cytometer.

For intracellular cytokine staining, T-cells were incubated with target cells for 5-6 hours at 37° C. in the presence of Brefeldin A (BD Biosciences, CA). Cells were subsequently stained as previously described with cell surface markers CD8-Viogreen and CD3-Vioblue. After cell surface staining, cells were fixed and permeabilized with Fixation/Permeabilization Solution Kit (BD Biosciences) according to the manufacturer's protocol. Cells were then stained with anti-IFN-gamma-APC, anti-TNF-APCvio770, and IL-2-PE (Miltenyi Biotec) at dilutions suggested by the manufacturer. After staining, cells were analyzed using the MACSQuant Analyzer 10 flow cytometer.

Long-Term Co-Culture

For the long term co-culture experiment, CAR T-cells were co-cultured with target cells, MM1.S or RPMI-8226 expressing GFP, at an ETT ratio of 0.1-0.3. The cells were cultured in 6-well plates with TexMACS media that was either treated with 10 ng/ml of human recombinant TGF-β (Miltenyi Biotec) or remained untreated. The co-culture was fed by adding TGF-β-treated media or untreated media every 2-3 days. The absolute counts of T-cells and target cells at different time points during the long-term co-culture was assessed by quantifying the number of CD3+ cells and GFP+ cells using flow cytometry. The absolute counts were determined by normalizing the number of acquired cells using CountBright Absolute Counting Beads (Molecular Probes). When less than 15% of the target cells remained, T-cells from the co-culture were added to fresh target cells at an ETT ratio of 0.1-0.3 to initiate the subsequent round of co-culture. Additional rounds of co-culture were done until the T-cells no longer proliferated.

In Vivo Tumor Model

Female 7 to 8-week old NSG mice NOD.Cg-Prkdo$^{scid}$Il2rg$^{tmlWj}$l/SzJ) from Jackson Laboratory (Bar Harbor, ME) were intradermally injected on the abdomen with 8e6 RPMI-8226 cells. T-cells were intravenously injected after the tumors were allowed to engraft for 18-20 days and have reached volume sizes of >60 mm3 as measured via caliper. For groups receiving CAR T-cells, 5e6 CAR T-cells were infused, and the differences in CAR expression levels between groups were normalized by adjusting the number of total T-cells that was injected. The number of T-cells that was infused in the UTD group was the mean of the total T-cells that was injected in the CAR T-cell groups. On day 6-7 after T-cell infusion, 3-5 mice from each group (except the untreated group) were sacrificed for tumor harvest, while the rest were monitored for tumor progression and survival. Tumor sizes and body weights were measured every 2-3 days. Mice with tumor sizes reaching >1200 mm were sacrificed.

CAR constructs D100 and D085 were compared side-by side in a long-term co-incubation with targets in vitro. This assay facilitates long-term exposure of CAR-T cells to target antigens such as may occur in vivo and in the clinic, and may help identify critical differences in long-term function of CAR T cells. D100 and D085 CARs were comprised CD8 extracellular and transmembrane domain, 4-1BB/CD137 co-stimulation domain and CD3 activation domains, and differed only in the scFv sequence (FIG. 6A). Both CAR constructs achieved robust expression at MOI (multiplicity of infection) 10, 20, or 40. CAR T lines with similar CAR surface expression were chosen for the long term assay: 84.6% for D100, 81.5% for D085, (FIG. 6B).

CAR T and target cells were combined at the beginning of the first round of co-culture at E:T ratio of 0.1:1, then fresh target RPMI-8226 cells were spiked into the culture at the beginning of each consecutive round, to replace target cells which have been killed by CAR T cells, and maintain the desired E:T ratio (FIG. 6C). The BCMA CAR D100 demonstrated greater T cell expansion in the $1^{st}$, $3^{rd}$, and $4^{th}$ round of the long-term co-culture as compared to CAR D085 (FIG. 6D). In addition, CAR D100 mediated superior target cell killing in the long term, as seen in the $4^{th}$ co-culture round (FIG. 6E). Of note, in the course of the 20-day co-culture period, the percentage of CD8+ T cell subsets of both CAR D085 and D100 continued to increase, whereas the percentage of CD4+T in CAR D085 and D100 populations decreased, especially at the later stages of co-incubation (FIG. 6F). This is to be expected, as CD8+ T cells are known to dominate the later stages of the anti-tumor response. However, the percentage of both CD4+T and CD8+T subsets in CAR100 co-cultures with target cells remained higher than the respective T cell subsets in CAR085 (FIG. 6F). Finally, the production of inflammatory cytokines IL-2, and TNFα crucial for CAR T function, was greater in the CAR100 T cells, as compared to CAR085, whereas the levels of IFNγ were similar (FIG. 6G). Overall, the BCMA CAR D100 demonstrated superior target cell killing, expansion of CD4+T and CD8+T subsets, and cytokine elaboration, as compared to the BCMA CAR D085.

The in vivo anti-tumor function of BCMA CAR D085 and D100 were then evaluated in an RPMI-8226 intradermal xenograft mouse model. Mice were implanted with RPMI-8226 cells seventeen days prior to CAR T administration. Mice with established RPMI-8226 were treated with CAR T cells or untransduced cells (UTD) intravenously, and maintained for tumor progression analysis. Tumors were harvested from a subset of mice in each group six days after CAR administration, for CAR T function analysis (FIG. 7A). Tumor progression as recorded for a period of fifty days after tumor implant (FIG. 7B). Whereas both CAR D085 and CAR100 mediated tumor rejection in this xenograft model, the BCMA CAR D100 was more efficient and reduced tumor size to below the detection limit by study day 35, whereas in mice treated with CAR D085 tumors shrunk but were still detectable at the conclusion of the observation period (FIG. 7B). CAR D100 and CAR D085 both mediated 100% survival in this model, in contrast to untreated mice and the negative UTD control mice which have met sacrifice criteria (FIG. 7C). Therefore, CAR 100 was superior in anti-tumor function to CAR D085 in vivo, and showed no adverse toxicity.

An additional CAR candidate, CAR D153, was developed utilizing an scFv sequence 4-1c. The 4-1c scFv sequence was derived as described in Example 1. The 4-1c scFv sequence was incorporated into an identical CAR architecture to that used in CAR D100 and D085 as shown in FUGIRE 6A. Transduction of CAR D153 lentiviral vector into primary human T cells achieved comparable CAR expression levels to CAR D085 and CARD100 (FIG. 8A). Moreover, CAR D153 mediated potent lysis of BCMA-positive multiple myeloma target cell lines RPMI-8226 and MM1.S, similarly to CAR D100 and CARD085 (FIG. 8B). In the intradermal xenograft RPMI-8226 in vivo model (FIG. 7A), CAR D153 demonstrated potency equal or greater to that of the BCMA CAR D100 (FIG. 8C). Therefore, CAR D153 represents another highly efficient candidate for the treatment of BCMA-positive malignancies.

Example 4

Generation and Testing of an Armored BCMA CAR Incorporating a TGFβ Decoy Receptor for Improved CAR Potency in Suppressive Tumor Microenvironment Example 4 describes the development and characterization of an armored BCMA CAR incorporating a TGFBRII DN, a dominant-negative form of the TGFβ receptor, for superior anti-tumor performance.

Materials and Methods

Generation of the TGFBRII Dominant Negative BCMA CAR

The sequence of the extracellular and transmembrane domains of the human TGFβRII (GenBank ID: AHI94914.1, amino acid residues 1-191), was cloned downstream of the BCMA D100 CAR. The CAR and the TGFβRII sequences were separated by a ribosome skip site (P2A), which was derived from the porcine teschovirus-1 polyprotein (AA 976-997, GenBank ID: CAB40546.1, mutated residue P977S). P2A is flanked on each side with a furin cleavage site (amino acids: RAKR). All DNA sequences were codone-optimized (IDT DNA, Coralville, IA).

Results

Clinical studies have revealed that resistance to BCMA CAR T therapy may emerge due to tumor-suppressive microenvironment, in part in the bone marrow. To better equip the BCMA CAR T cells for tumor-suppressive scenarios, the D100 CAR sequence has been combined with a decoy TGFβ receptor, to generate an armored BCMA CAR (FIG. 9A). The TGFβRII DN decoy receptor is comprised of the extracellular ligand binding domain and the transmembrane region of the TGFβRII, but lacks the intracellular signaling kinase domain of the TGFβ receptor. The BCMA CAR100 and the TGFβ decoy sequence were combined in a bicistronic expression cassette in a lentiviral vector backbone under the control of EF-1α promoter, to facilitate equal co-expression of both the CAR and the decoy receptor polyproteins in T cells (FIG. 9A). This armored BCMA CAR construct is termed D158. Successful transduction of the D158 construct into human primary T cells was achieved (FIG. 9B). To evaluate the armored BCMA CAR D158 function, an experimental co-culture with RPMI-8226 target cells was performed for two rounds of target addition (FIG. 9C). CAR D100, which shares the CAR sequence with the armored CAR construct D158, but lacks the armored decoy element, was included for comparison (FIG. 9D, 9E). A subset of co-cultures was treated with 10 ng/ml soluble TGFβ during co-incubation, to mimic the immunosuppressive tumor microenvironment. In both the first and the second round of co-incubation, the expansion of D100 BCMA CAR in the presence of soluble TGFβ was suppressed as compared to TGFβ-free culture. By contrast, the expansion of the armored BCMA CAR construct D158 remained unaffected by TGFβ addition (FIG. 9D). Subsequently, target cell counts remained similarly repressed between experimental groups in the first round of co-incubation, but have resurged in the second round in CAR 100 group spiked with soluble TGFβ, whereas the armored CAR maintained strong repression of tumor cells expansion regardless of TGFβ addition throughout the experiment (FIG. 9E). These findings demonstrate the protective effects of TGFβ armored BCMA CAR T cells in TGFβ-rich, T-cell suppressive tumor environment.

The sources of TGFβ in tumor microenvironment may include the tumor cells or the stromal cells, The RPMI-8226 multiple myeloma cells are capable of producing TGFβ in its inactive form (FIG. 10A), which may then be converted to its active form by other elements of tumor microenvironment in vivo.

The armored BCMA CAR D158 and the respective non-armored D100 BCMA CAR were evaluated in the RPMI-8226 intradermal xenograft model in vivo (FIG. 10B). Despite an unexpected anti-tumor effect observed in the mice treated with untransduced T cells (UTD), the armored CAR D158 demonstrated a superior tumor control as compared to the non-armored CAR version with same CAR sequence, D100 (FIG. 10C). Both the armored CAR D158 and the non-armored CAR D100 mediated 100% survival in this mouse model (FIG. 10D). In tumor tissue harvested six days after CAR administration, tumors of mice treated with the armored BCMA CAR D158 contained greater absolute T cell counts (FIG. 10E), and T cell percentage (FIG. 10F) than tumors of mice treated with the non-armored CAR D100. In addition, the armored CAR D158 mediated greater PD-1 expression on tumor-infiltrating lymphocytes (TIL) (FIG. 10G), and greater TIL memory cell fraction (FIG. 10H). These observations point to a stronger T cell activation and greater memory formation by the armored CAR D158, as compared to the non-armored CAR D100. Overall, the armored BCMA CAR D158 demonstrates a more potent anti-tumor activity in vivo as compared to the non-armored CAR D100, greater tumor infiltration, stronger activation and memory formation. All these features suggest a potential greater clinical benefit of the armored CAR D158.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

What is claimed is:

1. An isolated nucleic acid molecule encoding a chimeric antigen receptor (CAR) comprising the amino acid sequence of SEQ ID NO: 78.

2. A vector comprising the nucleic acid molecule of claim 1.

3. The vector of claim 2, wherein the vector is selected from the group consisting of a DNA vector, an RNA vector, a plasmid vector, a cosmid vector, a herpes virus vector, a measles virus vector, a lentivirus vector, an adenoviral vector, and a retrovirus vector.

4. The vector of claim 2, further comprising a promoter.

5. The vector of claim 4, wherein the promoter is an inducible promoter, a constitutive promoter, a tissue specific promoter, a suicide promoter or any combination thereof.

6. An isolated cell comprising the vector of claim 2.

7. The isolated cell of claim 6, wherein the cell is a T cell.

8. The isolated cell of claim 6, wherein the T cell is a $CD8^+$ T cell.

9. The isolated cell of claim 6, wherein the cell is a human cell.

10. The isolated nucleic acid molecule of claim 1, wherein the isolated nucleic acid molecule encodes a chimeric antigen receptor (CAR) comprising the amino acid sequence of SEQ ID NO: 98 or SEQ ID NO: 102.

11. A pharmaceutical composition comprising an anti-tumor effective amount of a population of isolated human T cells, wherein the T cells comprise a nucleic acid sequence that encodes a CAR encoded by the isolated nucleic acid molecule of claim 1, and wherein the T cells are T cells of a human having a cancer.

12. The pharmaceutical composition of claim 11, wherein the T cells are T cells of a human having a hematological cancer.

13. The pharmaceutical composition of claim 12, wherein the hematological cancer is leukemia or lymphoma.

14. The pharmaceutical composition of claim 13, wherein the leukemia is acute myeloid leukemia (AML), blastic plasmacytoid dendritic cell neoplasm (BPDCN), chronic myelogenous leukemia (CML), chronic lymphocytic leukemia (CLL), acute lymphoblastic T cell leukemia (T-ALL), or acute lymphoblastic B cell leukemia (B-ALL).

15. The pharmaceutical composition of claim 13, wherein the lymphoma is mantle cell lymphoma, non-Hodgkin's lymphoma or Hodgkin's lymphoma.

16. The pharmaceutical composition of claim 12, wherein the hematological cancer is multiple myeloma.

17. The pharmaceutical composition of claim 11, wherein the human cancer is an oral and pharynx cancer, a digestive system cancer, a respiratory system cancer, a bone and joint cancer, a soft tissue cancer, a skin cancer, a pediatric cancer, a cancer of the central nervous system, a cancer of the breast, a cancer of the genital system, a cancer of the urinary system, a cancer of the eye and orbit, a cancer of the endocrine system, and a cancer of the brain.

18. A CAR encoded by the isolated nucleic acid molecule of claim 1.

19. A method of making a cell comprising transducing a T cell with a vector of claim 2.

20. A method of generating a population of RNA-engineered cells comprising introducing an in vitro transcribed RNA or a synthetic RNA into a cell in vitro, wherein the RNA comprises the nucleic acid molecule of claim 1.

21. A process for producing a CAR-expressing cell, the process comprising introducing the isolated nucleic acid of claim 1 into an isolated cell.

22. The process for producing a CAR-expressing cell according to claim 21, wherein the cell is an isolated T cell or an isolated cell population containing a T cell.

23. An isolated nucleic acid molecule encoding a chimeric antigen receptor (CAR) comprising the amino acid sequence of SEQ ID NO: 98 or SEQ ID NO: 102.

* * * * *

UNITED STATES PATENT AND TRADEMARK OFFICE

CERTIFICATE OF CORRECTION

PATENT NO. : 12,391,740 B2
APPLICATION NO. : 17/337018
DATED : August 19, 2025
INVENTOR(S) : Dina Schneider et al.

It is certified that error appears in the above-identified patent and that said Letters Patent is hereby corrected as shown below:

In the Claims

Column 171
Line 4, in Claim 21, after "acid" insert -- molecule --

Signed and Sealed this
Fourth Day of November, 2025

John A. Squires
*Director of the United States Patent and Trademark Office*